(12) United States Patent
Harris, Jr. et al.

(10) Patent No.: US 9,351,998 B2
(45) Date of Patent: May 31, 2016

(54) METHODS OF NOURISHING ANIMALS

(71) Applicant: MariCal, Inc., Portland, ME (US)

(72) Inventors: H. William Harris, Jr., Saltville, VA (US); Marlies Betka, South Portland, ME (US); Chris Frederick Holm, Portland, ME (US); Steven Harold Jury, Scarborough, ME (US)

(73) Assignee: MARICAL, INC., Portland, ME (US)

(*) Notice: Subject to any disclaimer, the term of this patent is extended or adjusted under 35 U.S.C. 154(b) by 17 days.

(21) Appl. No.: 14/148,242

(22) Filed: Jan. 6, 2014

(65) Prior Publication Data

US 2014/0370120 A1 Dec. 18, 2014

Related U.S. Application Data

(63) Continuation of application No. 12/993,783, filed as application No. PCT/US2009/003165 on May 22, 2009, now Pat. No. 8,642,533.

(60) Provisional application No. 61/128,619, filed on May 22, 2008.

(51) Int. Cl.

| | |
|---|---|
| *A61K 31/315* | (2006.01) |
| *A61K 31/20* | (2006.01) |
| *A61K 38/00* | (2006.01) |
| *A61K 33/34* | (2006.01) |
| *A23K 1/16* | (2006.01) |
| *A23K 1/175* | (2006.01) |
| *A23K 1/18* | (2006.01) |
| *A61K 31/137* | (2006.01) |
| *A61K 31/19* | (2006.01) |
| *A61K 31/198* | (2006.01) |
| *A61K 31/28* | (2006.01) |
| *A61K 31/593* | (2006.01) |
| *A61K 33/06* | (2006.01) |
| *A61K 33/30* | (2006.01) |
| *A61K 33/32* | (2006.01) |
| *A61K 45/06* | (2006.01) |
| *A61K 31/59* | (2006.01) |
| *A61K 31/138* | (2006.01) |

(52) U.S. Cl.
CPC .............. *A61K 33/34* (2013.01); *A23K 1/1603* (2013.01); *A23K 1/1612* (2013.01); *A23K 1/1631* (2013.01); *A23K 1/1634* (2013.01); *A23K 1/1646* (2013.01); *A23K 1/1753* (2013.01); *A23K 1/1758* (2013.01); *A23K 1/182* (2013.01); *A23K 1/184* (2013.01); *A23K 1/1826* (2013.01); *A61K 31/137* (2013.01); *A61K 31/138* (2013.01); *A61K 31/19* (2013.01); *A61K 31/198* (2013.01); *A61K 31/28* (2013.01); *A61K 31/315* (2013.01); *A61K 31/59* (2013.01); *A61K 31/593* (2013.01); *A61K 33/06* (2013.01); *A61K 33/30* (2013.01); *A61K 33/32* (2013.01); *A61K 45/06* (2013.01)

(58) Field of Classification Search
CPC ...... A61K 31/315; A61K 31/20; A61K 38/00
USPC .................................. 514/1.1, 494, 561, 562
See application file for complete search history.

(56) References Cited

U.S. PATENT DOCUMENTS

| | | |
|---|---|---|
| 5,981,518 A | 11/1999 | Bernstein |
| 6,210,964 B1 | 4/2001 | Brown et al. |
| 6,523,496 B1 | 2/2003 | Keithly et al. |
| 8,642,533 B2 | 2/2014 | Harris, Jr. et al. |
| 2007/0060625 A1 | 3/2007 | Geibel et al. |
| 2007/0269495 A1 | 11/2007 | Ashmead |
| 2013/0196958 A1 | 8/2013 | Harris et al. |

FOREIGN PATENT DOCUMENTS

KR 1020040090372 A 10/2004

OTHER PUBLICATIONS

International Search Report for Int'l Application No. PCT/US2009/003165; Date Mailed: Jan. 27, 2010.
Written Opinion of the International Searching Authority for Int'l Application No. PCT/US2009/003165; Date Mailed: Jan. 27, 2010.
International Preliminary Report on Patentability for Int'l Application No. PCT/US2009/003165; Date Mailed: Nov. 23, 2010.
Breitwieser, G.E., et al., "Calcium Sensing Receptors as Integrators of Multiple Metabolic Signals," *Cell Calcium*, vol. 35, No. 3, pp. 209-216 (Mar. 2004), XP002550195.
Harrington, P.E. and Fotsch, C., "Calcium Sensing Receptor Activators: Calcimimetics," *Current Medicinal Chemistry*, vol. 14, No. 28, pp. 3027-3034 (2007), XP009124010.
Hebert, S.C., et al., "Functions and Roles of the Extracellular $Ca^{2+}$-Sensing Receptor in the Gastrointestinal Tract," *Cell Calcium*, vol. 35, No. 3, pp. 239-247 (Mar. 2004), XP002550232.
Nemeth, E.F., et al., "Calcilytic Compounds: Potent and Selective $Ca^{2+}$ Receptor Antagonists that Stimulate Secretion of Parathyroid Hormone," *The Journal of Pharmacology and Experimental Therapeutics*, vol. 299, No. 1, pp. 323-331 (Oct. 2001), XP002550231.
Yi, G. F, et al., "Determining the Methionine Activity of Mintrex Organic Trace Minerals in Broiler Chicks by Using Radiolabel Tracing or Growth Assay," *Poultry Science*, vol. 86, No. 5, pp. 877-887 (May 2007), XP002550194.

*Primary Examiner* — Raymond Henley, III
(74) *Attorney, Agent, or Firm* — Hamilton, Brook, Smith & Reynolds, P.C.

(57) ABSTRACT

The present invention relates to methods of maintaining, and methods of restoring, a desired calcium homeostasis in a non-human terrestrial animal by administering an effective amount of one or more Calcium-Sensing Receptor modulators (CaSRs) to the animal. The invention further provides methods of reducing foot lesions in chickens. The invention also relates to food compositions useful in the methods of the invention.

20 Claims, 54 Drawing Sheets

```
AATTCGGCACGAGGGGCAGCTGGGGGGCCGGCGGGGGATGCTGCCGCCGCCCTGCCCAGC
GCCGGAGTAAGGGCAAGAGCTGGTGGCGGCAGGAGCGGCCCCGGCGGCGGGACGAGTTCT
TGAAGATGGGCTCTCTGTAATGCTTTGGTCATGAAGAAACAAGGAACACTGAATTGCTGT
TTTACAATGGAGAAAACAGAGGGACAAATACCAGCACTGTGGCTTCCACCTTGTTGCTTA
TCTCTCTGCAGACATGTGTCCCAAATGCTCTCTGGGCTGTATTAAGGAAAGGAAAAGCTT
AGACATTACAACATCCGCTTTCTTACATCGTCTTTTCCAATTTTACATCCTATAACCCCT
TGGTGAAAGGAGGAACAATGACTTTATATAGCTGCTGTTTGATTCTTTTGCTGTTTACCT
GGAACACTGCTGCCTATGGGCCAAACCAACGGGCACAGAAGAAGGGAGACATTATTCTTG
GAGGATTGTTCCCCATCCATTTTGGAGTGGCTGCTAAAGACCAGGATCTAAAGTCAAGAC
CCGAATCAGTGGAGTGCATAAGGTATAATTTCCGAGGCTTCCGCTGGCTCCAGGCTATGA
TCTTTGCCATAGAAGAAATAAATAATAGCCCAAATCTCCTTCCCAACATGACCTTGGGAT
ACAGGATATTTGACACTTGCAATACAGTCTCTAAAGCCCTTGAGGCCACTCTGAGTTTTG
TGGCCCAGAACAAGATAGACTCCTTGAACCTGGATGAATTCTGCAACTGCTCAGAACATA
TCCCTTCCACCATTGCAGTCGTGGGGCAACCGGCTCTGGGGTTTCCACCGCTGTGGCCA
ATCTGCTGGGACTCTTTTACATACCTCAGGTCAGCTATGCCTCATCCAGTCGTCTCTTGA
GCAACAAGAACCAGTTCAAGTCCTTCCTCCGCACAATCCCCAATGACGAGCATCAGGCCA
CTGCGATGGCAGACATCATCGAGTACTTCCGCTGGAACTGGGTGGGAACGATTGCAGCTG
ATGATGACTATGGCCGGCCAGGGATTGAAAAGTTTCGGGAGGAGGCGGAGGAGAGAGATA
TCTGCATTGATTTTAGTGAGCTCATCTCCCAGTACTCAGATGAAGAAGAGATTCAGCAGG
TGGTGGAGGTCATCCAGAACTCCACAGCACGAGTGATTGTGGTTTTCTCCAGTGGACCAG
ACCTGGAACCCCTCATCAAAGAGATTGTCAGGCGAAACATCACTGGAAAGATCTGGCTGG
CAAGTGAAGCCTGGGCCAGTTCATCCCTGATAGCCATGCCAGAGTTCTTCCGTGTCATCG
GCAGCACCATTGGGTTTGCACTGAAGGCAGGCCAGATCCCAGGCTTTCGCGAGTTCCTGC
AGAAGGTGCATCCCAAAAAGTCTGCCAACAATGGATTTGCCAAGGAGTTTTGGGAAGAGA
CATTTAACTGCTATCTCCCCAGTGAGTCCAAAAATTCTCCAGCTTCAGCTTCCTTCCACA
AGGCCCACGAAGAGGGCTTGGGAGCTGGAAATGGTACAGCTGCCTTCCGACCTCCATGCA
CAGGTGATGAGAACATCACCAGTGTGGAAACACCGTACATGGACTTCACACACTTGCGGA
TATCCTATAATGTATATTTGGCAGTATATTCTATTGCTCACGCTTTGCAGGATATATATA
CTTGTACCCCTGGGAAAGGACTCTTCACCAACGGATCCTGTGCAGACATTAAGAAGGTTG
AGGCATGGCAGGTTCTGAAGCACCTGCGCCACTTAAATTTCACCAGTAACATGGGGGAGC
```

FIG. 2A

AAGTGGACTTTGATGAGTTTGGAGACCTGGTGGGGAATTACTCAATAATCAACTGGCATC
TCTCTCCAGAGGATGGCTCAGTCGTCTTTGAGGAGGTTGGGCACTACAATGTGTATGCCA
AGAAAGGGGAGAGGCTCTTTATCAATGAAAACAAAATCCTGTGGAGTGGATTCTCAAAGG
AGGTGCCCTTCTCTAACTGCAGCAGGGACTGCCTGCCAGGCACCAGGAAGGGCATTATTG
AGGGAGAGCCCACTTGCTGCTTCGAGTGTGTGGACTGCCCTGATGGGGAGTACAGTGATG
AAACAGATGCAAGTGCTTGTGACAAGTGCCCTGAGGATTACTGGTCTAATGAGAACCACA
CATCCTGCATCCCCAAGCAGATAGAGTTTCTATCCTGGACAGAGCCCTTTGGAATCGCTT
TAACTCTCTTTGCTGTGCTGGGAATTTTCCTGACTTCTTTTGTCCTGGGAGTCTTCACCA
AATTTCGCAACACTCCCATCGTCAAGGCCACAAACCGGGAGCTGTCCTACCTCCTCCTCT
TCTCCTTGCTCTGCTGCTTCTCTAGCTCATTGTTCTTCATTGGAGAGCCACAGAACTGGA
CTTGCCGTCTGCGGCAGCCAGCTTTTGGCATCAGCTTTGTCCTCTGCATCTCCTGCATCC
TGGTGAAAACCAATCGTGTCCTGCTTGTCTTCGAGGCAAAGATCCCTACAAGCCTCCACC
GAAAATGGTGGGGCCTCAACCTCCAGTTCCTCCTGGTCTTCTTGTGCACATTTGTGCAGA
TTGTCATCTGCGTGATTTGGCTCTACACGGCCCCACCATCCAGTTATCGAAACCATGAGC
TGGAGGATGAGATTATCTTCATCACCTGCCATGAAGGCTCCTTGATGGCCCTTGGCTTCC
TCATTGGCTACACCTGTCTCCTGGCAGCCATCTGCTTCTTCTTTGCCTTTAAGTCTCGAA
AACTGCCTGAGAACTTCAATGAGGCCAAGTTCATCACCTTCAGCATGCTGATCTTCTTCA
TTGTCTGGATCTCCTTCATCCCTGCTTACGCCAGCACATATGGCAAATTTGTCTCTGCTG
TGGAGGTGATTGCAATACTGGCTGCCAGTTTTGGGCTTCTGGCCTGCATCTTCTTTAACA
AAGTCTACATCATCCTCTTCAAGCCTTCCCGCAACACAATCGAGGAGGTGCGCTGCAGCA
CAGCTGCCCACGCTTTCAAGGTGGCCGCCAGGGCCACGCTGAGACGCAGCAATGTGTCAC
GCAAGCGTTCCAACAGCCTCGGAGGTTCCACCGGTTCCACCCCATCCTCCTCCATCAGCA
GCAAGAGCAACCATGAAGACCCTTTTCCTCTACCGGCTTCTGCTGAGCGGCAGCGGCAGC
AGCAGCGTGGGTGCAAGCAGAAGGTCAGCTTTGGGAGTGGTACGGTCACCTTGTCACTGA
GTTTTGAGGAGCCACAGAAGAACGCCATGGCCAACAGGAACGCCAAGCGCAGGAACTCCC
TGGAGGCCCAGAACAGCGATGACAGCCTGATGCGGCACAGGGCCCTGCTCGCTCTACAGA
ACAGCGAGTCCCTCAGTGCCGAGCCTGGCTTCCAGACAGCATCCAGCCCAGAGACCAGTT
CACAGGAGTCGGTAGTGGGAGACAACAAAGAAGAGGTACCAAACCCTGAGGCAGAGCCCT
CCCTGCCGTCAGCTAACTCCCGAAATTTTATAGGCACTGGAGGCAGCTCTGTCACAGAAA
ACACAGTACATTCCTAACAAAAGAAGGTCATGAAAAGCACTTCCCCAGGAGGAACTTGCT
CACCTCTTGCTTCTGAATGGGAAAGACAACAAAGATACATATCTGTGACACAGTCCCACC
ACACATTGTTGCTATCACCAGCAGGGTAAAACACGTGCCTCCAGAGGAAAGACTACCAGA
AGCCTGTGTGTGGGGAGCCTCAAACTGAATTTGCAGTTGCTTTACTGAAATCAGGACACG
TGGGGAGGACAAGTGAAGATTGCCTCTGGTGGGGCTTTAAGTAGAACTCTGCATATTGTC

FIG. 2B

```
TTGCCTCTGTAAGCTTTTCCTGCCAGACTGCAACTCAGCTGACTATGGGAGGCACTGAGC
AATTCCACTATACTCTGCTTTTACATTTATGTATAATATTCCTCTTTCCCACTATGTATA
ATATTCCCTCTTTATCCAGTATATGTGATCTGTAACCACGTGCATCAGGACTCTCAGCTC
TTCAAAAGCAAGACACACGGTTTCACTTGGGGAAAGCACGGTCATTGGGAAAATAAAAAA
GCCCCCAACATCCTGCATGCTGTGTACAGCCAAGGGTGTGAACATGTAAAGTATTTAATG
TGACAGAGCACCCTGCTATTTATATTTAGTAATGTCCCAATTTCTCCTCTCTGCCCAGCA
GGAAATACTGGACAATACCCTTCATAGACTCCATTGCACTAGACCAAGCTACTAGGTTCC
TACTGGTTTCTTCCAGCAGATGTAGCTTTACCTCCAGCCTGCCTGCTTTGGTGGAAGGGG
AGAACAGGTTGTAAATCCCCCTGGAGATTGCTGCGAGAGCACAATGAGATGTATTCGTGA
TTGATTATGTCGCTAGTAGTTGTATGCTTAACAAAGTGTTGCTGCTGTAATATTCCACAT
GGCATACGTGGCTAACCCTTCCACACCATAGTCAGTGTTGTGCTTTGCCATATTAATCCG
CCTCATACCCACACATAGCATTGCGCTGGTTGTGACAATACTTGTGGGCCTGATACAAAG
CCAATGAAACAAGGTGAAATGGAGAAATAGCCCCCAAATTTGATAATATTTGAGATGAGT
ATTGCAAGTGTGCATGGTGGTAGAGGATGGAGTAAATAAAACATACAGAGTTGGGCTCTG
AGACGTGCAAACAGACAAATGAGTAAATTGGATGTTTGGTTCCTGTAGGCCTTCAAGTAG
GTTATGTCCCTGTTGGCCCATCTTGAAGAGACAGTACCTAAACAAGAAGAGTGCACTGTG
CCTTGGTGAGAGTAAGGACTTCAAAAGAGAGCACATCAGAACTTCATTAGTCTTGGCTCT
TGTTCAGCACCCCAAAAGTAGACATAAGTGCTCCTGACTGTGCACGATGTGCCCGGTTCC
TCTGCATTCTGCGAATGTTGAAGTAAGAGAGTCCTTAGAACAGATTTCTGTTGCAGCCTG
AAGAAAGAAAGAGTGACCCTAGGCAACTTGGCAGGAAGGGCAAGGTTATTCTGTAGAATT
TACTTCCCTCTTCCCAGATCCCATATGCAAGAACAGGTATTTGTCATGAGGATATCAGTA
CCTGCCCTCATCACACACAGAGGCACTCTAGACCACTGCGGAAAGGTATATAGGCCTGCT
ACTTATTGTGAATGGAGATGAAAGGACTGTTGTGAATGTGATGGGGAAAATACCACAATT
CTCTTGTTACTGTTTTTGCTTGGTTGATGTTTTGTGTTTTGTGTGGTTTTTTTCTCGCC
AGAGCAGGAAAATAAAACTTACAGGTGACATTACTGCAAAAAAAAAAAAAAAAAAC
```

(SEQ ID NO:1)

FIG. 2C

MTLYSCCLILLLFTWNTAAYGPNQRAQKKGDIILGGLFPIHFGVAAKDQDL
KSRPESVECIRYNFRGFRWLQAMIFAIEEINNSPNLLPNMTLGYRIFDTCN
TVSKALEATLSFVAQNKIDSLNLDEFCNCSEHIPSTIAVVGATGSGVSTAV
ANLLGLFYIPQVSYASSSRLLSNKNQFKSFLRTIPNDEHQATAMADIIEYFR
WNWVGTIAADDDYGRPGIEKFREEAEERDICIDFSELISQYSDEEEIQQVV
EVIQNSTARVIVVFSSGPDLEPLIKEIVRRNITGKIWLASEAWASSSLIAMPE
FFRVIGSTIGFALKAGQIPGFREFLQKVHPKKSANNGFAKEFWEETFNCY
LPSESKNSPASASFHKAHEEGLGAGNGTAAFRPPCTGDENITSVETPYM
DFTHLRISYNVYLAVYSIAHALQDIYTCTPGKGLFTNGSCADIKKVEAWQV
LKHLRHLNFTSNMGEQVDFDEFGDLVGNYSIINWHLSPEDGSVVFEEVG
HYNVYAKKGERLFINENKILWSGFSKEVPFSNCSRDCLPGTRKGIIEGEPT
CCFECVDCPDGEYSDETDASACDKCPEDYWSNENHTSCIPKQIEFLSWT
EPFGIALTLFAVLGIFLTSFVLGVTKFRNTPIVKATNRELSYLLLFSLLCCF
SSSLFFIGEPQNWTCRLRQPAFGISFVLCISCILVKTNRVLLVFEAKIPTSLH
RKWWGLNLQFLLVFLCTFVQIVICVIWLYTAPPSSYRNHELEDEIIFITCHE
GSLMALGFLIGYTCLLAAICFFFAFKSRKLPENFNEAKFITFSMLIFFIVWIS
FIPAYASTYGKFVSAVEVIAILAASFGLLACIFFNKVYIILFKPSRNTIEEVRC
STAAHAFKVAARATLRRSNVSRKRSNSLGGSTGSTPSSSISSKSNHEDPF
PLPASAERQRQQQRGCKQKVSFGSGTVTLSLSFEEPQKNAMANRNAKR
RNSLEAQNSDDSLMRHRALLALQNSESLSAEPGFQTASSPETSSQESVV
GDNKEEVPNPEAEPSLPSANSRNFIGTGGSSVTENTVHS  (SEQ ID NO:2)

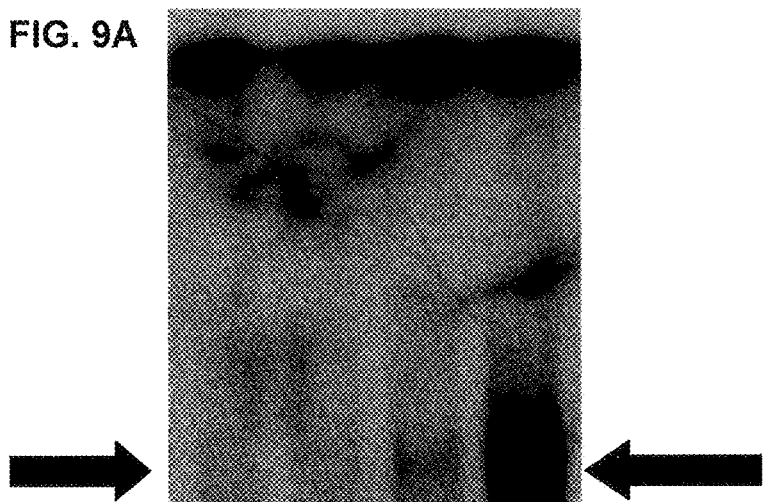
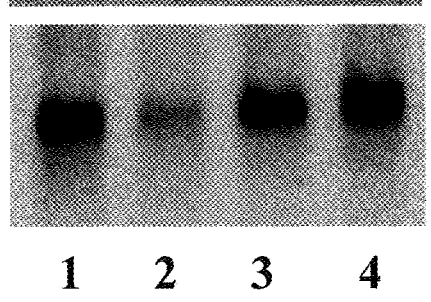

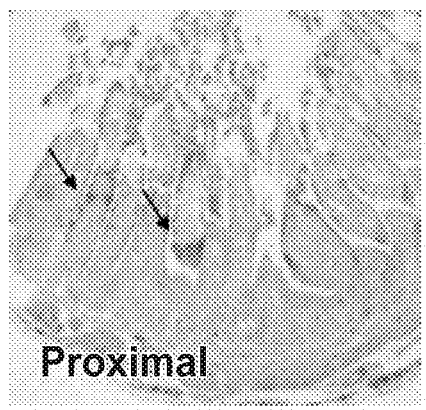
FIG. 11A Proximal
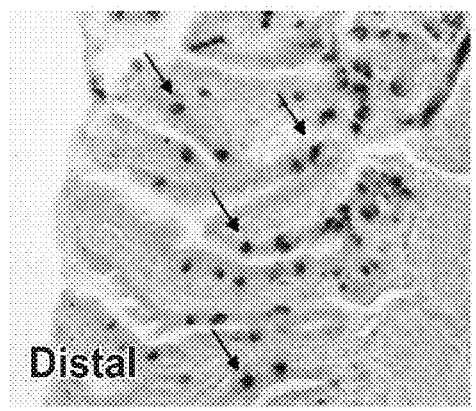
FIG. 11B Distal
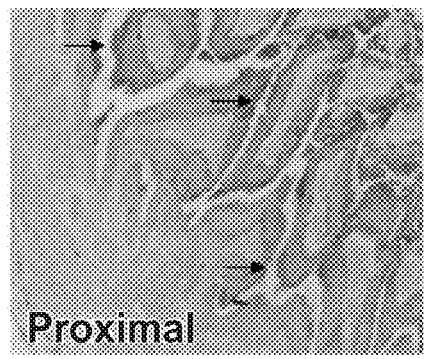
FIG. 11C Proximal
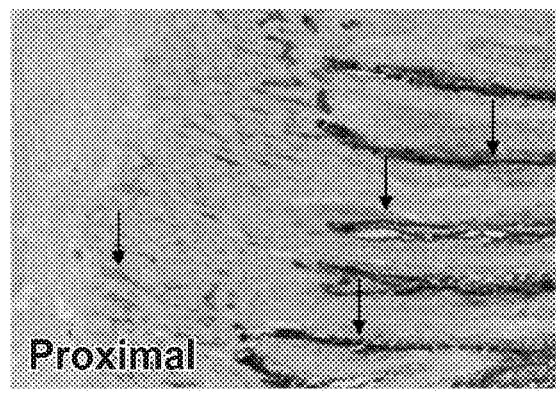
FIG. 11D Proximal

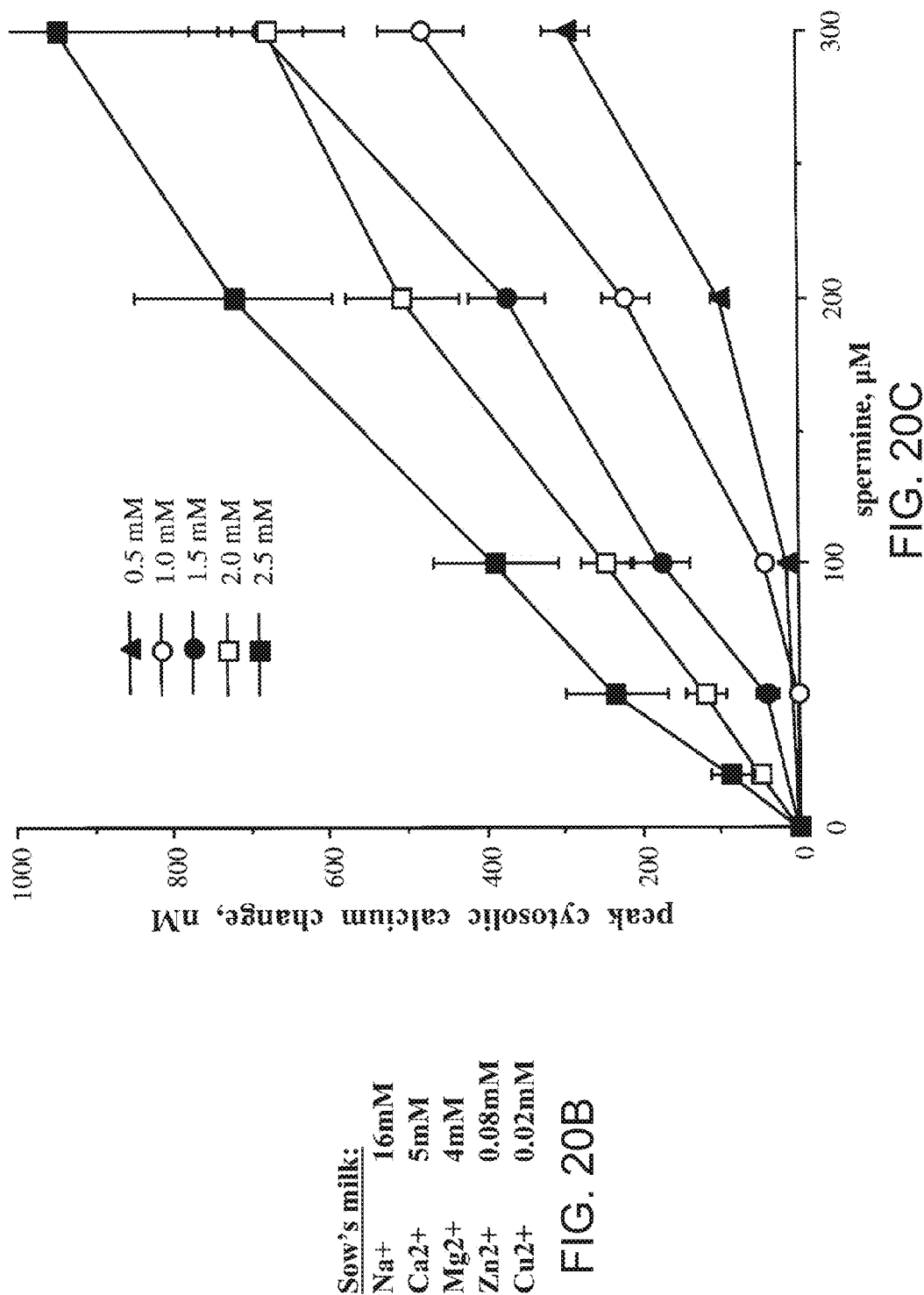

Spermine = S
Polymer: SSSSSSSSSSSSSSSSSSSSSSSSSSSSSS
Polymer after Hydrolysis:　S　S　SS　SSS　　SSSS
　　　　　　　　　　　　　SS　S　SSSSS　SSS　SS Lane Designations:

1) 2.5mM Ca++ - 3uM MC 0100

2) 1.5mM Ca++ - 0.0005% Bacitracin Zn
3) 2.5mM Ca++ - 0.0005% Bacitracin Zn – 3uM MC 0100
4) 2.5mM Ca++ - 0.005% Bacitracin Zn
5) 2.5mM Ca++ - 0.005% Bacitracin Zn – 3uM MC 0100

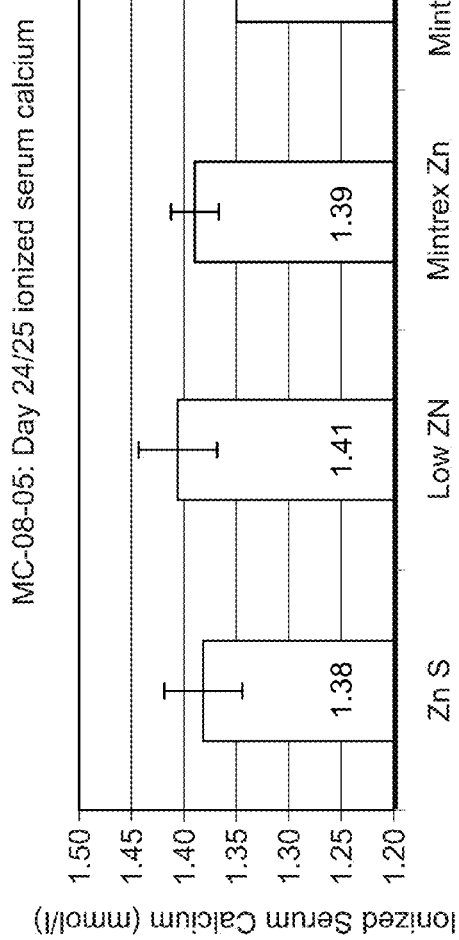
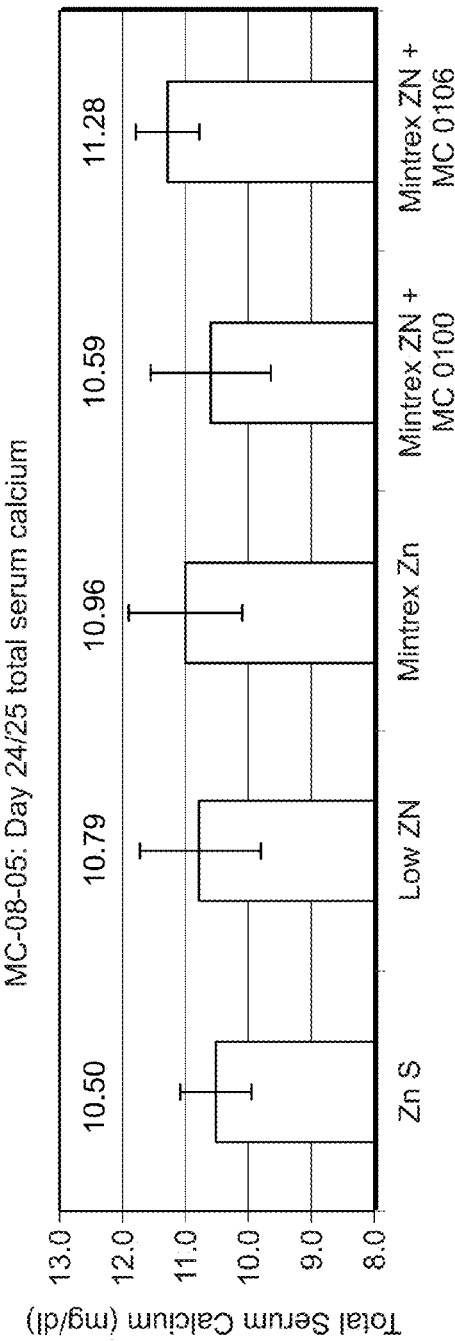
FIG. 45A
FIG. 45B

```
                       SEQUENCE LISTING

<160> NUMBER OF SEQ ID NOS: 10

<210> SEQ ID NO 1
<211> LENGTH: 5336
<212> TYPE: DNA
<213> ORGANISM: Gallus domesticus

<400> SEQUENCE: 1
aattcggcac gagggggcagc tgggggggccg gcgggggatg ctgccgccgc cctgcccagc      60
gccggagtaa gggcaagagc tggtggcggc aggagcggcc ccggcggcgg gacgagttct     120
tgaagatggg ctctctgtaa tgctttggtc atgaagaaac aaggaacact gaattgctgt     180
tttacaatgg agaaaacaga gggacaaata ccagcactgt ggcttccacc ttgttgctta     240
tctctctgca gacatgtgtc ccaaatgctc tctgggctgt attaaggaaa ggaaaagctt     300
agacattaca acatccgctt tcttacatcg tcttttccaa ttttacatcc tataacccct     360
tggtgaaagg aggaacaatg actttatata gctgctgttt gattcttttg ctgtttacct     420
ggaacactgc tgcctatggg ccaaaccaac gggcacagaa gaagggagac attattcttg     480
gaggattgtt ccccatccat tttggagtgg ctgctaaaga ccaggatcta aagtcaagac     540
ccgaatcagt ggagtgcata aggtataatt tccgaggctt ccgctggctc caggctatga     600
tctttgccat agaagaaata aataatagcc caaatctcct tcccaacatg accttgggat     660
acaggatatt tgacacttgc aatacagtct ctaaagccct tgaggccact ctgagttttg     720
tggcccagaa caagatagac tccttgaacc tggatgaatt ctgcaactgc tcagaacata     780 tccctttccac cattgcagtc gtgggggcaa ccggctctgg ggtttccacc gctgtggcca     840
atctgctggg actcttttac ataccctcagg tcagctatgc ctcatccagt cgtctcttga     900
gcaacaagaa ccagttcaag tccttcctcc gcacaatccc caatgacgag catcaggcca     960
```

```
ctgcgatggc agacatcatc gagtacttcc gctggaactg ggtgggaacg attgcagctg    1020
atgatgacta tggccggcca gggattgaaa agtttcggga ggaggcggag gagagagata    1080
tctgcattga ttttagtgag ctcatctccc agtactcaga tgaagaagag attcagcagg    1140
tggtggaggt catccagaac tccacagcac gagtgattgt ggttttctcc agtggaccag    1200
acctggaacc cctcatcaaa gagattgtca ggcgaaacat cactggaaag atctggctgg    1260
caagtgaagc ctgggccagt tcatccctga tagccatgcc agagttcttc cgtgtcatcg    1320
gcagcaccat tgggttttgca ctgaaggcag gccagatccc aggctttcgc gagttcctgc    1380
agaaggtgca tcccaaaaag tctgccaaca atggatttgc caaggagttt gggaagaga    1440 catttaactg ctatctcccc agtgagtcca aaaattctcc agcttcagct tccttccaca    1500
aggcccacga gagggcttg ggagctgaaa atggtacagc tgccttccga cctccatgca    1560
caggtgatga gaacatcacc agtgtggaaa caccgtacat ggacttcaca cacttgcgga    1620
tatcctataa tgtatatttg gcagtatatt ctattgctca cgctttgcag gatatatata    1680
cttgtacccc tgggaaagga ctcttcacca acgatcctg tgcagacatt aagaaggttg    1740
aggcatggca ggttctgaag cacctgcgcc acttaaattt caccagtaac atgggggagc    1800
aagtggactt tgatgagttt ggagacctgg tggggaatta ctcaataatc aactggcatc    1860
tctctccaga ggatggctca gtcgtctttg aggaggttgg gcactacaat gtgtatgcca    1920
agaaagggga gaggctcttt atcaatgaaa acaaaatcct gtggagtgga ttctcaaagg    1980 aggtgcccctt ctctaactgc agcagggact gcctgccagg caccaggaag gcattattg    2040 agggagagcc cacttgctgc ttcgagtgtg tggactgccc tgatggggag tacagtgatg    2100
aaacagatgc aagtgcttgt gacaagtgcc ctgaggatta ctggtctaat gagaaccaca    2160
catcctgcat ccccaagcag atagagtttc tatcctggac agagccctttt ggaatcgctt    2220 taactctctt tgctgtgctg ggaattttcc tgacttcttt tgtcctggga gtcttcacca    2280
aatttcgcaa cactcccatc gtcaaggcca caaaccggga gctgtcctac ctcctcctct    2340
tctccttgct ctgctgcttc tctagctcat tgttcttcat tggagagcca cagaactgga    2400
cttgccgtct gcggcagcca gcttttggca tcagcttgt cctctgcatc tcctgcatcc    2460
tggtgaaaac caatcgtgtc ctgcttgtct tcgaggcaaa gatccctaca agcctccacc    2520
gaaaatggtg gggcctcaac ctccagttcc tcctggtctt cttgtgcaca tttgtgcaga    2580
ttgtcatctg cgtgatttgg ctctacacgg ccccaccatc cagttatcga aaccatgagc    2640
tggaggatga gattatcttc atcacctgcc atgaaggctc cttgatggcc cttggcttcc    2700
tcattggcta cacctgtctc ctggcagcca tctgcttctt ctttgccttt aagtctcgaa    2760
aactgcctga acttcaat gaggccaagt tcatcacctt cagcatgctg atcttcttca    2820
ttgtctggat ctccttcatc cctgcttacg ccagcacata tggcaaattt gtctctgctg    2880
tggaggtgat tgcaatactg gctgccagtt tgggcttct ggcctgcatc ttctttaaca    2940
aagtctacat catcctcttc aagccttccc gcaaacacaat cgaggaggtg cgctgcagca    3000
cagctgccca cgcttttcaag gtggccgcca gggccacgct gagacgcagc aatgtgtcac    3060
gcaagcgttc caacagcctc ggaggttcca ccggttccac cccatcctcc tccatcagca    3120
gcaagagcaa ccatgaagac ccttttcctc taccggcttc tgctgagcgg cagcggcagc    3180
agcagcgtgg gtgcaagcag aaggtcagct ttgggagtgg tacggtcacc ttgtcactga    3240
gttttgagga gccacagaag aacgccatgg ccaacaggaa cgccagcgc aggaactccc    3300 tggaggccca gaacagcgat gacagcctga tgcggcacag ggccctgctc gctctacaga    3360
```

-continued

```
acagcgagtc cctcagtgcc gagcctggct tccagacagc atccagccca gagaccagtt    3420
cacaggagtc ggtagtggga gacaacaaag aagaggtacc aaaccctgag gcagagccct    3480
ccctgccgtc agctaactcc cgaaatttta taggcactgg aggcagctct gtcacagaaa    3540
acacagtaca ttcctaacaa agaaggtca tgaaaagcac ttccccagga ggaacttgct     3600
cacctcttgc ttctgaatgg gaaagacaac aaagatacat atctgtgaca cagtcccacc    3660
acacattgtt gctatcacca gcagggtaaa acacgtgcct ccagaggaaa gactaccaga    3720
agcctgtgtg tggggagcct caaactgaat ttgcagttgc tttactgaaa tcaggacacg    3780
tggggaggac aagtgaagat tgcctctggt ggggctttaa gtagaactct gcatattgtc    3840
ttgcctctgt aagcttttcc tgccagactg caactcagct gactatggga ggcactgagc    3900
aattccacta tactctgctt ttacatttat gtataatatt cctctttccc actatgtata    3960
atattccctc tttatccagt atatgtgatc tgtaaccacg tgcatcagga ctctcagctc    4020
ttcaaaagca agacacacgg tttcacttgg ggaaagcacg tcattggga aaataaaaaa     4080
gcccccaaca tcctgcatgc tgtgtacagc caagggtgtg aacatgtaaa gtatttaatg    4140
tgacagagca ccctgctatt tatatttagt aatgtcccaa tttctcctct ctgcccagca    4200
ggaaatactg gacaataccc ttcatagact ccattgcact agaccaagct actaggttcc    4260
tactggtttc ttccagcaga gtagctttta cctccagcct gcctgctttg gtggaagggg    4320
agaacaggtt gtaaatcccc ctggagattg ctgcgagagc acaatgagat gtattcgtga    4380
ttgattatgt cgctagtagt tgtatgctta acaaagtgtt gctgctgtaa tattccacat    4440
ggcatacgtg gctaaccctt ccacaccata gtcagtgttg tgctttgcca tattaatccg    4500
cctcataccc acacatagca ttgcgctggt tgtgacaata cttgtgggcc tgatacaaag    4560
ccaatgaaac aaggtgaaat ggagaaatag cccccaaatt tgataatatt tgagatgagt    4620
attgcaagtg tgcatggtgg tagaggatgg agtaaataaa acatacagag ttgggctctg    4680
agacgtgcaa acagacaaat gagtaaattg gatgtttggt tcctgtaggc cttcaagtag    4740
gttatgtccc tgttggccca tcttgaagag acagtaccta acaagaaga gtgcactgtg      4800
ccttggtgag agtaaggact tcaaaagaga gcacatcaga acttcattag tcttggctct    4860
tgttcagcac cccaaaagta gacataagtg ctcctgactg tgcacgatgt gcccggttcc    4920
tctgcattct gcgaatgttg aagtaagaga gtccttagaa cagatttctg ttgcagcctg    4980
aagaaagaaa gagtgacccct aggcaacttg gcaggaaggg caaggttatt ctgtagaatt    5040
tacttccctc ttcccagatc ccatatgcaa gaacaggtat ttgtcatgag gatatcagta    5100
cctgccctca tcacacacag aggcactcta gaccactgcg gaaaggtata taggcctgct    5160
acttattgtg aatggagatg aaaggactgt tgtgaatgtg atggggaaaa taccacaatt    5220
ctcttgttac tgtttttgct tggttgatgt tttgtgtttt tgtgtggttt tttctcgcc     5280
agagcaggaa aataaaactt acaggtgaca ttactgcaaa aaaaaaaaa aaaaac          5336
```

<210> SEQ ID NO 2
<211> LENGTH: 1059
<212> TYPE: PRT
<213> ORGANISM: Gallus domesticus

<400> SEQUENCE: 2

Met Thr Leu Tyr Ser Cys Cys Leu Ile Leu Leu Phe Thr Trp Asn
1               5                   10                  15

Thr Ala Ala Tyr Gly Pro Asn Gln Arg Ala Gln Lys Lys Gly Asp Ile

-continued

```
                    20                  25                  30
Ile Leu Gly Gly Leu Phe Pro Ile His Phe Gly Val Ala Ala Lys Asp
                35                  40                  45
Gln Asp Leu Lys Ser Arg Pro Glu Ser Val Glu Cys Ile Arg Tyr Asn
 50                  55                  60
Phe Arg Gly Phe Arg Trp Leu Gln Ala Met Ile Phe Ala Ile Glu Glu
 65                  70                  75                  80
Ile Asn Asn Ser Pro Asn Leu Leu Pro Asn Met Thr Leu Gly Tyr Arg
                 85                  90                  95
Ile Phe Asp Thr Cys Asn Thr Val Ser Lys Ala Leu Glu Ala Thr Leu
                100                 105                 110
Ser Phe Val Ala Gln Asn Lys Ile Asp Ser Leu Asn Leu Asp Glu Phe
                115                 120                 125
Cys Asn Cys Ser Glu His Ile Pro Ser Thr Ile Ala Val Val Gly Ala
                130                 135                 140
Thr Gly Ser Gly Val Ser Thr Ala Val Ala Asn Leu Leu Gly Leu Phe
145                 150                 155                 160
Tyr Ile Pro Gln Val Ser Tyr Ala Ser Ser Arg Leu Leu Ser Asn
                    165                 170                 175
Lys Asn Gln Phe Lys Ser Phe Leu Arg Thr Ile Pro Asn Asp Glu His
                180                 185                 190
Gln Ala Thr Ala Met Ala Asp Ile Ile Glu Tyr Phe Arg Trp Asn Trp
                195                 200                 205
Val Gly Thr Ile Ala Ala Asp Asp Tyr Gly Arg Pro Gly Ile Glu
                210                 215                 220
Lys Phe Arg Glu Glu Ala Glu Glu Arg Asp Ile Cys Ile Asp Phe Ser
225                 230                 235                 240
Glu Leu Ile Ser Gln Tyr Ser Asp Glu Glu Ile Gln Gln Val Val
                    245                 250                 255
Glu Val Ile Gln Asn Ser Thr Ala Arg Val Ile Val Phe Ser Ser
                260                 265                 270
Gly Pro Asp Leu Glu Pro Leu Ile Lys Glu Ile Val Arg Arg Asn Ile
                275                 280                 285
Thr Gly Lys Ile Trp Leu Ala Ser Glu Ala Trp Ala Ser Ser Ser Leu
                290                 295                 300
Ile Ala Met Pro Glu Phe Phe Arg Val Ile Gly Ser Thr Ile Gly Phe
305                 310                 315                 320
Ala Leu Lys Ala Gly Gln Ile Pro Gly Phe Arg Glu Phe Leu Gln Lys
                325                 330                 335
Val His Pro Lys Lys Ser Ala Asn Asn Gly Phe Ala Lys Glu Phe Trp
                340                 345                 350
Glu Glu Thr Phe Asn Cys Tyr Leu Pro Ser Glu Ser Lys Asn Ser Pro
                355                 360                 365
Ala Ser Ala Ser Phe His Lys Ala His Glu Glu Gly Leu Gly Ala Gly
                370                 375                 380
Asn Gly Thr Ala Ala Phe Arg Pro Pro Cys Thr Gly Asp Glu Asn Ile
385                 390                 395                 400
Thr Ser Val Glu Thr Pro Tyr Met Asp Phe Thr His Leu Arg Ile Ser
                    405                 410                 415
Tyr Asn Val Tyr Leu Ala Val Tyr Ser Ile Ala His Ala Leu Gln Asp
                420                 425                 430
Ile Tyr Thr Cys Thr Pro Gly Lys Gly Leu Phe Thr Asn Gly Ser Cys
                435                 440                 445
```

```
Ala Asp Ile Lys Lys Val Glu Ala Trp Gln Val Leu Lys His Leu Arg
    450                 455                 460
His Leu Asn Phe Thr Ser Asn Met Gly Glu Gln Val Asp Phe Asp Glu
465                 470                 475                 480
Phe Gly Asp Leu Val Gly Asn Tyr Ser Ile Ile Asn Trp His Leu Ser
                485                 490                 495
Pro Glu Asp Gly Ser Val Val Phe Glu Val Gly His Tyr Asn Val
                500                 505                 510
Tyr Ala Lys Lys Gly Glu Arg Leu Phe Ile Asn Glu Asn Lys Ile Leu
            515                 520                 525
Trp Ser Gly Phe Ser Lys Glu Val Pro Phe Ser Asn Cys Ser Arg Asp
    530                 535                 540
Cys Leu Pro Gly Thr Arg Lys Gly Ile Ile Glu Gly Glu Pro Thr Cys
545                 550                 555                 560
Cys Phe Glu Cys Val Asp Cys Pro Asp Gly Glu Tyr Ser Asp Glu Thr
                565                 570                 575
Asp Ala Ser Ala Cys Asp Lys Cys Pro Glu Asp Tyr Trp Ser Asn Glu
            580                 585                 590
Asn His Thr Ser Cys Ile Pro Lys Gln Ile Glu Phe Leu Ser Trp Thr
    595                 600                 605
Glu Pro Phe Gly Ile Ala Leu Thr Leu Phe Ala Val Leu Gly Ile Phe
    610                 615                 620
Leu Thr Ser Phe Val Leu Gly Val Phe Thr Lys Phe Arg Asn Thr Pro
625                 630                 635                 640
Ile Val Lys Ala Thr Asn Arg Glu Leu Ser Tyr Leu Leu Leu Phe Ser
                645                 650                 655
Leu Leu Cys Cys Phe Ser Ser Ser Leu Phe Phe Ile Gly Glu Pro Gln
                660                 665                 670
Asn Trp Thr Cys Arg Leu Arg Gln Pro Ala Phe Gly Ile Ser Phe Val
            675                 680                 685
Leu Cys Ile Ser Cys Ile Leu Val Lys Thr Asn Arg Val Leu Leu Val
    690                 695                 700
Phe Glu Ala Lys Ile Pro Thr Ser Leu His Arg Lys Trp Trp Gly Leu
705                 710                 715                 720
Asn Leu Gln Phe Leu Leu Val Phe Leu Cys Thr Phe Val Gln Ile Val
                725                 730                 735
Ile Cys Val Ile Trp Leu Tyr Thr Ala Pro Pro Ser Ser Tyr Arg Asn
            740                 745                 750
His Glu Leu Glu Asp Glu Ile Ile Phe Ile Thr Cys His Glu Gly Ser
    755                 760                 765
Leu Met Ala Leu Gly Phe Leu Ile Gly Tyr Thr Cys Leu Leu Ala Ala
    770                 775                 780
Ile Cys Phe Phe Phe Ala Phe Lys Ser Arg Lys Leu Pro Glu Asn Phe
785                 790                 795                 800
Asn Glu Ala Lys Phe Ile Thr Phe Ser Met Leu Ile Phe Phe Ile Val
                805                 810                 815
Trp Ile Ser Phe Ile Pro Ala Tyr Ala Ser Thr Tyr Gly Lys Phe Val
            820                 825                 830
Ser Ala Val Glu Val Ile Ala Ile Leu Ala Ala Ser Phe Gly Leu Leu
            835                 840                 845
Ala Cys Ile Phe Phe Asn Lys Val Tyr Ile Ile Leu Phe Lys Pro Ser
    850                 855                 860
```

-continued

```
Arg Asn Thr Ile Glu Glu Val Arg Cys Ser Thr Ala Ala His Ala Phe
865                 870                 875                 880

Lys Val Ala Ala Arg Ala Thr Leu Arg Arg Ser Asn Val Ser Arg Lys
            885                 890                 895

Arg Ser Asn Ser Leu Gly Gly Ser Thr Gly Ser Thr Pro Ser Ser Ser
        900                 905                 910

Ile Ser Ser Lys Ser Asn His Glu Asp Pro Phe Pro Leu Pro Ala Ser
            915                 920                 925

Ala Glu Arg Gln Arg Gln Gln Arg Gly Cys Lys Gln Lys Val Ser
        930                 935                 940

Phe Gly Ser Gly Thr Val Thr Leu Ser Leu Ser Phe Glu Glu Pro Gln
945                 950                 955                 960

Lys Asn Ala Met Ala Asn Arg Asn Ala Lys Arg Arg Asn Ser Leu Glu
            965                 970                 975

Ala Gln Asn Ser Asp Asp Ser Leu Met Arg His Arg Ala Leu Leu Ala
        980                 985                 990

Leu Gln Asn Ser Glu Ser Leu Ser Ala Glu Pro Gly Phe Gln Thr Ala
            995                 1000                1005

Ser Ser Pro Glu Thr Ser Ser Gln Glu Ser Val Val Gly Asp Asn Lys
    1010                1015                1020

Glu Glu Val Pro Asn Pro Glu Ala Glu Pro Ser Leu Pro Ser Ala Asn
1025                1030                1035                1040

Ser Arg Asn Phe Ile Gly Thr Gly Gly Ser Val Thr Glu Asn Thr
            1045                1050                1055

Val His Ser

<210> SEQ ID NO 3
<211> LENGTH: 1078
<212> TYPE: PRT
<213> ORGANISM: Homo sapiens

<400> SEQUENCE: 3

Met Ala Phe Tyr Ser Cys Cys Trp Val Leu Leu Ala Leu Thr Trp His
1               5                   10                  15

Thr Ser Ala Tyr Ser Pro Ser Gln Pro Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
            85                  90                  95

Ile Phe Asp Thr Cys Asn Thr Val Ser Lys Ala Leu Glu Ala Thr Leu
        100                 105                 110

Ser Phe Val Ala Gln Asn Lys Ile Asp Ser Leu Asn Leu Asp Glu Phe
    115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
            165                 170                 175
```

-continued

```
Lys Asn Gln Phe Lys Ser Phe Leu Arg Thr Ile Pro Asn Asp Glu His
                180                 185                 190
Cys Ala Thr Ala Met Ala Asp Ile Ile Glu Tyr Phe Arg Trp Asn Trp
            195                 200                 205
Val Gly Thr Ile Ala Ala Asp Asp Tyr Gly Arg Pro Gly Ile Glu
        210                 215                 220
Lys Phe Arg Glu Glu Ala Glu Arg Asp Ile Cys Ile Asp Phe Ser
225                 230                 235                 240
Glu Leu Ile Ser Gln Tyr Ser Asp Glu Glu Ile Gln Met Val Val
                245                 250                 255
Glu Val Ile Gln Asn Ser Thr Ala Lys Val Ile Val Phe Ser Ser
            260                 265                 270
Gly Pro Asp Leu Glu Pro Leu Ile Lys Glu Ile Val Pro Arg Asn Ile
        275                 280                 285
Thr Gly Lys Ile Trp Leu Ala Ser Glu Ala Trp Ala Ser Ser Ser Leu
        290                 295                 300
Ile Ala Met Pro Gln Tyr Phe His Val Val Gly Gly Thr Ile Gly Phe
305                 310                 315                 320
Ala Leu Lys Ala Gly Gln Ile Pro Gly Phe Arg Glu Phe Leu Lys Lys
                325                 330                 335
Val His Pro Pro Lys Ser Val Asn Asn Gly Phe Ala Lys Glu Phe Trp
            340                 345                 350
Glu Glu Thr Phe Met Cys His Leu Gln Glu Gly Ala Lys Gly Pro Leu
                355                 360                 365
Pro Val Asp Thr Phe Leu Ala Gly His Glu Glu Ser Gly Asp Arg Phe
        370                 375                 380
Ser Asn Ser Ser Thr Ala Phe Pro Pro Leu Cys Thr Gly Asp Glu Asn
385                 390                 395                 400
Ile Ser Ser Val Glu Thr Pro Tyr Ile Asp Tyr Thr Asn Leu Arg Ile
                405                 410                 415
Ser Tyr Asn Val Tyr Leu Ala Val Tyr Ser Ile Ala Asn Ala Leu Gln
            420                 425                 430
Asp Ile Tyr Thr Cys Leu Pro Gly Arg Gly Leu Phe Thr Asn Gly Ser
        435                 440                 445
Cys Ala Asp Ile Lys Lys Val Glu Ala Trp Gln Val Leu Lys His Leu
450                 455                 460
Arg Asn Leu Asn Phe Thr Asn Asn Met Gly Glu Gln Val Thr Phe Asp
465                 470                 475                 480
Glu Cys Gly Asp Leu Val Gly Asn Tyr Ser Ile Ile Asn Trp His Leu
                485                 490                 495
Ser Pro Glu Asp Gly Ser Ile Val Phe Lys Glu Val Gly Tyr Tyr Asn
            500                 505                 510
Val Tyr Ala Lys Lys Gly Glu Arg Leu Phe Ile Asn Glu Glu Lys Ile
        515                 520                 525
Leu Trp Ser Gly Phe Ser Arg Glu Val Pro Phe Ser Asn Cys Ser Arg
        530                 535                 540
Asp Cys Leu Ala Gly Thr Arg Lys Gly Ile Ile Glu Gly Glu Pro Thr
545                 550                 555                 560
Cys Cys Phe Glu Cys Val Glu Cys Pro Asp Gly Glu Tyr Ser Asp Glu
                565                 570                 575
Thr Asp Ala Ser Ala Cys Asn Lys Cys Pro Asp Asp Phe Trp Ser Asn
            580                 585                 590
Glu Asn His Thr Ser Cys Ile Ala Lys Glu Ile Glu Phe Leu Ser Trp
```

```
                595                 600                 605
Thr Glu Pro Phe Gly Ile Ala Leu Thr Leu Phe Ala Val Leu Gly Ile
610                 615                 620

Ser Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Leu Phe Phe Ile Gly Glu Pro
            660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe Met Phe Lys Trp Trp Gly
705                 710                 715                 720

Leu Asn Leu Gln Phe Leu Leu Val Phe Leu Cys Thr Phe Asn Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys Asn Glu Gly
            755                 760                 765

Ser Leu Met Ala Leu Gly Phe Leu Ile Gly Tyr Thr Cys Leu Leu Ala
770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
            835                 840                 845

Leu Ala Cys Ile Phe Phe Asn Lys Ile Tyr Ile Ile Leu Phe Lys Pro
850                 855                 860

Ser Arg Asn Thr Ile Glu Glu Val Arg Cys Ser Thr Ala Ala Asn Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Arg Pro Glu
            915                 920                 925

Arg Gln Lys Gln Gln Pro Leu Ala Leu Thr Gln Glu Gln Gln
930                 935                 940

Gln Gln Pro Leu Thr Leu Pro Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala Asn Arg Asn Ser
            980                 985                 990

Thr Asn Gln Asn Ser Leu Glu Ala Gln Lys Ser Ser Asp Thr Leu Thr
            995                 1000                1005

Ala Asn Gln Pro Leu Leu Pro Leu Gln Cys Gly Glu Thr Asp Leu Asp
1010                1015                1020
```

```
Leu Thr Val Gln Glu Thr Gly Leu Gln Gly Pro Val Gly Gly Asp Gln
1025                1030                1035                1040

Arg Pro Glu Val Glu Asp Pro Glu Glu Leu Ser Pro Ala Leu Val Val
                1045                1050                1055

Ser Ser Ser Gln Ser Phe Val Ile Ser Gly Gly Ser Thr Val Thr
            1060                1065                1070

Glu Asn Val Val Asn Ser
        1075

<210> SEQ ID NO 4
<211> LENGTH: 1045
<212> TYPE: PRT
<213> ORGANISM: Gallus domesticus

<400> SEQUENCE: 4

Met Thr Leu Tyr Ser Cys Cys Leu Ile Leu Leu Phe Thr Trp Asn
 1               5                   10                  15

Thr Ala Ala Tyr Gly Pro Asn Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Ser Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Asn Ser Pro Asn Leu Leu Pro Asn Met Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Arg Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
290                 295                 300

Ile Ala Met Pro Glu Phe Phe Arg Val Ile Gly Ser Thr Ile Gly Phe
```

```
              305                 310                 315                 320
            Ala Leu Lys Ala Gly Gln Ile Pro Gly Phe Arg Glu Phe Leu Gln Lys
                            325                 330                 335

Val His Pro Lys Lys Ser Ala Asn Asn Gly Phe Ala Lys Glu Phe Trp
                            340                 345                 350

Glu Glu Thr Phe Asn Cys Tyr Leu Pro Ser Glu Ser Lys Asn Ser Pro
                            355                 360                 365

Ala Ser Ala Ser Phe His Lys Ala His Glu Gly Leu Gly Ala Gly
                            370                 375             380

Asn Gly Thr Ala Ala Phe Arg Pro Pro Cys Thr Gly Asp Glu Asn Ile
            385                 390                 395                 400

Thr Ser Val Glu Thr Pro Tyr Met Asp Phe Thr His Leu Arg Ile Ser
                            405                 410                 415

Tyr Asn Val Tyr Leu Ala Val Tyr Ser Ile Ala His Ala Leu Gln Asp
                            420                 425                 430

Ile Tyr Thr Cys Thr Pro Gly Lys Gly Leu Phe Thr Asn Gly Ser Cys
                            435                 440                 445

Ala Asp Ile Lys Lys Val Glu Ala Trp Gln Val Leu Lys His Leu Arg
                            450                 455                 460

Met Leu Asn Phe Thr Ser Asn Met Gly Glu Gln Val Asp Phe Asp Glu
            465                 470                 475                 480

Phe Gly Asp Leu Val Gly Asn Tyr Ser Ile Ile Asn Trp His Leu Ser
                            485                 490                 495

Pro Glu Asp Gly Ser Val Val Phe Glu Glu Val Gly His Tyr Asn Val
                            500                 505                 510

Tyr Ala Lys Lys Gly Glu Arg Leu Phe Ile Asn Glu Asn Lys Ile Leu
                            515                 520                 525

Trp Ser Gly Phe Ser Lys Glu Val Pro Phe Ser Asn Cys Ser Arg Asp
                            530                 535                 540

Cys Leu Pro Gly Thr Arg Lys Gly Ile Ile Glu Gly Glu Pro Thr Cys
            545                 550                 555                 560

Cys Phe Glu Cys Val Asp Cys Pro Asp Gly Glu Tyr Ser Asp Glu Thr
                            565                 570                 575

Asp Ala Ser Ala Cys Asp Lys Cys Pro Glu Asp Tyr Trp Ser Asn Glu
                            580                 585                 590

Asn His Thr Ser Cys Ile Pro Lys Gln Ile Glu Phe Leu Ser Trp Thr
                            595                 600                 605

Glu Pro Phe Gly Ile Ala Leu Thr Leu Phe Ala Val Leu Gly Ile Phe
                            610                 615                 620

Leu Thr Ser Phe Val Leu Gly Val Phe Thr Lys Phe Arg Asn Thr Pro
            625                 630                 635                 640

Ile Val Lys Ala Thr Asn Arg Glu Leu Ser Tyr Leu Leu Leu Phe Ser
                            645                 650                 655

Leu Leu Cys Cys Phe Ser Ser Ser Leu Phe Phe Ile Gly Glu Pro Gln
                            660                 665                 670

Asn Trp Thr Cys Arg Leu Arg Gln Pro Ala Phe Gly Ile Ser Phe Val
                            675                 680                 685

Leu Cys Ile Ser Cys Ile Leu Val Lys Thr Asn Arg Val Leu Leu Val
                            690                 695                 700

Phe Glu Ala Lys Ile Pro Thr Ser Leu His Arg Lys Trp Trp Gly Leu
            705                 710                 715                 720

Asn Leu Gln Phe Leu Leu Val Phe Leu Cys Thr Phe Val Gln Ile Val
                            725                 730                 735
```

```
Ile Cys Val Ile Trp Leu Tyr Thr Ala Pro Ser Ser Tyr Arg Asn
            740                 745                 750

His Glu Leu Glu Asp Glu Ile Phe Ile Thr Cys Asn Glu Gly Ser
            755                 760                 765

Leu Met Ala Leu Gly Phe Leu Ile Gly Tyr Thr Cys Leu Leu Ala Ala
    770                 775                 780

Ile Cys Phe Phe Phe Ala Phe Lys Ser Arg Lys Leu Pro Glu Asn Phe
785                 790                 795                 800

Asn Glu Ala Lys Phe Ile Thr Phe Ser Met Leu Ile Phe Phe Ile Val
                805                 810                 815

Trp Ile Ser Phe Ile Pro Ala Tyr Ala Ser Thr Tyr Gly Lys Phe Val
                820                 825                 830

Ser Ala Val Glu Val Ile Ala Ile Leu Ala Ala Ser Phe Gly Leu Leu
                835                 840                 845

Ala Cys Ile Phe Phe Asn Lys Val Tyr Ile Ile Leu Phe Lys Pro Ser
850                 855                 860

Arg Asn Thr Ile Glu Glu Val Arg Cys Ser Thr Ala Ala His Ala Phe
865                 870                 875                 880

Lys Val Ala Ala Arg Ala Thr Leu Arg Arg Ser Asn Val Ser Arg Lys
                885                 890                 895

Arg Ser Asn Ser Leu Gly Gly Ser Thr Gly Ser Thr Pro Ser Ser Ser
                900                 905                 910

Ile Ser Ser Lys Ser Asn His Glu Asp Pro Phe Pro Leu Pro Ala Ser
            915                 920                 925

Ala Glu Arg Gln Arg Gln Gln Arg Gly Cys Lys Gln Lys Val Ser
            930                 935                 940

Phe Gly Ser Gly Thr Val Thr Leu Ser Leu Ser Phe Glu Glu Pro Gln
945                 950                 955                 960

Lys Asn Ala Asn Ala Asn Arg Asn Ala Lys Arg Arg Asn Ser Leu Glu
                965                 970                 975

Ala Gln Asn Ser Asp Asp Ser Leu Met Arg His Arg Ala Leu Leu Ala
                980                 985                 990

Leu Gln Asn Ser Glu Ser Leu Ser Ala Glu Pro Gly Phe Gln Thr Ala
            995                 1000                1005

Ser Ser Pro Glu Thr Ser Ser Gln Glu Ser Val Val Gly Asp Asn Lys
    1010                1015                1020

Glu Glu Val Pro Asn Pro Ser Gly Thr Gly Gly Ser Ser Val Thr Glu
1025                1030                1035                1040

Asn Thr Val Met Ser
                1045

<210> SEQ ID NO 5
<211> LENGTH: 941
<212> TYPE: PRT
<213> ORGANISM: Salmo salar

<400> SEQUENCE: 5

Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
```

```
              50                  55                  60
Phe Arg Gly Phe Arg Trp Leu Gln Ala Met Ile Phe Ala Ile Glu Glu
 65                  70                  75                  80

Ile Asn Asn Ser Ser Thr Leu Leu Pro Asn Ile Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
            115                 120                 125

Cys Asn Cys Thr Asp His Ile Pro Ser Thr Ile Ala Val Val Gly Ala
            130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Arg Leu Leu Ser Asn
                165                 170                 175

Lys Asn Gln Phe Lys Ser Phe Met Arg Thr Ile Pro Thr Asp Glu His
                180                 185                 190

Gln Ala Thr Ala Met Ala Asp Ile Ile Asp Tyr Phe Gln Trp Asn Trp
                195                 200                 205

Val Ile Ala Val Ala Ser Asp Asp Glu Tyr Gly Arg Pro Gly Ile Glu
210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
                245                 250                 255

Asp Arg Ile Glu Asn Ser Ser Ala Lys Val Ile Val Phe Ala Ser
                260                 265                 270

Gly Pro Asp Ile Glu Pro Leu Ile Lys Glu Met Val Arg Arg Asn Ile
            275                 280                 285

Thr Asp Arg Ile Trp Leu Ala Ser Glu Ala Trp Ala Thr Thr Ser Leu
            290                 295                 300

Ile Ala Lys Pro Glu Tyr Leu Asp Val Val Gly Thr Ile Gly Phe
305                 310                 315                 320

Ala Leu Arg Ala Gly Glu Ile Pro Gly Phe Lys Asp Phe Leu Gln Glu
                325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
            355                 360                 365

Ser Glu Asn Gly Ser Thr Ser Phe Arg Pro Leu Cys Thr Gly Glu Glu
            370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
                405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
            435                 440                 445

Leu Arg His Leu Asn Phe Ser Asn Ser Met Gly Glu Lys Val His Phe
            450                 455                 460

Asp Glu Asn Ala Asp Pro Ser Gly Asn Tyr Thr Ile Ile Asn Trp His
465                 470                 475                 480
```

```
Arg Ser Pro Glu Asp Gly Ser Val Val Phe Glu Val Gly Phe Tyr
            485                 490                 495
Asn Met Arg Ala Lys Arg Gly Val Gln Leu Phe Ile Asp Asn Thr Lys
        500                 505                 510
Ile Leu Trp Asn Gly Tyr Asn Thr Glu Val Pro Phe Ser Asn Cys Ser
    515                 520                 525
Glu Asp Cys Glu Pro Gly Thr Arg Lys Gly Ile Ile Glu Ser Met Pro
530                 535                 540
Thr Cys Cys Phe Glu Cys Thr Glu Cys Ser Glu Gly Glu Tyr Ser Asp
545                 550                 555                 560
His Lys Asp Ala Ser Val Cys Thr Lys Cys Pro Asn Asp Ser Trp Ser
                565                 570                 575
Asn Glu Asn His Thr Ser Cys Phe Leu Lys Glu Ile Glu Phe Leu Ser
            580                 585                 590
Trp Thr Glu Pro Phe Gly Ile Ala Leu Ala Leu Cys Ser Val Leu Gly
        595                 600                 605
Val Phe Leu Thr Ala Phe Val Met Gly Val Phe Ile Lys Phe Arg Asn
    610                 615                 620
Thr Pro Ile Val Lys Ala Thr Asn Arg Glu Leu Ser Tyr Leu Leu Leu
625                 630                 635                 640
Phe Ser Leu Ile Cys Cys Phe Ser Ser Ser Leu Ile Phe Ile Gly Glu
                645                 650                 655
Pro Gln Asp Trp Thr Cys Arg Leu Arg Gln Pro Ala Phe Gly Ile Ser
            660                 665                 670
Phe Val Leu Cys Ile Ser Cys Ile Leu Val Lys Thr Asn Arg Val Leu
        675                 680                 685
Leu Val Phe Glu Ala Lys Ile Pro Thr Ser Leu His Arg Lys Trp Trp
    690                 695                 700
Gly Leu Asn Leu Gln Phe Leu Leu Val Phe Leu Phe Thr Phe Val Gln
705                 710                 715                 720
Val Met Ile Cys Val Val Trp Leu Tyr Asn Ala Pro Pro Ala Ser Tyr
                725                 730                 735
Arg Asn His Asp Ile Asp Glu Ile Ile Phe Ile Thr Cys Asn Glu Gly
            740                 745                 750
Ser Met Met Ala Leu Gly Phe Leu Ile Gly Tyr Thr Cys Leu Leu Ala
        755                 760                 765
Ala Ile Cys Phe Phe Phe Ala Phe Lys Ser Arg Lys Leu Pro Glu Asn
    770                 775                 780
Phe Thr Glu Ala Lys Phe Ile Thr Phe Ser Met Leu Ile Phe Phe Ile
785                 790                 795                 800
Val Trp Ile Ser Phe Ile Pro Ala Tyr Phe Ser Thr Tyr Gly Lys Phe
                805                 810                 815
Val Ser Ala Val Glu Val Ile Ala Ile Leu Ala Ser Ser Phe Gly Leu
            820                 825                 830
Leu Ala Cys Ile Phe Phe Asn Lys Val Tyr Ile Ile Leu Phe Lys Pro
        835                 840                 845
Ser Arg Asn Thr Ile Glu Glu Val Arg Cys Ser Thr Ala Ala His Ser
    850                 855                 860
Phe Lys Val Ala Ala Lys Ala Thr Leu Arg His Ser Ala Ser Ala Arg
865                 870                 875                 880
Lys Arg Ser Ser Ser Val Gly Gly Ser Cys Ala Ser Thr Pro Ser Ser
                885                 890                 895
```

-continued

```
Ser Ile Ser Leu Lys Thr Asn Asp Asn Asp Ser Pro Ser Gly Gln Gln
            900                 905                 910

Arg Ile His Lys Pro Arg Val Ser Phe Gly Ser Gly Thr Val Thr Leu
            915                 920                 925

Ser Leu Ser Phe Glu Glu Ser Arg Lys Asn Ser Met Lys
            930                 935                 940

<210> SEQ ID NO 6
<211> LENGTH: 944
<212> TYPE: PRT
<213> ORGANISM: Gadus morha

<400> SEQUENCE: 6

Met Ala Phe Leu Leu Gly Tyr Tyr Leu Leu Leu Gly Ser Val Gln
 1               5                  10                  15

Leu Thr Ser Thr Tyr Gly Pro Tyr Gln Arg Ala Gln Lys Thr Gly Asp
            20                  25                  30

Ile Leu Leu Gly Gly Leu Phe Pro Ile His Phe Gly Val Ala Ser Lys
            35                  40                  45

Asp Gln Asp Leu Ala Ala Arg Pro Glu Ser Thr Gln Cys Val Arg Tyr
            50                  55                  60

Asn Phe Arg Gly Phe Arg Trp Leu Gln Ala Met Ile Phe Ala Ile Asp
 65                  70                  75                  80

Glu Ile Asn Asn Ser Ser Ser Leu Leu Pro Asn Ile Thr Leu Gly Tyr
                85                  90                  95

Arg Ile Tyr Asp Thr Cys Asn Thr Val Ser Lys Ala Leu Glu Ala Thr
            100                 105                 110

Leu Ser Phe Val Ala Gln Asn Lys Met Asp Ser Ile Asn Leu Asp Glu
            115                 120                 125

Phe Cys Asn Cys Thr Asp His Ile Pro Ser Thr Ile Ala Val Val Gly
        130                 135                 140

Ala Ser Gly Ser Ala Val Ser Thr Ala Val Ala Asn Leu Leu Ser Leu
145                 150                 155                 160

Phe Tyr Ile Pro Gln Ile Ser Tyr Ala Ser Ser Ser Arg Leu Leu Ser
                165                 170                 175

Asn Lys Asn Gln Tyr Lys Ser Phe Met Arg Thr Ile Pro Thr Asp Glu
            180                 185                 190

Tyr Gln Ala Thr Ala Met Ala Asp Ile Ile Ala Tyr Phe Gln Trp Asn
            195                 200                 205

Trp Val Ile Ala Val Ala Ser Asp Asp Glu Tyr Gly Arg Pro Gly Ile
        210                 215                 220

Glu Lys Phe Glu Lys Glu Met Glu Glu Arg Asp Ile Cys Ile His Leu
225                 230                 235                 240

Asn Glu Phe Ile Ser Gln Tyr Phe Glu Asp His Glu Ile Gln Ala Leu
                245                 250                 255

Val Asp Arg Ile Glu Asn Ser Thr Ala Lys Val Ile Val Phe Ala
            260                 265                 270

Ser Gly Pro Asp Val Glu Pro Leu Ile Lys Glu Met Ala Arg Arg Asn
            275                 280                 285

Ile Thr Asp Arg Leu Trp Leu Ala Ser Glu Ala Trp Ala Ser Ser Ser
        290                 295                 300

Leu Ile Ala Lys Pro Glu Tyr Leu Asp Val Met Ala Gly Thr Ile Gly
305                 310                 315                 320

Phe Ala Leu Arg Pro Gly His Ile Pro Gly Phe Lys Glu Phe Leu Gln
                325                 330                 335
```

```
Gln Val Gln Pro Lys Val Ser His Asn Glu Phe Ile Arg Glu Phe
            340                 345                 350
Trp Glu Glu Thr Phe Asn Cys Tyr Leu Glu Asp Ser Leu Arg Leu Gln
            355                 360                 365
Glu Ser Glu Asn Gly Thr Glu Ser Ser Arg Pro Leu Cys Ser Gly Asp
            370                 375                 380
Glu Asp Ile Thr Ser Ala Glu Thr Pro Tyr Leu Asp Tyr Thr His Leu
385                 390                 395                 400
Arg Ile Ser Tyr Asn Val Tyr Val Ala Val Tyr Ser Ile Ala Gln Ala
                405                 410                 415
Leu Gln Asp Ile Leu Thr Cys Thr Pro Gly Arg Gly Leu Phe Ala Asn
            420                 425                 430
Ser Ser Cys Ala Asp Thr Lys Asp Met Glu Ala Trp Gln Val Leu Lys
            435                 440                 445
Gln Leu Arg His Leu Asp Tyr Ile Asp Ser Ile Gly Glu Lys Val His
            450                 455                 460
Phe Asp Glu Asn Ala Glu Met Trp Gly Asn Tyr Thr Ile Ile Asn Trp
465                 470                 475                 480
His Arg Ser Thr Glu Asp Ala Ser Val Val Phe Glu Glu Ile Gly Tyr
                485                 490                 495
Tyr Asn Met His Ile Lys Lys Gly Ser Lys Leu Tyr Ile Asp Asn Ala
                500                 505                 510
Lys Ile Leu Trp Asn Gly Tyr Ser Thr Glu Leu Pro Phe Ser Asn Cys
            515                 520                 525
Ser Glu Asp Cys Asp Pro Gly Thr Arg Lys Gly Ile Ile Asp Ser Glu
            530                 535                 540
Pro Thr Cys Cys Phe Glu Cys Lys Glu Cys Ser Asp Gly Glu Tyr Ser
545                 550                 555                 560
Asn His Lys Asp Ala Ser Val Cys Thr Lys Cys Pro Asn Asn Ser Trp
                565                 570                 575
Ser Asn Gly Asn His Thr Phe Cys Phe Leu Lys Glu Ile Glu Phe Leu
            580                 585                 590
Ala Trp Thr Glu Pro Phe Gly Ile Ala Leu Thr Ile Phe Ala Val Leu
            595                 600                 605
Gly Val Leu Leu Thr Ala Phe Val Leu Gly Val Phe Ala Arg Phe Arg
            610                 615                 620
Asn Thr Pro Ile Val Lys Ala Thr Asn Arg Glu Leu Ser Tyr Leu Leu
625                 630                 635                 640
Leu Phe Ser Leu Val Cys Cys Phe Ser Ser Ser Leu Met Phe Ile Gly
                645                 650                 655
Glu Pro Gln Asp Trp Thr Cys Arg Leu Arg Gln Pro Ala Phe Gly Ile
            660                 665                 670
Ser Phe Val Leu Cys Ile Ser Cys Ile Leu Val Lys Thr Asn Arg Val
            675                 680                 685
Leu Leu Val Phe Glu Ala Lys Ile Pro Thr Ser Leu His Arg Lys Trp
            690                 695                 700
Trp Gly Leu Asn Leu Gln Phe Leu Leu Val Phe Leu Cys Thr Phe Val
705                 710                 715                 720
Gln Val Met Ile Cys Val Val Trp Leu Tyr Asn Ala Pro Pro Ala Ser
                725                 730                 735
Ser Lys Asn His Asp Ile Asp Glu Ile Ile Phe Ile Thr Cys Asn Glu
            740                 745                 750
```

```
Gly Ser Met Met Ala Leu Gly Phe Leu Ile Gly Tyr Thr Cys Leu Leu
            755                 760                 765

Ala Ala Ile Cys Phe Phe Phe Ala Phe Lys Ser Arg Lys Leu Pro Glu
        770                 775                 780

Asn Phe Thr Glu Ala Lys Phe Ile Thr Phe Ser Met Leu Ile Phe Phe
785                 790                 795                 800

Ile Val Trp Ile Ser Phe Ile Pro Ala Tyr Phe Ser Thr Tyr Gly Lys
                    805                 810                 815

Phe Val Ser Ala Val Glu Val Ile Ala Ile Leu Ala Ser Ser Phe Gly
                820                 825                 830

Leu Leu Ala Cys Leu Phe Phe His Lys Val Tyr Ile Ile Leu Phe Lys
            835                 840                 845

Pro Ser Arg Asn Thr Ile Glu Glu Val Arg Cys Ser Thr Ala Ala His
        850                 855                 860

Ala Phe Lys Val Ala Ala Lys Ala Thr Leu Lys His Asn Thr Ala Ser
865                 870                 875                 880

Arg Lys Arg Ser Gly Ser Asn Gly Gly Ser Gly Ser Ser Pro Ser
                    885                 890                 895

Ser Ser Ile Ser Leu Lys Thr Asn Gly Asn Asp Cys Gly Pro Ser Ala
                900                 905                 910

Gly Gln Pro Arg Ile His Arg Pro Arg Val Ser Phe Gly Ser Gly Thr
            915                 920                 925

Val Thr Leu Ser Leu Ser Phe Asp Glu Ser Arg Arg Ser Ser Val Met
        930                 935                 940

<210> SEQ ID NO 7
<211> LENGTH: 1027
<212> TYPE: PRT
<213> ORGANISM: Squalus acanthias

<400> SEQUENCE: 7

Met Ala Gln Leu His Cys Gln Leu Leu Phe Leu Gly Phe Thr Leu Leu
1               5                   10                  15

Gln Ser Tyr Asn Val Ser Gly Tyr Gly Pro Asn Gln Arg Ala Gln Lys
            20                  25                  30

Lys Gly Asp Ile Ile Leu Gly Gly Leu Phe Pro Ile His Phe Gly Val
        35                  40                  45

Ala Ala Lys Asp Gln Asp Leu Lys Ser Arg Pro Glu Ala Thr Lys Cys
    50                  55                  60

Ile Arg Tyr Asn Phe Arg Gly Phe Arg Trp Leu Gln Ala Met Ile Phe
65                  70                  75                  80

Ala Ile Glu Glu Ile Asn Asn Ser Met Thr Phe Leu Pro Asn Ile Thr
                85                  90                  95

Leu Gly Tyr Arg Ile Phe Asp Thr Cys Asn Thr Val Ser Lys Ala Leu
            100                 105                 110

Glu Ala Thr Leu Ser Phe Val Ala Gln Asn Lys Ile Asp Ser Leu Asn
        115                 120                 125

Leu Asp Glu Phe Cys Asn Cys Ser Asp His Ile Pro Ser Thr Ile Ala
    130                 135                 140

Val Val Gly Ala Thr Gly Ser Gly Ile Ser Thr Ala Val Ala Asn Leu
145                 150                 155                 160

Leu Gly Leu Phe Tyr Ile Pro Gln Val Ser Tyr Ala Ser Ser Ser Arg
                165                 170                 175

Leu Leu Ser Asn Lys Asn Glu Tyr Lys Ala Phe Leu Arg Thr Ile Pro
            180                 185                 190
```

```
Asn Asp Glu Gln Gln Ala Thr Ala Met Ala Glu Ile Ile Glu His Phe
            195                 200                 205

Gln Trp Asn Trp Val Gly Thr Leu Ala Ala Asp Asp Tyr Gly Arg
    210                 215                 220

Pro Gly Ile Asp Lys Phe Arg Glu Ala Val Lys Arg Asp Ile Cys
225                 230                 235                 240

Ile Asp Phe Ser Glu Met Ile Ser Gln Tyr Tyr Thr Gln Lys Gln Leu
                245                 250                 255

Glu Phe Ile Ala Asp Val Ile Gln Asn Ser Ser Ala Lys Val Ile Val
                260                 265                 270

Val Phe Ser Asn Gly Pro Asp Leu Glu Pro Leu Ile Gln Glu Ile Val
            275                 280                 285

Arg Arg Asn Ile Thr Asp Arg Ile Trp Leu Ala Ser Glu Ala Trp Ala
            290                 295                 300

Ser Ser Ser Leu Ile Ala Lys Pro Glu Tyr Phe His Val Val Gly Gly
305                 310                 315                 320

Thr Ile Gly Phe Ala Leu Arg Ala Gly Arg Ile Pro Gly Phe Asn Lys
                325                 330                 335

Phe Leu Lys Glu Val His Pro Ser Arg Ser Ser Asp Asn Gly Phe Val
            340                 345                 350

Lys Glu Phe Trp Glu Glu Thr Phe Asn Cys Tyr Phe Thr Glu Lys Thr
            355                 360                 365

Leu Thr Gln Leu Lys Asn Ser Lys Val Pro Ser His Gly Pro Ala Ala
    370                 375                 380

Gln Gly Asp Gly Ser Lys Ala Gly Asn Ser Arg Arg Thr Ala Leu Arg
385                 390                 395                 400

His Pro Cys Thr Gly Glu Glu Asn Ile Thr Ser Val Glu Thr Pro Tyr
                405                 410                 415

Leu Asp Tyr Thr His Leu Arg Ile Ser Tyr Asn Val Tyr Val Ala Val
                420                 425                 430

Tyr Ser Ile Ala His Ala Leu Gln Asp Ile His Ser Cys Lys Pro Gly
            435                 440                 445

Thr Gly Ile Phe Ala Asn Gly Ser Cys Ala Asp Ile Lys Lys Val Glu
    450                 455                 460

Ala Trp Gln Val Leu Asn His Leu Leu His Leu Lys Phe Thr Asn Ser
465                 470                 475                 480

Met Gly Glu Gln Val Asp Phe Asp Gln Gly Asp Leu Lys Gly Asn
                485                 490                 495

Tyr Thr Ile Ile Asn Trp Gln Leu Ser Ala Glu Asp Glu Ser Val Leu
                500                 505                 510

Phe His Glu Val Gly Asn Tyr Asn Ala Tyr Ala Lys Pro Ser Asp Arg
    515                 520                 525

Leu Asn Ile Asn Glu Lys Lys Ile Leu Trp Ser Gly Phe Ser Lys Val
    530                 535                 540

Val Pro Phe Ser Asn Cys Ser Arg Asp Cys Val Pro Gly Thr Arg Lys
545                 550                 555                 560

Gly Ile Ile Glu Gly Glu Pro Thr Cys Cys Phe Glu Cys Met Ala Cys
                565                 570                 575

Ala Glu Gly Glu Phe Ser Asp Glu Asn Asp Ala Ser Ala Cys Thr Lys
            580                 585                 590

Cys Pro Asn Asp Phe Trp Ser Asn Glu Asn His Thr Ser Cys Ile Ala
            595                 600                 605
```

```
Lys Glu Ile Glu Tyr Leu Ser Trp Thr Glu Pro Phe Gly Ile Ala Leu
610                 615                 620
Thr Ile Phe Ala Val Leu Gly Ile Leu Ile Thr Ser Phe Val Leu Gly
625                 630                 635                 640
Val Phe Ile Lys Phe Arg Asn Thr Pro Ile Val Lys Ala Thr Asn Arg
            645                 650                 655
Glu Leu Ser Tyr Leu Leu Leu Phe Ser Leu Ile Cys Cys Phe Ser Ser
            660                 665                 670
Ser Leu Ile Phe Ile Gly Glu Pro Arg Asp Trp Thr Cys Arg Leu Arg
            675                 680                 685
Gln Pro Ala Phe Gly Ile Ser Phe Val Leu Cys Ile Ser Cys Ile Leu
690                 695                 700
Val Lys Thr Asn Arg Val Leu Leu Val Phe Glu Ala Lys Ile Pro Thr
705                 710                 715                 720
Ser Leu His Arg Lys Trp Val Gly Leu Asn Leu Gln Phe Leu Leu Val
            725                 730                 735
Phe Leu Cys Ile Leu Val Gln Ile Val Thr Cys Ile Ile Trp Leu Tyr
            740                 745                 750
Thr Ala Pro Pro Ser Ser Tyr Arg Asn His Glu Leu Glu Asp Glu Val
755                 760                 765
Ile Phe Ile Thr Cys Asp Glu Gly Ser Leu Met Ala Leu Gly Phe Leu
770                 775                 780
Ile Gly Tyr Thr Cys Leu Leu Ala Ala Ile Cys Phe Phe Phe Ala Phe
785                 790                 795                 800
Lys Ser Arg Lys Leu Pro Glu Asn Phe Asn Glu Ala Lys Phe Ile Thr
            805                 810                 815
Phe Ser Met Leu Ile Phe Phe Ile Val Trp Ile Ser Phe Ile Pro Ala
            820                 825                 830
Tyr Val Ser Thr Tyr Gly Lys Phe Val Ser Ala Val Glu Val Ile Ala
            835                 840                 845
Ile Leu Ala Ser Ser Phe Gly Leu Leu Gly Cys Ile Tyr Phe Asn Lys
            850                 855                 860
Cys Tyr Ile Ile Leu Phe Lys Pro Cys Arg Asn Thr Ile Glu Glu Val
865                 870                 875                 880
Arg Cys Ser Thr Ala Ala His Ala Phe Lys Val Ala Ala Arg Ala Thr
            885                 890                 895
Leu Arg Arg Ser Ala Ala Ser Arg Lys Arg Ser Ser Ser Leu Cys Gly
            900                 905                 910
Ser Thr Ile Ser Ser Pro Ala Ser Ser Thr Cys Gly Pro Gly Leu Thr
            915                 920                 925
Met Glu Met Gln Arg Cys Ser Thr Gln Lys Val Ser Phe Gly Ser Gly
930                 935                 940
Thr Val Thr Leu Ser Leu Ser Phe Glu Glu Thr Gly Arg Tyr Ala Thr
945                 950                 955                 960
Leu Ser Arg Thr Ala Arg Ser Arg Asn Ser Ala Asp Gly Arg Ser Gly
            965                 970                 975
Asp Asp Leu Pro Ser Arg His His Asp Gln Gly Pro Pro Gln Lys Cys
            980                 985                 990
Glu Pro Gln Pro Ala Asn Asp Ala Arg Tyr Lys Ala Ala Pro Thr Lys
            995                 1000                1005
Gly Thr Leu Glu Ser Pro Gly Gly Ser Lys Arg Pro Thr Thr Met
            1010                1015                1020
Glu Glu Thr
```

-continued

```
<210> SEQ ID NO 8
<211> LENGTH: 944
<212> TYPE: PRT
<213> ORGANISM: Homarus americanus

<400> SEQUENCE: 8
```

| | | | | | | | | | | | | | | | |
|---|---|---|---|---|---|---|---|---|---|---|---|---|---|---|---|
| Met | Arg | Phe | Ser | Phe | Glu | Leu | Tyr | Val | His | Tyr | Leu | Val | Leu | Leu | Ala |
| 1 | | | | 5 | | | | | 10 | | | | | 15 | |
| Leu | Asn | Cys | Gly | Val | Leu | Ser | Tyr | Gly | Pro | Arg | Gln | Arg | Ala | Gln | Lys |
| | | | 20 | | | | | 25 | | | | | 30 | | |
| Thr | Gly | Asp | Ile | Leu | Leu | Gly | Gly | Leu | Phe | Pro | Ile | His | Phe | Arg | Val |
| | | 35 | | | | | 40 | | | | | 45 | | | |
| Ala | Ser | Asn | Asp | Gln | Asp | Leu | Ala | Ala | Lys | Pro | Glu | Ser | Thr | Glu | Cys |
| | 50 | | | | | 55 | | | | | 60 | | | | |
| Val | Arg | Tyr | Asn | Phe | Arg | Gly | Phe | Arg | Trp | Leu | Gln | Ala | Met | Ile | Phe |
| 65 | | | | | 70 | | | | | 75 | | | | | 80 |
| Ala | Ile | Glu | Glu | Ile | Asn | Asn | Ser | Ser | Thr | Leu | Leu | Pro | Asn | Ile | Thr |
| | | | | 85 | | | | | 90 | | | | | 95 | |
| Leu | Gly | Tyr | Ser | Ile | Phe | Asp | Thr | Cys | Asn | Thr | Val | Ser | Lys | Ala | Leu |
| | | | 100 | | | | | 105 | | | | | 110 | | |
| Glu | Ala | Ser | Leu | Ser | Phe | Val | Ala | Gln | Asn | Lys | Ile | Asp | Ser | Leu | Asn |
| | | 115 | | | | | 120 | | | | | 125 | | | |
| Leu | Asp | Gly | Phe | Cys | Asn | Cys | Thr | Gly | Asn | Ile | Pro | Ser | Thr | Ile | Ala |
| | 130 | | | | | 135 | | | | | 140 | | | | |
| Val | Val | Gly | Ala | Cys | Gly | Ser | Ala | Val | Ser | Thr | Ala | Val | Ala | Asp | Leu |
| 145 | | | | | 150 | | | | | 155 | | | | | 160 |
| Val | Gly | Leu | Phe | Tyr | Ile | Pro | Gln | Ile | Ser | Tyr | Ala | Ser | Ser | Ser | Arg |
| | | | | 165 | | | | | 170 | | | | | 175 | |
| Leu | Leu | Ser | Asn | Lys | Asn | Gln | Tyr | Lys | Ser | Phe | Met | Arg | Thr | Ile | Pro |
| | | | 180 | | | | | 185 | | | | | 190 | | |
| Thr | Asp | Glu | Tyr | Gln | Ala | Ile | Ala | Met | Ala | Ala | Ile | Ile | Asp | His | Phe |
| | | 195 | | | | | 200 | | | | | 205 | | | |
| Gln | Trp | Asn | Trp | Val | Ile | Ala | Ile | Ala | Ser | Asp | Asp | Glu | Tyr | Gly | Arg |
| | 210 | | | | | 215 | | | | | 220 | | | | |
| Pro | Gly | Ile | Glu | Lys | Phe | Glu | Asn | Glu | Met | Phe | Glu | Arg | Asp | Ile | Cys |
| 225 | | | | | 230 | | | | | 235 | | | | | 240 |
| Ile | Asp | Leu | Asn | Val | Leu | Ile | Ser | Gln | Tyr | Leu | Glu | Glu | Ala | Glu | Ile |
| | | | | 245 | | | | | 250 | | | | | 255 | |
| Ile | Arg | Ile | Ala | Asp | Gln | Ile | Gln | Asn | Ser | Thr | Ala | Lys | Val | Ile | Val |
| | | | 260 | | | | | 265 | | | | | 270 | | |
| Val | Phe | Ala | Ser | Gly | Pro | Asp | Val | Glu | Pro | Leu | Val | Lys | Glu | Met | Val |
| | | 275 | | | | | 280 | | | | | 285 | | | |
| Arg | Arg | Asn | Ile | Thr | Asp | Arg | Val | Trp | Leu | Ala | Ser | Glu | Ala | Trp | Ala |
| | 290 | | | | | 295 | | | | | 300 | | | | |
| Leu | Ser | Ser | Leu | Val | Ala | Lys | Pro | Glu | Tyr | Leu | Asp | Val | Met | Gly | Gly |
| 305 | | | | | 310 | | | | | 315 | | | | | 320 |
| Thr | Ile | Gly | Phe | Ala | Leu | Gln | Ala | Gly | His | Val | Pro | Gly | Phe | Lys | Glu |
| | | | | 325 | | | | | 330 | | | | | 335 | |
| Phe | Leu | Gln | Gln | Val | His | Pro | Lys | Lys | Ser | Leu | His | Asn | Glu | Phe | Val |
| | | | 340 | | | | | 345 | | | | | 350 | | |
| Arg | Glu | Phe | Trp | Glu | Glu | Thr | Phe | Asn | Cys | Tyr | Leu | Ala | Asp | Ser | Val |
| | | 355 | | | | | 360 | | | | | 365 | | | |

-continued

```
Arg Lys Glu Asp Ser Glu Asn Ser Ser Ala Gly Phe Arg Pro Leu Cys
    370                 375                 380

Thr Gly Glu Glu Asp Ile Thr Ser Val Glu Thr Pro Tyr Leu Asp Tyr
385                 390                 395                 400

Thr His Leu Arg Ile Ser Tyr Asn Val Tyr Val Ala Val Tyr Ala Ile
                405                 410                 415

Ala Glu Ala Leu Gln Asp Ile Leu Thr Cys Thr Pro Gly Arg Gly Leu
            420                 425                 430

Phe Ala Asn Gly Ser Cys Ala Asp Ile Arg Lys Val Glu Ala Trp Gln
        435                 440                 445

Val Leu Lys Gln Leu Arg His Leu Lys Phe Gln Asn Ser Met Gly Glu
    450                 455                 460

Arg Val Arg Phe Asp Glu Ser Ser Glu Leu Ser Ala Asn Tyr Thr Ile
465                 470                 475                 480

Met Asn Trp His Arg Ser Pro Ala Asp Gly Ser Val Val Phe Arg Glu
                485                 490                 495

Val Gly Tyr Tyr Ser Val Asn Gly Lys Lys Gly Ala Lys Leu Ser Ile
            500                 505                 510

Asp Lys Thr Lys Ile Leu Trp Asn Gly Tyr Leu Thr Gln Val Pro Phe
        515                 520                 525

Ser Asn Cys Ser Glu Glu Cys Glu Pro Gly Thr Arg Lys Gly Ile Ile
    530                 535                 540

Glu Gly Lys Pro Thr Cys Cys Phe Glu Cys Thr Asp Cys Ser Asp Gly
545                 550                 555                 560

Glu Tyr Ser Glu Tyr Lys Asp Ala Ser Val Cys Thr Lys Cys Pro Asn
                565                 570                 575

Asn Ser Trp Ser Asn Gly Asn His Thr Ser Cys Phe Leu Lys Glu Ile
            580                 585                 590

Glu Phe Leu Ala Trp Ser Glu Pro Phe Gly Ile Thr Leu Ala Leu Leu
        595                 600                 605

Ala Val Leu Gly Val Leu Leu Thr Ser Phe Val Met Gly Val Phe Val
    610                 615                 620

Arg Phe Arg Asn Thr Pro Ile Val Lys Ala Ser Asn Arg Glu Leu Ser
625                 630                 635                 640

Tyr Leu Leu Leu Phe Ser Leu Ile Cys Cys Phe Ser Ser Ser Leu Val
                645                 650                 655

Phe Ile Gly Glu Pro Gln Asp Trp Thr Cys Arg Leu Arg Gln Pro Ala
            660                 665                 670

Phe Gly Ile Ser Phe Val Leu Cys Ile Ser Cys Ile Leu Val Lys Thr
        675                 680                 685

Asn Arg Val Leu Leu Val Phe Glu Ala Lys Ile Pro Thr Ser Leu His
    690                 695                 700

Arg Lys Trp Trp Gly Leu Asn Leu Gln Phe Leu Leu Val Phe Leu Phe
705                 710                 715                 720

Thr Phe Val Gln Val Met Ile Cys Val Val Trp Leu Tyr Asn Ala Pro
                725                 730                 735

Pro Ala Ser Tyr Arg Asn Tyr Asp Ile Asp Glu Ile Ile Phe Ile Thr
            740                 745                 750

Cys Asn Glu Gly Ser Met Met Ala Leu Gly Phe Leu Ile Gly Tyr Thr
        755                 760                 765

Cys Leu Leu Ala Ala Val Cys Phe Phe Ala Phe Lys Ser Arg Lys
    770                 775                 780

Leu Pro Glu Asn Phe Thr Glu Ala Lys Phe Ile Thr Phe Ser Met Leu
```

```
              785                 790                 795                 800
Ile Phe Phe Ile Val Trp Ile Ser Phe Val Pro Ala Tyr Phe Ser Thr
                    805                 810                 815

Tyr Gly Lys Phe Val Ser Ala Val Glu Val Ile Ala Ile Leu Ala Ser
                820                 825                 830

Ser Phe Ser Leu Leu Ala Cys Ile Phe Phe Asn Lys Val Tyr Ile Ile
            835                 840                 845

Leu Phe Lys Pro Ser Arg Asn Thr Ile Glu Glu Val Arg Ser Ser Thr
        850                 855                 860

Ala Ala His Ala Phe Lys Ala Ala Lys Ala Thr Met Arg Arg Ser
865                 870                 875                 880

Ser Ala Phe Arg Lys Arg Ser Ser Ser Ala Gly Gly Ser Thr Ala Ser
                885                 890                 895

Ser Pro Ser Ser Ser Ile Cys Leu Lys Ala Asn Glu Asn Glu Thr Ala
                900                 905                 910

Thr Pro Ser Gly Gln Arg Arg Ser Gln Arg Pro Arg Val Ser Phe Glu
            915                 920                 925

Ser Gly Thr Met Ser Leu Ser Ile Ala Phe Glu Glu Ala Arg Lys Asn
        930                 935                 940

<210> SEQ ID NO 9
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 9
tgtcktggac ggagccctty ggratcgc                                      28

<210> SEQ ID NO 10
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 10
ggckggratg aargakatcc aracratgaa g                                  31
```

METHODS OF NOURISHING ANIMALS

RELATED APPLICATIONS

This application is a continuation of U.S. application Ser. No. 12/993,783, which is the U.S. National Stage Application of International Application No. PCT/US2009/003165 filed on May 22, 2009, published in English, which claims the benefit of U.S. Provisional Application No. 61/128,619, filed on May 22, 2008. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
a) File name: 22132021004SEQLIST.txt; created Mar. 13, 2014, 64 KB in size.

BACKGROUND OF THE INVENTION

Animal husbandry, the agricultural practice of breeding and raising livestock and other domesticated animals, is a major food-producing industry world-wide. Poor development and growth, disease and even morbidity and mortality of these animals are often caused by poor nourishment (e.g., poor nutrition, poor nutrient absorption and/or utilization), particularly when the animals are young. Accordingly, there is a need for better methods of animal husbandry that can be practiced by various sectors of this industry.

SUMMARY OF THE INVENTION

The present invention is based, in part, on the detection of Calcium Sensing Receptor (CaSR) proteins in various tissues of animals, and the finding that different CaSR modulators can alter the expression of CaSR receptors in these tissues, thereby influencing the physiology, growth and development of the animal.

The present invention provides, in one embodiment, a method of maintaining a desired calcium homeostasis in a non-human terrestrial animal that is administered an agent that adversely affects calcium homeostasis in the animal. The method comprises co-administering the agent and one or more CaSR modulator(s) to the animal in an effective amount to maintain calcium homeostasis to a desired level in the animal.

The invention also provides, in another embodiment, a method of restoring a desired calcium homeostasis in a non-human terrestrial animal that has been administered an agent that adversely affects calcium homeostasis in the animal. The method comprises administering one or more CaSR modulator(s) to the animal in an effective amount to restore calcium homeostasis in the animal.

In yet another embodiment, the invention relates to a method of preventing foot (e.g., foot pad) lesions in a terrestrial avian animal. The method comprises administering to an avian animal that has ingested, is ingesting, or will ingest an agent that adversely affects calcium homeostasis resulting in foot pad lesions, one or more CaSR modulator(s) in an effective amount to prevent foot pad lesions in the animal. In a preferred embodiment, the terrestrial avian animal is a chicken.

The invention further relates to a method of weaning a young pig, comprising administering one or more CaSR agonist(s) to the pig in an effective amount to agonize one or more Calcium-Sensing Receptors (CaSRs) in the gastrointestinal tract of the pig.

In addition, the invention provides a method of improving the skin of an avian animal, comprising administering one or more CaSR antagonist(s) and a source of Vitamin D in effective amounts to antagonize one or more Calcium-Sensing Receptors (CaSRs) in the skin of the animal.

The invention also relates to a method of inhibiting an enteric condition in a non-human terrestrial animal, comprising administering fendiline to the animal in an effective amount to modulate one or more Calcium-Sensing Receptors (CaSRs) in the gastrointestinal tract of the animal.

The invention further relates to a food composition for non-human animal consumption, comprising at least one chelated mineral compound in an amount that adversely affects calcium homeostasis in the animal and at least one CaSR modulator in an effective amount to maintain and/or restore a desired calcium homeostasis in the animal.

In addition, the invention relates to a food composition for chicken consumption, comprising at least one agent in an amount that adversely affects calcium homeostasis in the animal, 25-hydroxycholecalciferol at a concentration of about 0.05% by weight and a source of calcium.

The methods and feeds of the present invention can be used to produce animals with improved health and growth, as well as other beneficial traits, relative to many methods and feeds that are currently employed in animal husbandry.

BRIEF DESCRIPTION OF THE DRAWINGS

FIGS. 2A-C show the complete nucleotide sequence (SEQ ID NO:1) of a chick jejunum CaSR cDNA transcript.

FIG. 3 shows the predicted amino acid sequence (SEQ ID NO:2) encoded by the CaSR cDNA nucleotide sequence shown in FIG. 2. All amino acids are denoted by single letter standard code.

FIGS. 5A and B show the aligned amino acid sequences of calcium receptors that have been cloned from human parathyroid (SEQ ID NO:3), chicken jejunum (SEQ ID NO:4), salmon kidney (SEQ ID NO:5), cod kidney (SEQ ID NO:6), shark kidney (SEQ ID NO:7) and lobster genomic DNA (SEQ ID NO:8). Conserved cysteine residues are indicated by vertical boxes. Amino acid residues that are partially conserved (i.e., conserved in some but not in all six of the sequences) are underlined.

FIG. 9A is a Northern blot of mRNA isolated from segments of chick intestine or kidney using a 32P-labeled full-length CaSR cDNA probe from chick jejunum. Lanes: 1) proximal ⅓ of intestine 2) middle ⅓ of intestine; 3) distal ⅓ of intestine and 4) kidney.

FIG. 9B is the same blot shown in FIG. 9A after being stripped and reprobed with a beta-actin probe to assess differences in mRNA lane content.

FIG. 11A is an image depicting immunolocalization of CaSR protein in a section of proximal intestine from a newly hatched chicken. The presence of CaSR protein is indicated by a gray reaction product and arrows.

FIG. 11B is an image depicting immunolocalization of CaSR protein in a section of distal intestine from a newly hatched chicken. The presence of CaSR protein is indicated by a gray reaction product and arrows.

FIG. 11C is an image depicting immunolocalization of CaSR protein in a section of proximal intestine from a 5 day old chicken. The presence of CaSR protein is indicated by a gray reaction product and arrows.

FIG. 11D is an image depicting immunolocalization of CaSR protein in a section of proximal intestine from a 10 week old chicken. The presence of CaSR protein is indicated by a gray reaction product and arrows.

FIG. 20B is a listing of the concentrations of the ionic constituents of sow's milk and colostrum.

FIG. 20C is a graph depicting how recombinant CaSR protein expressed by HEK cells is activated by concentrations of spermine and calcium that are present in sow's milk, as shown in FIG. 20B.

FIG. 26A: After an initial addition of 2.5 mM Ca2+ the mammalian CaSR shows a response to the addition of 0.025% Mintrex Zn. Subsequent addition of Ca2+ to a final concentration of 5 mM produces an additional response.

FIG. 26B: After addition of experimental buffer (EB), no response is observed upon addition of 0.025% Mintrex Zn.

FIG. 26C: After 2 additions of EB, Ca2+ is added to a final concentration of 5 mM.

FIG. 26D: Addition of the CaSR modulator, MC0100 to a final concentration of 1 micromolar does produce a very small CaSR response and subsequent addition of 0.025% Mintrex Zn now elicits a response as does a subsequent addition of Ca2+ to a final concentration of 5 mM.

FIG. 28A: The tracing indicated by the open diamonds shows that after an initial addition of dimethylsulfoxide (DMSO) addition of Ca2+ to a final concentration of 2.5 mM elicits a response by the mammalian CaSR that is also present upon subsequent addition of Ca2+ to a final concentration of 5 mM. By contrast, as shown by the solid squares, addition of 1 micromolar MC 106 suspended in the same concentration of DMSO does not itself produce a CaSR response but eliminates the CaSR response to 2.5 mM Ca2+ and reduces the subsequent response to 5 mM Ca2+.

FIG. 30A: Prior addition of Ca++ to a final concentration of 2.5 mM (solid squares) or 1 micromolar MC0100 (open triangles) produced a similar response of the avian CaSR as did experimental buffer (EB) alone (solid diamonds) when 0.25% Zinc Proteinate was then added to the cells. Subsequent addition of additional Ca++ to a final concentration of 7.5 mM to any of the 3 aliquots (EB alone; MC0100 or 2.5 mM Ca++) produced little or no CaSR response. By contrast, prior addition of 1 micromolar MC106 (open circles) reduced the avian CaSR's response to Zn Proteinate.

FIG. 30B: Similar analyses of the effects of prior addition of Ca++, MC0100 or MC 106 on the response of the mammalian CaSR to Zinc Proteinate. The pattern of inhibition by MC106 on the CaSR response to Zinc Proteinate was similar to the pattern displayed in FIG. 30A.

FIG. 30C: Similar analysis of the effect of pre-addition of MC106 on the avian CaSR on stimulation with zinc organic acid chelate, Mintrex Zn.

FIG. 30D: Similar analysis of the effect of MC106 to suppress the stimulation of the mammalian CaSR by the zinc organic acid chelate, Mintrex Zn.

FIG. 31A: Three individual aliquots from a single pool of HEK cells that stably express the recombinant avian CaSR protein were used for ratio imaging fluorimetry assays of CaSR activation as described previously. After a standard addition of Ca++ to a final concentration of 2.5 mM, either 0.0025% (solid squares) or 0.025% (open diamonds) or 0.25% Zinc Proteinate was added followed by a second addition of Ca++ to a final concentration of 7.5 mM. Lastly, an aliquot of the detergent Triton X-100 was added to lyse the cells. 0.0025% Zinc Proteinate elicits little or no CaSR response while 0.025% and 0.25% Zinc Proteinate produces increasing responses from the avian CaSR. The magnitude of the subsequent CaSR response to Ca++ was reduced by increasing Zn Proteinate stimulation.

FIG. 31B: Identical analyses as performed in FIG. 31A with Zn Proteinate except using HEK cells stably expressing the mammalian CaSR. The mammalian CaSR displays a similar dose response pattern as the avian CaSR.

FIG. 31C: Identical analyses as performed in FIGS. 31A and B except using the zinc organic acid chelate, Mintrex Zn, at concentrations of 0.025% (open squares) and 0.25% (solid diamonds) using HEK cells stably expressing the avian CaSR. A similar dose response relationship as compared to Zn proteinates and the avian and mammalian CaSRs was observed.

FIG. 31D: Identical analyses as performed in FIG. 31C using the zinc organic acid chelate, Mintrex Zn, at concentrations of 0.025% (open squares) and 0.25% (solid diamonds) on HEK cells stably expressing the mammalian CaSR. Mintrex Zn exhibits a dose response relationship with Mintrex Zn similar to that displayed by the avian CaSR in FIG. 31C.

FIG. 40B: No dark areas of staining were observed when using the pre-immune antiserum.

FIG. 45A is a graph showing the ionized calcium of broiler chickens on Day 24/25 of a 42 Day Grow Out study. A total of 1080 Cobb broiler chickens were divided into 5 test groups and reared under conditions described in FIGS. 42A and B. Mean values for ionized calcium concentrations for the 5 test groups are shown. The birds receiving the combination of Mintrex Zn+MC0100 displayed an ionized calcium concentration that was significantly lower than all other test groups.

FIG. 45B is a graph showing the total serum calcium of broiler chickens on Day 24/25 of a 42 Day Grow Out study. A total of 1080 Cobb broiler chickens were divided into 5 test groups and reared under conditions described in FIGS. 42A and B. These values correspond to the same samples used for determination of ionized calcium shown in FIG. 45A. The birds receiving the combination of Mintrex Zn+MC106 displayed the highest total calcium concentrations.

DETAILED DESCRIPTION OF THE INVENTION

Definitions

Figure 1:
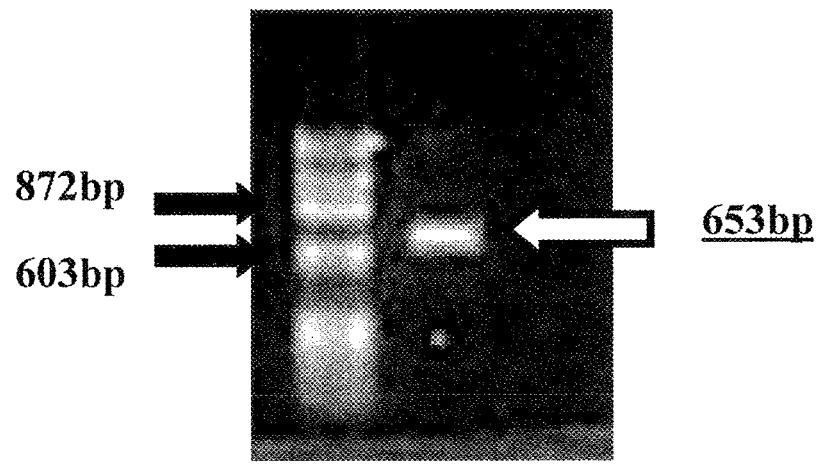
FIG. 1 is an image of an electrophoretic gel showing a 653 bp fragment (open arrow) containing a CaSR sequence that was amplified from chick intestine by reverse-transcriptase polymerase chain reaction (RT-PCR). Molecular weight standards are shown in the left lane, with the positions of the 603 bp and 872 bp standards indicated by black arrows.

The term "non-human terrestrial animal" refers to a non-human animal that lives predominantly or entirely on land. A "non-human terrestrial animal" can be, for example, a mammal (e.g., a bovine species, a porcine species, an equine species) or an avian animal. The animal can be of any age or at any stage of development.

A "young animal" refers to an animal in a stage of development between the time it is separated from its fetal environment and the time when rapid growth ceases. Thus, a "young animal" can be, for example, a neonatal, juvenile or adolescent animal. In the case of mammals, a young animal can be a nursing animal or a weanling. In the case of egg-laying species, the young animal can be an animal developing within an unhatched egg or a hatched animal.

The term "Calcium-Sensing Receptor" or "CaSR" refers to any multimodal G protein coupled receptor (GPCR) that senses extracellular levels of calcium ions and/or other ions (e.g., $Zn^{2+}$, $Mn^{2+}$, $Cu^{2+}$). CaSRs are also known in the art as "polyvalent cation-sensing receptors," "polyvalent cation receptors" and "PVCRs," and these terms are used interchangeably herein. CaSR proteins from different animal species are known in the art. Other CaSR proteins include those identified herein (e.g., SEQ ID NO:3).

"CaSR modulator" refers to any naturally-occurring, recombinant, synthetic or semi-synthetic agent that binds to or otherwise modulates the expression, sensitivity, activity, signalling and/or physiological function of a CaSR protein in one or more tissues of a young animal. A "CaSR modulator" can be, for example, a CaSR agonist, also referred to herein as a calcimimetic, or a CaSR antagonist, also referred to herein as a calcilytic. The term "CaSR modulator" encompasses primary receptor ligands as well as allosteric modulators of a CaSR protein. Preferred CaSR modulators include, for example, polyvalent cations (e.g., divalent cations, trivalent cations, organic polycations), L-amino acids (e.g., L-aromatic amino acids, L-kynurenines), peptides, phenylalkylamines, polyaromatic hydrocarbons, substituted piperidines and substituted pyrrolidines. Particularly preferred CaSR modulators include, for example, peptides (e.g., gly-gly-arg tripeptide, glutathione), divalent cations ($Ca^{2+}$ ions, $Mg^{2+}$ ions), aromatic amino acids (e.g., trytophan), polyamines (e.g., spermine, spermidine, putrescine, diaminopropane), phenylalkylamines (e.g., MC 0100, fendiline, prenylamine), mineral chelates (e.g., Mintrex Zn) and casein.

"CaSR agonists" include Type I agonists/calcimimetics, which do not require Ca2+ to agonize a CaSR, and Type II agonists/calcimimetics, which require Ca2+ to agonize a receptor.

As used herein, the "sensitivity" of the CaSR refers to alteration of CaSR expression in response to a change in the concentration of CaSR modulators or an alteration in the ability of the CaSR to respond to various ligands that stimulate its interaction with other cellular signal transduction pathways. CaSR expression can be assessed by measuring or detecting CaSR polypeptide or nucleic acid molecules in a sample by standard methods.

An "effective amount" as defined herein refers to an amount or concentration of one or more CaSR modulator(s) sufficient to achieve a desired effect on an animal that is administered the one or more CaSR modulator(s) under the conditions of administration. The desired effect can be, for example, maintenance of calcium homeostasis, restoration of calcium homeostasis, enhanced nutrient absorption, and/or utilization, improved growth, inhibition of an enteric condition, reduction in foot lesions, promotion of weaning, and improved skin. Preferably, an "effective amount" of a CaSR modulator does not produce significant detrimental effects associated with excessive CaSR modulation in an animal, including, but not limited to, toxicity, hypercalcemia, hypocalcemia, reduced appetite, disturbances in electrolyte levels, decreased nutrient utilization and/or fluid retention, and tissue dysfunction (e.g., gastrointestinal tissue dysfunction, nervous tissue dysfunction, endocrine tissue dysfunction).

As used herein, the terms "ionic balance homeostasis" and "mineral balance homeostasis" are used interchangeably and refer to the mechanism by which essential ions (e.g., Zn, Ca, Cu, Mn) are maintained at adequate levels in an animal's tissues and fluids.

As used herein, the term "calcium homeostasis" refers to the mechanism by which calcium is maintained at adequate levels in an animal's tissues and fluids. Multiple parameters contribute to calcium homeostasis, including, for example, the concentrations of ions (calcium, magnesium, sodium), amino acids and CaSR modulators in bodily fluids, as well as fluids that bathe various external tissues that express CaSRs, such as the lining of the gastrointestinal tract. In addition, collections of stored calcium present in various tissues, such as bone and skin, also contribute to calcium homeostasis. Absorptive and excretion mechanisms present in specific tissues, including the kidney and gastrointestinal tract, further contribute to calcium homeostasis via regulation of the flux of calcium and other CaSR modulators into and out of the body. Calcium sensing receptors (CaSRs) are the principal calciostat affecting calcium homeostasis in an animal.

As used herein, the expression "maintaining calcium homeostasis" in an animal means preserving a desired calcium homeostasis in an animal.

As used herein, the expression "desired calcium homeostasis" refers to a physiological state in which calcium is present in an animal's tissues and fluids at levels that are sufficient to promote growth, development and/or maintenance of skeletal, muscle and fluid constituents in the animal, or to achieve other desired conditions, characteristics or properties in the animal.

As used herein, the expression "restoring calcium homeostasis" in an animal means returning calcium homeostasis to a desired level in an animal that has been administered one or more CaSR modulators that adversely affect calcium homeostasis in the animal.

A "CaSR modulator that adversely affects calcium homeostasis" refers to an agent that, when administered to an animal, alters calcium homeostasis in the animal in a manner that is not beneficial to the animal's growth, development and/or maintenance of skeletal, muscle or fluid constituents. Such agents can affect a single tissue component (e.g., a CaSR), or several tissue components, that are required to maintain a desired calcium homeostasis in the animal.

As used herein, the phrase "enhancing nutrient utilization" in an animal means increasing the level of nutrients that are absorbed and/or utilized by one or more tissues (e.g., gastrointestinal tissues) of an animal that receives a diet that is supplemented with additional amounts of a CaSR modulator(s) relative to a suitable control level (e.g., the level of nutrients that are absorbed and/or utilized by one or more tissues of an animal that receives a diet that is not supplemented with additional amounts of a CaSR modulator(s)). The level of nutrients that are absorbed and/or utilized by one or more tissues in an animal can be determined, for example, by determining the difference between the level of a nutrient in a food source that is ingested by the animal, and the level of that nutrient that is excreted in the urine and stool of the animal. "Enhancing nutrient utilization" includes inhibiting (e.g., preventing, reducing, treating) one or more enteric conditions that contribute to poor nutrient absorption and/or utilization in an animal (e.g., diarrhea, abnormal gut development, impaired nutrient utilization). Nutrient utilization can be assessed, for example, by determining the Feed Conversion Ratio (FCR) of the animals. The feed conversion ratio or FCR is obtained by dividing the body weight gained by a group of animals into the amount of food fed to these animals. The more efficient the conversion of food into body weight growth by animals, the smaller the FCR (small amount of food/large weight gain of animals). A very small FCR number (less than 1) encompasses a highly efficient conversion of food into body weight growth and is what the industry is striving for. By contrast, a large FCR means an inefficient conversion of food into body weight growth and is generally undesirable. A large or poor FCR is undesirable because feed usually is expensive and more must be used to grow animals to a desired weight.

As used herein, the terms "co-administer," "co-administered," and "co-administering" refer to the act of administering a combination of two or more agents (e.g., two or more CaSR modulators, an agent that adversely affects calcium homeostasis in an animal and one or more CaSR modulators) to an animal either simultaneously or sequentially during a short period of time (e.g., less than an hour). Two or more agents can be co-administered, for example, by including the two or more agents in the same feed that is provided to the animal.

The term "food source" refers to a composition that can be delivered to the gastrointestinal tract of a young animal and includes nutrients utilized by the young animal for nourishment. Thus, a "food source" can be, for example, a feed composition (e.g., a solid feed, a semi-solid feed), a liquid composition (e.g., an aqueous feed, a non-aqueous liquid feed, milk), and a nutritional supplement (e.g., a capsule containing vitamins and/or other nutrients).

The term "peptide" refers to a naturally-occurring, synthetic or semi-synthetic compound that includes from about 2 to about 100 amino acid residues that are joined together by covalent bonds (e.g., peptide bonds, non-peptide bonds). Such peptides are typically less than about 100 amino acid residues in length and are preferably about 2 to about 10 amino acid residues in length. Peptides can be linear or cyclic and can include unmodified and/or modified amino acid residues. In a preferred embodiment, the peptide comprises amino acids that are joined by peptide bonds. The term "peptide" also encompasses peptidomimetics.

As used herein, the term "polypeptide" refers to a polymer of amino acids of any length and encompasses proteins, peptides, and oligopeptides.

"Active polymer" refers to a natural, synthetic or semi-synthetic polymer in a coating that comprises a CaSR modulator as an active agent and releases the active agent under the desired conditions (e.g., the conditions present in a target organ, for example, the stomach or the intestines).

"Weanling" refers to a mammal that is being weaned, or has recently been weaned (e.g., within a few days or weeks), from it's mother's milk to a solid, semi-solid or liquid diet.

Unless otherwise noted, all technical and scientific terms used herein have the same meaning as commonly understood by one of ordinary skill in the art of biology or chemistry (e.g., in cell culture, molecular genetics, nucleic acid chemistry, hybridization techniques and biochemistry). Unless otherwise noted, standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc., the relevant teachings of which are incorporated herein by reference) and chemical methods.

Methods of Nourishing Animals; Methods of Modulating Ionic Balance Homeostasis in Animals The present invention relates to methods of nourishing animals. The methods involve modulating the expression, sensitivity, activity, signalling and/or physiological function of a Calcium-Sensing Receptor (CaSR) (e.g., at least one CaSR) in one or more tissues of the animals. In a particular embodiment, the invention relates to modulating the CaSR(s) in gastrointestinal tissues of animals, which provides increased growth and development of the gastrointestinal tract. In another preferred embodiment, the animal is a young animal.

The invention also provides methods of modulating ionic balance, or mineral balance, homeostasis (e.g., calcium homeostasis) in an animal (e.g., a non-human terrestrial animal). In one embodiment, the invention provides a method of maintaining a desired calcium homeostasis in a non-human terrestrial animal that is administered an agent that adversely affects calcium homeostasis in the animal. The method comprises co-administering the agent and one or more CaSR modulator(s) to the animal in an effective amount to maintain calcium homeostasis in the animal. In another embodiment, the invention relates to a method of restoring a desired calcium homeostasis in a non-human terrestrial animal that has been administered an agent that adversely affects calcium homeostasis in the animal. The method comprises administering one or more CaSR modulator(s) to the animal in an effective amount to restore calcium homeostasis in the animal.

The methods of the present invention include administering one or more CaSR modulator(s) to an animal (e.g., adding one or more CaSR modulator(s) to a food source for an animal (e.g., a young animal), and providing the animal with the food source). The one or more CaSR modulator(s) are administered in an effective amount to modulate at least one CaSR in a tissue of an animal that has ingested the food source.

The methods of the present invention can be practiced on animals of any age, including young, adult and elderly animals. For example, the methods of the invention can be practiced on adult animals, including, but not limited to, adult animals having specialized nutritional needs (e.g., laying hens, lactating cows, pregnant animals). In a preferred embodiment, the animals are young animals.

Particularly suitable animals for the methods of the invention include, but are not limited to, terrestrial animals, including terrestrial mammals and terrestrial avian animals. Preferred terrestrial animals include mammals typically raised as livestock (e.g., cattle, steer, pigs, horses, sheep, deer), as well as companion animals and pets (e.g., dogs, cats, rabbits, ferrets, hamsters, gerbils, guinea pigs, hedgehogs, birds, lizards, snakes, frogs, toads, turtles, spiders, llamas). Particularly preferred terrestrial animals include cattle (e.g., species belonging to the genus *Bos*) and pigs (e.g., *Sus scrofa domesticus*).

Suitable terrestrial avian animals include, for example, chickens, turkeys, ducks, geese, pheasants, grouse, and ostriches. Particularly preferred terrestrial animals include chickens (e.g., *Gallus gallus, G. gallus domesticus*) and turkeys.

The animal can be a monogastric animal (e.g., a chicken, a pig) or a multigastric animal (e.g., a cow). The animals can be raised under standard rearing conditions that are known in the art.

CaSRs, which are located in various tissues (e.g., gastrointestinal tissues, for instance, stomach and intestinal tissue) of the animals, sense alterations in levels of CaSR modulators, including various polyvalent ions (e.g., divalent cations), for example, in the luminal contents of the stomach or intestines. The ability to sense CaSR modulators results in a modulation of the CaSR, thereby allowing the intestines of the animals, and the animals themselves, to grow better, for example by inducing the animals to remodel themselves based on the nutrient and ionic environment that is present in the lumen of the gastrointestinal tract which, in turn, is governed by the type, composition and quality of the food that the young animals consume. The abilities of CaSRs to sense both specific nutrients (e.g., amino acids, polyamines), as well as specific ions (e.g., $Ca^{2+}$, $Mg^{2+}$, $Zn^{2+}$, $Na^+$) permits controlled development of the gastrointestinal tract and allows the animals to grow better. Modulation of the CaSR can occur, for example, in one or more tissues (e.g., gastrointestinal tissues) of an animal.

The modulation of CaSRs by CaSR modulators allows for, or assists in, one or more functions in the animals, including but not limited to, sensing or adapting to at least one CaSR modulator in tissues (e.g., gastrointestinal tissues) or in the surrounding environment; altering the behavioral response to sensory stimuli, especially olfaction and gustation; maintaining or altering (e.g., restoring) osmoregulation or divalent cation (e.g., calcium) homeostasis; altering one or more endocrine pathways; and altering chemosensory signal concentration or composition. CaSR expression can be assessed by measuring or detecting CaSR polypeptide or nucleic acid molecules in a sample by standard methods. Suitable assays and techniques for assessing the expression sensitivity, activity, signaling and/or physiological function of a CaSR are known in the art, and include those described herein.

CaSR modulators include both CaSR agonists (e.g., calcimimetics) that agonize, or increase, the expression, sensitivity, activity, signalling and/or physiological function of at least one CaSR, and CaSR antagonists (e.g., calcilytics) that antagonize, or decrease, the expression, sensitivity, activity, signalling and/or physiological function of at least one CaSR. Calcimimetic CaSR modulators include, for example, Type 1 calcimimetics and Type II calcimimetics (e.g., NPS-R-467 and NPS-R-568 from NPS Pharmaceutical Inc., (Salt Lake, Utah, U.S. Pat. Nos. 5,962,314; 5,763,569; 5,858,684; 5,981,599; 6,001,884). See Nemeth, E. F. et al., *PNAS* 95: 4040-4045 (1998)).

CaSR modulators encompass primary receptor ligands for a CaSR, as well as allosteric modulators of a CaSR (e.g., aromatic amino acids, tryptophan derivatives, peptides). CaSR modulators can be naturally occurring (e.g., isolated from a natural source), synthetic (e.g., produced by standard chemical synthesis techniques), semi-synthetic or recombinant (e.g., produced by biofermentation).

Suitable CaSR modulators for use in the methods of the invention include, but are not limited to, polyvalent cations (e.g., inorganic polycations, organic polycations), amino acids, peptides and small organic molecules. Examples of inorganic polycations are divalent cations including calcium and magnesium; and trivalent cations including, but not limited to, gadolinium (Gd3+). Typically, monovalent and divalent cations, as well as amino acids, are effective CaSR modulators when present in the millimolar concentration range, whereas trivalent cations, peptides and small organic molecules typically are effective CaSR modulators when present in the micromolar concentration range.

Examples of organic polycations include, but are not limited to, aminoglycosides such as neomycin or gentamicin, and polyamines (e.g., polyarginine, polylysine, polyhistidine, polyornithine, spermine, spermidine, cadaverine, putricine, copolymers of poly arginine/histidine, poly lysine/arginine, diaminopropane. See Brown, E. M. et al., *Endocrinology* 128: 3047-3054 (1991); Quinn, S. J. et al., *Am. J. Physiol.* 273: C1315-1323 (1997). In a particular embodiment, the organic polycation is a polyamine.

Additionally, CaSR modulators include amino acids, such as L-amino acids. The L-amino acids can be unmodified or modified (e.g., halogenated). Examples of suitable L-amino acids are L-Tryptophan, L-Tyrosine, L-Phenylalanine, L-Alanine, L-Serine, L-Arginine, L-Histidine, L-Leucine, L-Isoleucine, and L-Cystine. See Conigrave, A. D., et al., *PNAS* 97: 4814-4819 (2000). In a particular embodiment, the L-amino acid is an aromatic amino acid. In a preferred embodiment, the L-amino acid is L-tryptophan. CaSR modulators further include tryptophan-pathway metabolites and tryptophan derivatives, such as, for example, kynurenine, 3-OH kynurenine, xanthurenic acid, quinolic acid and kynurenic acid.

In addition, suitable CaSR modulators for use in the present invention include peptides. Such peptides are typically less than about 100 amino acid residues in length, and are preferably about 2 to about 10 amino acid residues in length (e.g., dipeptides, tirpeptides). The peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine, kynurenine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991. The functional groups of a peptide can also be derivatized (e.g., alkylated) using art-known methods.

The peptide can comprise one or more modifications (e.g., amino acid linkers, acylation, acetylation, amidation, methylation, halogenation, terminal modifiers (e.g., cyclizing modifications)), if desired. The peptide can also contain chemical modifications (e.g., N-methyl-α-amino group substitution). In addition, the peptide can be an analog of a known and/or naturally-occurring peptide, for example, a peptide analog having conservative amino acid residue substitution(s). These modifications can improve various properties of the peptide (e.g., solubility, binding), including its ability to modulate a CaSR in a young animal.

Peptide CaSR modulators can be linear, branched or cyclic, e.g., a peptide having a heteroatom ring structure that includes several amide bonds. In a particular embodiment, the peptide is a cyclic peptide. Such peptides can be produced by one of skill in the art using standard techniques. For example, a peptide can be derived or removed from a native protein by enzymatic or chemical cleavage, or can be synthesized by suitable methods, for example, solid phase peptide synthesis (e.g., Merrifield-type synthesis) (see, e.g., Bodanszky et al. "Peptide Synthesis," John Wiley & Sons, Second Edition, 1976). Peptides can also be produced, for example, using recombinant DNA methodologies or other suitable methods (see, e.g., Sambrook J. and Russell D. W., *Molecular Cloning: A Laboratory Manual*, 3$^{rd}$ Edition, Cold Spring Harbor Laboratory Press, Cold Spring Harbor, N.Y., 2001).

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptides can then be isolated using suitable methods.

Peptide CaSR modulators can also be peptidomimetic compounds. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups that will react or form a complex (e.g., through hydrophobic or ionic interactions) with a target molecule, for example, a young animal CaSR. For example, the binding moieties in a peptidomimetic can be the same as those in a peptide or protein antagonist. The binding moieties can be an atom or chemical group that reacts with the receptor in the same or similar manner as the binding moiety in the peptide antagonist. For example, computational chemistry can be used to design peptide mimetics of CaSR binding site, for instance, a ligand binding site. Examples of binding moieties suitable for use in designing a peptidomimetic for a basic amino acid in a peptide include nitrogen-containing groups, such as amines, quarternary ammonia moieties, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possesses substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more -CONH- groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

Figure 25A:
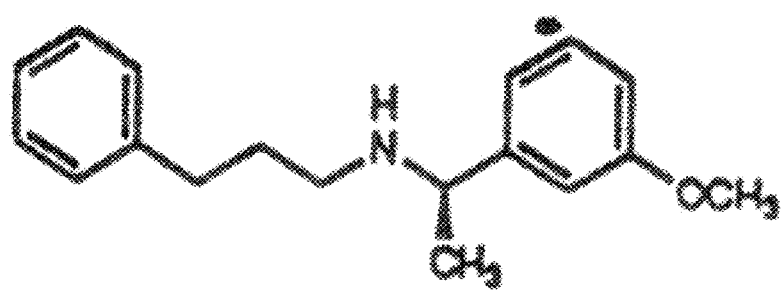
FIG. 25A depicts the chemical structure of the phenylalkylamine calcimimetic compound MC 0100, also known as NPS-R-467.
Figure 25B:
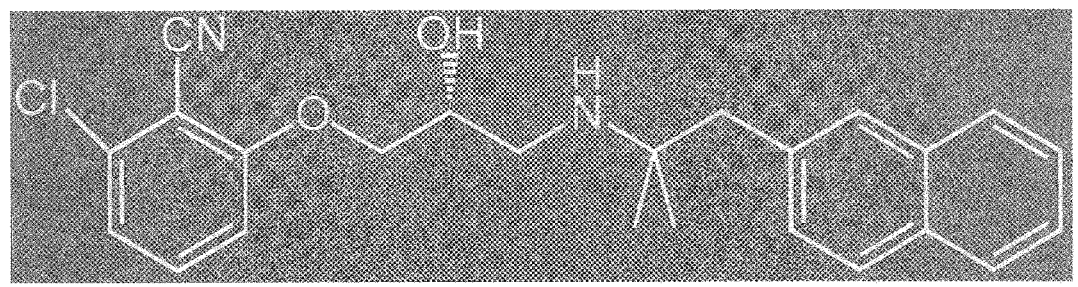
FIG. 25B depicts the chemical structure of the phenylalkylamine calcimimetic compound MC 106, also known as NPS-2143.

In addition, CaSR modulators include phenylalkylamines. Methods of synthesizing, isolating and/or preparing phenylalkylamines are known in the art. Suitable phenylalkylamines for use in the methods of the invention include, but are not limited to, the CaSR agonists, MC 0100 (See FIG. 25), fendiline, prenylamine and cinacalcet, and the CaSR antagonist MC106. Typically, phenylalkylamine modulators of CaSR activities are potent when present in the high nanomolar to low micomolar range.

CaSR modulators can also be substituted piperidines and substituted pyrrolidines. Methods of synthesizing, isolating and/or preparing substituted piperidines and substituted pyrrolidines are known in the art. Suitable substituted piperidines and substituted pyrrolidines for use in the methods of the invention include, but are not limited to, substituted piperidines and substituted pyrrolidines described in U.S. Pat. Nos. 7,265,145 and 7,307,171.

CaSR modulators also include compounds that indirectly alter CaSR expression (e.g., 1,25 dihydroxyvitamin D (e.g., in concentrations of about 3,000-10,000 International Units/kg feed), cytokines such as Interleukin Beta, and Macrophage Chemotactic Peptide-1 (MCP-1)).

In addition, CaSR modulators can be chelated mineral compounds. Typically, chelated mineral compounds include a metal cation component and an organic anion component that serves as a chelator for the metal cation. Preferably, the metal cation component is a divalent metal cation (e.g., Zn2+, Ca2+, Mg2+, Cu2+, Mn2+) or a trivalent metal cation (e.g., Al3+, Gd3+). The organic anion component can be, for example, an organic acid (e.g., (2-hydroxy-4-methylthio)butanoic acid, or HMTBa), an amino acid (e.g., methionine, glycine, cysteine, phenylalanine), a partially hydrolyzed protein or peptide (e.g., a metal proteinate), a polysaccharide (e.g., a gluconate) or an antibiotic that carries a negative charge (e.g., bacitracin, ciprofloxacin and other quinolones, tetracycline).

Examples of chelated mineral compounds that comprise an organic acid component include, but are not limited to, various MINTREX® organic trace mineral compounds (e.g., MINTREX Zn: Novus International, St. Charles, Mo.). Examples of chelated mineral compounds that comprise an amino acid component include, but are not limited to, various metal methionine compounds (e.g., ZINPRO compounds, MANPRO compounds: Zinpro Corporation, Eden Prairie, Minn.; see also U.S. Pat. No. 4,021,569), zinc-cysteine complexes, zinc-phenylalanine complexes and glycinates. Examples of chelated mineral compounds that comprise a partially hydrolyzed protein or peptide component include, but are not limited to, various metal proteinates (e.g., Zinc bacitracin (a cyclic polypeptide metal ion complex) as well as Zinc Proteinates, Manganese Proteinates, Copper Proteinates: Balchem Corporation, New Hampton, N.Y.). Examples of chelated mineral compounds that comprise antibiotics include, but are not limited to, zinc bacitracin, zinc tetracycline and zinc ciprofloxacin.

In the methods of the invention relating to maintaining calcium homeostasis, or restoring calcium homeostasis, in an animal, the agent that adversely affects calcium homeostasis in the animal can be a CaSR modulator itself, such as, for example, a CaSR agonist (e.g., a chelated mineral compound). As described herein, certain chelated mineral compounds can adversely affect calcium homeostasis in an animal (e.g., by decreasing serum calcium levels when administered to the animal at particular concentrations). Examples of chelated mineral compounds that can adversely effect calcium homeostasis in an animal include, for example, MINTREX® organic trace mineral compounds, metal methionine complexes, metal proteinates, and Zinc bacitracin. Other agents that can adversely effect calcium homeostasis in an animal (e.g., at particular concentrations) include, for example, inorganic minerals and inorganic mineral sources (e.g., zinc sulfate). Calcium homeostasis and, indirectly protein metabolism and utilization can be adversely affected by, for example, decreased serum calcium levels, providing for altered levels of counter-regulatory hormones (e.g., parathyroid hormone, calcitonin, gastrin and cholecystokinin), changes in the steady state or fluxes in calcium reabsorption from body stores such as bone or avian skin and the excretion of calcium from the body in the case of milk production in mammals and egg shell production in avian species. Moreover, there can also be adverse effects on nutrient uptake and utilization that would include calcium uptake from dietary sources as well as it reabsorption from various tissues including the kidney.

As described herein, for methods of the invention relating to maintaining and/or restoring calcium homeostasis in an animal, the co-administration and/or prior or subsequent administration of an effective amount of one or more CaSR modulators can maintain or restore calcium homeostasis, respectively, in animals whose calcium homeostasis has been adversely effected by prior or co-administration of an agent that adversely affects calcium homeostasis, such as a chelated mineral compound. Thus, an effective amount of one or more CaSR modulators is able to counteract (e.g., off-set) the negative effects of the agent that adversely affects calcium homeostasis when administered to the animal.

The invention further relates to a method of weaning a young animal, comprising administering one or more CaSR modulator(s) (e.g., CaSR agonist(s)) to the animal in an effective amount to modulate (e.g., agonize) one or more Calcium-Sensing Receptors (CaSRs) in one or more tissues in the animal (e.g., in the gastrointestinal tract). In an embodiment, the young animal is a young porcine animal. Other suitable animals include, for example, bovine animals. Preferably the one or more CaSR agonists employed in the method include a phenylalkylamine (e.g., fendiline, prenylamine, cinacalcet). In a preferred embodiment, the phenylalkylamine is fendiline.

In addition, the invention provides a method of improving the skin of an avian animal (e.g., a broiler chicken, a turkey), comprising administering one or more CaSR modulator(s) (e.g., CaSR antagonist(s)) and a source of Vitamin D (e.g., 25-hydroxycholecalciferol) in effective amounts to modulate (e.g., antagonize) one or more Calcium-Sensing Receptors (CaSRs) in the skin of the animal.

The invention also relates to a method of inhibiting an enteric condition in a non-human animal, comprising administering a one or more CaSR modulators (e.g., CaSR agonists) to the animal in an effective amount to modulate one or more Calcium-Sensing Receptors (CaSRs) in the animal (e.g., in the gastrointestinal tract). Examples of enteric conditions include, but are not limited to, diarrhea, abnormal gut development and impaired nutrient utilization. In an embodiment, the animal is a porcine animal or a bovine animal. Other suitable animals include, for example, companion animals, such as dogs, cats, etc. Preferably the one or more CaSR modulators employed in the method include a phenylalkylamine (e.g., fendiline, prenylamine, cinacalcet). In a preferred embodiment, the phenylalkylamine is fendiline. In some embodiments, the one or more CaSR modulators does not include prenylamine.

Methods of Reducing Foot Lesions in Terrestrial Avian Animals

In another embodiment, the invention relates to a method of preventing foot (e.g., foot pad) lesions in a terrestrial avian animal. The method comprises administering to an avian animal that has ingested, is ingesting, or will ingest an agent that adversely affects calcium homeostasis resulting in foot pad lesions, one or more CaSR modulator(s) in an effective amount to prevent foot pad lesions in the animal. In a preferred embodiment, the terrestrial avian animal is a chicken.

Preferably, the one or more CaSR modulator(s) include at least one CaSR antagonist (e.g., a naturally occurring CaSR antagonist). In one embodiment, the agent that adversely affects calcium homeostasis is a chelated mineral compound. Examples of chelated mineral compounds suitable for use in the methods include organic acid-metal chelates (e.g., HMTBa compounds with divalent cations), amino acid-metal chelates (e.g., zinc methionine compounds) and metal proteinates (e.g., zinc proteinates, copper proteinates, manganese proteinates, zinc bacitracin).

In another embodiment, the invention relates to a method of reducing foot lesions in a chicken by feeding the chicken a food composition comprising at least one chelated mineral compound; 25-hydroxycholecalciferol (e.g., at a concentration of about 0.05% by weight); and a source of calcium.

Administration of CaSR Modulators

A CaSR modulator can be administered to an animal in a number of ways. Preferably, the CaSR modulator is delivered to the gastrointestinal tract of the animal. For example, a CaSR modulator can be added to any one of the food sources described herein (e.g., a feed, a liquid, a nutritional supplement), or any combination thereof (e.g., in both the feed and the water that is provided to the animal), such that the CaSR modulator is delivered to the gastrointestinal tract upon ingestion of the food source by the animal, and the CaSR modulators are released upon digestion.

The CaSR modulators can also be administered in suitable oral dosage forms, such as, for example, tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts.

For instance, for oral administration of CaSR modulators in the form of a tablet or capsule, the CaSR modulator(s) can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the CaSR modulator(s) can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The CaSR modulator(s) can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For egg-laying animals (e.g., chickens), CaSR modulators can also be administered in a composition that is injected directly into the egg before the animal has hatched. Suitable methods for injecting eggs are well known in the art. In the case of feathered animals (e.g., chickens), CaSR modulators can be applied in a composition that is sprayed onto the feathers of the animals, such that the CaSR modulators are ingested by the animals during preening. Suitable methods for spraying feathers are well known in the art.

Certain types of CaSR modulators (e.g., peptides, small organic molecules, such as polyamines and phenylalkylamines) can also be incorporated into polymers that are ingested by the animals, such that individual CaSR modulators are released from the polymers in the gastrointestinal tract of the animals. For example, a peptide or small organic molecule CaSR modulator can serve as the repeating unit of a polymer, wherein the individual CaSR modulators in the polymer are joined by linkages (e.g., peptide bonds, non-peptide covalent bonds) that occur at regular intervals and are selectively cleaved (e.g., chemically, enzymatically, hydrolytically), for example, in the stomach and/or intestine of an animal that has ingested the polymer. The linkages in the polymers can be susceptible to cleavage under conditions present in the target organ (e.g., stomach, intestine), such as acidic (stomach) or alkaline (intestines) pH, or by specific enzymes that are present in the target organ (e.g., trypsin). Suitable cleavable linkages for use in polymers are known to those of skill in the art.

Figures 23A, 23B:
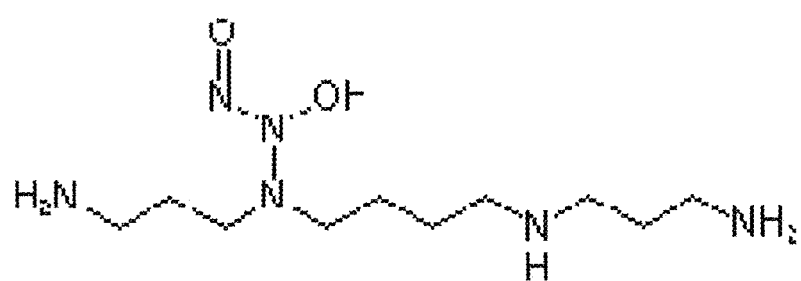
FIG. 23A shows the chemical structure of spermine (N-[4-[1-(3-Aminopropyl)-2-hydrox-2-nitrosohydrazino]butyl-1,3-propanediamine).
FIG. 23B shows the design of a polyamine (spermine) polymer and products generated by hydrolysis of the polymer.
Figure 24:
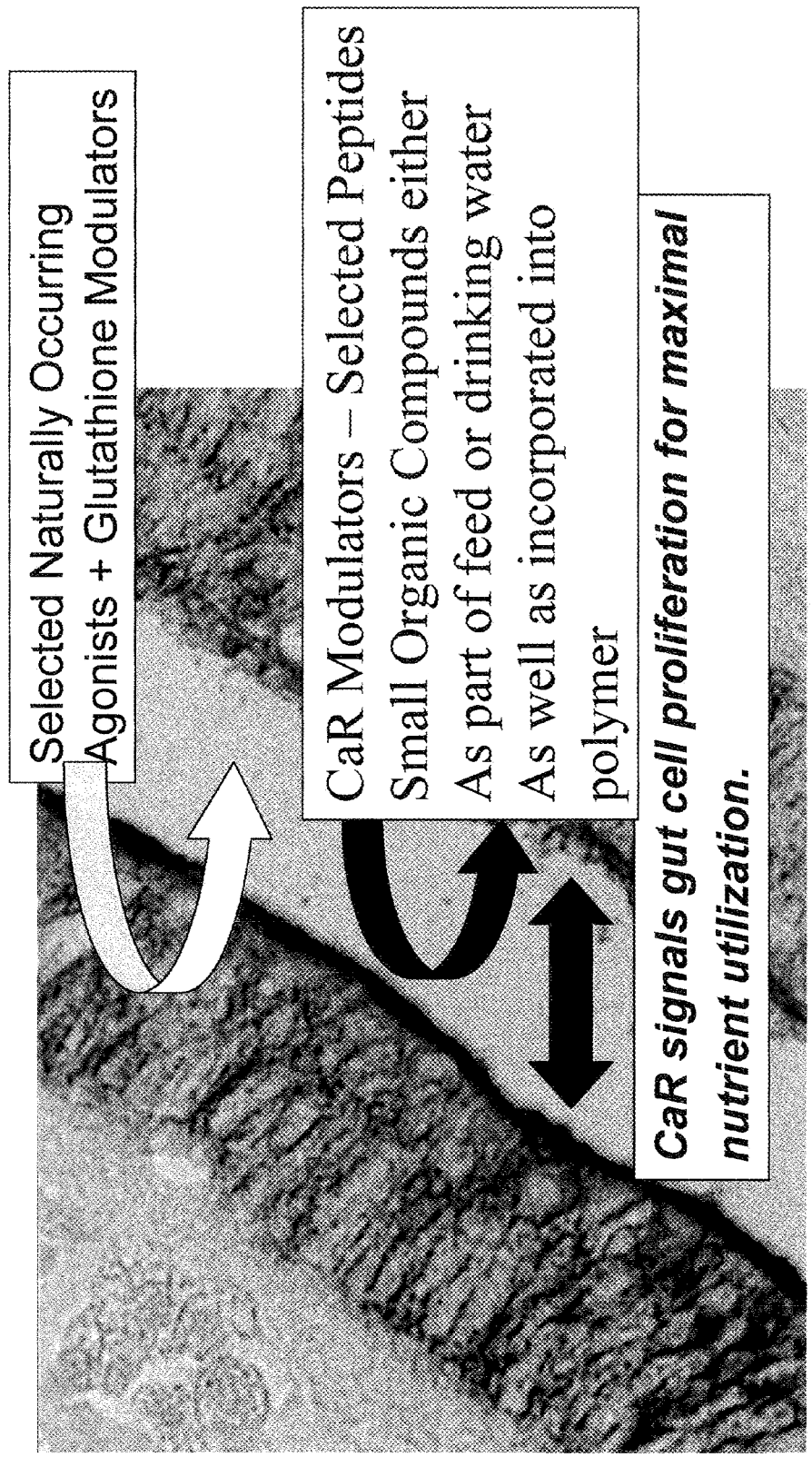
FIG. 24 is a schematic diagram illustrating how CaSRs that are present on the mucosal surfaces of the intestine and stomach of young animals can be modulated by CaSR modulators provided in the diet of a young animal. The gray-colored reaction product shows the localization of CaSRs in a section of animal intestine that has been stained with anti-CaSR antiserum. The lumen of the intestine is in the center of the diagram. The mucosal surface of the intestine is intensely labeled by anti-CaSR staining, and the epithelial cells containing the CaSR protein are constantly exposed to the luminal contents of the intestine. The CaSRs present in the intestine are modulated by ingested CaSR modulators present in the luminal contents of the gastrointestinal tract. A second group of CaSR modulators modulate CaSRs present in the mucosal epithelial cells.

Polymers of CaSR modulators can be prepared using standard chemical synthesis techniques that are well known in the art. For example, standard chemical synthesis techniques could be utilized to create polymers of repeating units that each possess an appropriate number of amino groups positioned at appropriate distances such that, after the ingested polymer had been acted upon by hydrolytic enzymes that are present in the gastrointestinal tract of the animal, the hydrolyzed products can stimulate CaSRs in the mucosa of the gastrointestinal tract. An exemplary polymer containing the CaSR modulator, spermine, is illustrated in FIG. 23B and described herein. For example, examination of the molecular charge distribution of positively charged amino groups on the potent CaSR agonist, spermine, reveals that its 4 amino groups are positioned at similar intramolecular distances from each other (FIG. 23A). Thus, standard chemical synthesis techniques can be utilized to create polymers of repeating units that each possess an appropriate number of amino groups positioned at appropriate distances such that, after the ingested polymer had been acted upon by hydrolytic enzymes that are present in the gastrointestinal tract of the animal, the hydrolyzed products (FIG. 23B) can stimulate CaSRs in the mucosa of the gastrointestinal tract.

Polymers of CaSR modulators can be incorporated into coating materials for capsules or other enclosures that are ingested by the animals, or can themselves be encapsulated in a delivery vehicle (e.g., a capsule, a tablet, a microparticle, a nanoparticle) and ingested by the animals. Such delivery vehicles preferably release the polymer in the target organ (e.g., stomach, intestine) and include both immediate and controlled (e.g., sustained, targeted) release formulations. Thus, the location of release of the polymer, and therefore the CaSR modulator(s), can be carefully controlled.

For example, the CaSR modulator(s) can be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. The CaSR modulator(s) can also be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Micro and nanoparticles that can encapsulate agents in order to provide protection and regulate their rate of release are described in U.S. Pat. No. 5,352,461, which relates to the self-assembling particle drug delivery systems formed from 2,5-diketo-3,6-di(4-succinylaminobutyl) piperazine that disassemble and release the entrapped agent at high pH. Other particles that share the properties of stability at low pH and instability as pH increases are described in International Patent Publication No. WO 88/01213. Self-assembling pH titratable particulate systems, based upon the self-assembling properties of bis-amide dicarboxylic acids are described in the work of Bergeron et al., J. Amer. Chem. Soc. 1995, 117, 6658-6665.

International Patent Publication No. WO 96/29991 describes the formation of self-assembling particles that are based upon polyaminoacids, more particularly polyleucineglutamate. These particles which are prepared from natural amino acids have the property of controlled particle size and are stable over a wide pH range.

Particles for entrapment of agents, and particularly peptides or proteins, can also be formed by polyelectrolyte complexation of various anionic polymers with cationic polymers. Anionic polymers may include natural substances such as sodium alginate, carboxymethyl cellulose, guaran, polyglutamic acid and their derivatives, amongst others. Examples of cationic polymers include polylysine and gelatin. Other polycations and polyanions are described in detail within European Patent No. 671169, U.S. Pat. Nos. 4,835,248 and 5,041,291.

The particles containing CaSR modulators described herein (e.g., microparticles) can, for instance, be absorbed by Peyer's patches in the gut of an animal that has ingested the particles.

In a particular embodiment, the polymer is protected from breakdown in the stomach of the animal by an enteric coating, which is degraded in the intestine of the animal, thereby releasing the polymer into the intestines, where the polymer can be cleaved into its CaSR modulator constituents. Enteric coatings are those coatings that remain substantially intact in the stomach, but dissolve and release the contents of the dosage form once it reaches the small intestine. Enteric coatings have been used for many years to arrest the release of the drug from orally ingestible dosage forms. Depending upon the composition and/or thickness, the enteric coatings are resistant to stomach acid for required periods of time before they begin to disintegrate and permit slow release of the drug in the lower stomach or upper part of the small intestines. Most enteric coating polymers begin to become soluble at pH 5.5 and above, with maximum solubility rates at pHs greater than 6.5.

A large number of enteric coatings have been described and are typically prepared with ingredients that have acidic groups such that, at the very low pH present in the stomach, i.e., pH 1.5 to 2.5, the acidic groups are not ionized and the coating remains in an undissociated, insoluble form. At higher pH levels, such as in the environment of the intestine, the enteric coating is converted to an ionized form, which can be dissolved to release the proanthocyanidin polymer composition. Other enteric coatings remain intact until they are degraded by enzymes in the small intestine, and others break apart after a defined exposure to moisture, such that the coatings remain intact until after passage into the small intestines.

Suitable enteric coatings are described, for example, in U.S. Pat. No. 4,311,833 to Namikoshi, et al.; U.S. Pat. No. 4,377,568 to Chopra; U.S. Pat. No. 4,385,078 to Onda, et al.; U.S. Pat. No. 4,457,907 to Porter; U.S. Pat. No. 4,462,839 to McGinley, et al.; U.S. Pat. No. 4,518,433 to McGinley, et al.; U.S. Pat. No. 4,556,552 to Porter, et al.; U.S. Pat. No. 4,606,909 to Bechgaard, et al.; U.S. Pat. No. 4,615,885 to Nakagame, et al.; and U.S. Pat. No. 4,670,287 to Tsuji.

Preferred enteric coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethylcellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; polycarboxymethylene and its salts and derivatives; polyvinylalcohol and its esters, polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethyleneglycol and its esters, e.g., and natural products such as shellac.

Other preferred enteric coatings include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethyl ether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine. Mixtures of two or more of the above compounds may be used as desired.

The enteric coating material may be mixed with various excipients including plasticizers such as triethyl citrate, acetyl triethyl citrate, diethyl phthalate, dibutyl phthalate, dibutyl sebacate, dibutyl tartrate, dibutyl maleate, dibutyl succinate and diethyl succinate and inert fillers such as chalk or pigments.

The composition and thickness of the enteric coating may be selected to dissolve immediately upon contact with the digestive juice of the intestine. Alternatively, the composition and thickness of the enteric coating may be selected to be a time-release coating which dissolves over a selected period of time, as is well known in the art.

Food Compositions

Any of the CaSR modulators described herein, and combinations thereof, can be added to a food source (e.g., a feed) for an animal. The CaSR modulator(s) are typically added to the food source in an amount (e.g., an effective amount) sufficient to produce a significant positive effect on nutrient absorption and/or utilization in an animal that has ingested the food source to which the CaSR modulator(s) has been added, provided that the CaSR modulator(s) are not present in an amount that produces significant detrimental effects associated with excess CaSR modulation in an animal, including, but not limited to, toxicity, hypercalcemia, hypocalcemia, reduced appetite, disturbances in electrolyte levels, decreased nutrient utilization and/or fluid retention, and tissue dysfunction (e.g., gastrointestinal tissue dysfunction, nervous tissue dysfunction, endocrine tissue dysfunction).

The animals are provided with a food source that contains one or more CaSR modulator(s) in sufficient amounts to modulate the expression, sensitivity, activity, signalling and/or physiological function of at least one CaSR in one or more tissues of the animals. The food source includes nutrients utilized by the animal for nourishment and, preferably, is suitable for ingestion by the animal. The food source can be, for instance, a feed (e.g., a solid feed, a semi-solid feed) for animal consumption. Standard feeds for various species of animal are known in the art. The food source can also be a liquid component of an animals diet (e.g., an aqueous composition, milk, colostrum). Food sources can also include nutritional supplements, such as, for example, vitamins, cofactors, enzymes, oils, herbs, and medicaments. Such supplements can be provided to young animals in, e.g., microparticles, nanopatricles, polymers, coatings, tablets, capsules, pills, cachets, powders, granules, elixirs, tinctures, suspensions, syrups, emulsions, and/or other suitable enclosures for nutrients that are known in the art.

The frequency and amount of feed that an animal is fed can be determined by those of skill in the art and will vary depending on a number of factors, including the species of the animal, as well as its size, age, weight, health and gender, among other factors.

In one embodiment, the invention relates to a food composition for non-human terrestrial animal consumption, comprising:

a.) at least one chelated mineral compound in an amount that adversely affects calcium homeostasis in the animal; and b.) at least one CaSR modulator in an effective amount to maintain and/or restore calcium homeostasis (e.g., a desired calcium homeostasis) in the animal.

Suitable chelated mineral compounds for the food composition include, but are not limited to, compounds comprising HMTBa and a divalent metal cation (e.g., $Zn^{2+}$, $Cu^{2+}$, $Mn^{2+}$), compounds comprising methionine and a divalent metal cation (e.g., $Zn^{2+}$, $Cu^{2+}$, $Mn^{2+}$), a zinc proteinate, a copper proteinate, a manganese proteinate and zinc bacitracin. The at least one chelated mineral compound can be present in the composition, for example, at a concentration in the range of about 10 parts per million to about 200 parts per million by weight, preferably, at a concentration of about 20 parts per million to about 80 parts per million by weight.

Suitable CaSR modulators for the food composition include, for example, CaSR antagonists (e.g., MC106). The at least one CaSR modulator can be present in the composition at a concentration, for example, in the range of about 50 parts per million to about 150 parts per million by weight, preferably, at a concentration of about 50 parts per million to about 90 parts per million by weight.

In another embodiment, the invention relates to a food composition for chicken consumption, wherein the food composition is useful for preventing (e.g., inhibiting) lesions on chicken feet, comprising:
 a.) at least one agent that adversely affects calcium homeostasis in the animal;
 b.) 25-hydroxycholecalciferol; and
 c.) a source of calcium.

In one embodiment, the agent is a chelated mineral compound. Examples of chelated mineral compounds suitable for the chicken food compositions of the invention include, but are not limited to, compounds comprising (2-hydroxy-4-methylthio)butanoic acid (HMTBa) and a divalent cation (e.g., Zn2+, Cu2+, Mn2+). The at least one chelated mineral compound can be present in the composition in an amount that adversely affects calcium homeostasis in the chicken (e.g., an amount sufficient to decrease serum calcium levels). In some embodiments, at least one chelated mineral compound is present in the composition at a concentration of about 0.05% to about 0.50% (5 ppm to 50 ppm) by weight. Preferably, the at least one chelated mineral compound is present in the composition at a concentration of about 0.10% (10 ppm) by weight.

The 25-hydroxycholecalciferol is present in the composition at a amount that is effective to reduce foot lesions in the chicken (e.g., an amount that is effective to maintain or restore a desired calcium homeostasis in the chicken), for example, at a concentration of about 0.02% to about 0.10% by weight, preferably, at about 0.05% by weight.

The source of calcium can be an inorganic calcium source or an organic calcium source. The calcium is present in the composition at a amount that is effective to reduce foot lesions in the chicken (e.g., an amount that is effective to maintain or restore a desired calcium homeostasis in the chicken), for example, preferably in a range of about 1.00% to about 2.00% by weight, more preferably in the range of about 1.40% to about 1.45% by weight.

For ruminant animals like steers, cows or lambs, chelated mineral compounds such as zinc, manganese or copper proteinates can be provided as a % of the total trace mineral requirement. In some embodiments, metal proteinates would be added such that their portion would be 15-30% of the total trace mineral requirement that itself would be provided at various concentrations depending on the portion that is provided as inorganic mineral constituents.

For monogastric animals such as weaning pigs, chelated mineral compounds such as copper, zinc and manganese can be also provided a % of the total trace mineral requirement. In some embodiments, metal proteinates would be added at levels of approximately 50-100 parts per million as an appropriate % of the total trace mineral requirement for this species. For other monogastric animals such as dogs and cats similar quantities of chelated trace minerals would be provided at various concentrations depending on the portion that is provided as inorganic mineral constituents and the specific life stage of the particular animal.

The invention is further specifically described in the following examples.

EXEMPLIFICATION

Example 1

Identification, Isolation and Characterization of a CaSR Protein in the Jejunum of Chickens Materials and Methods
 Tissue Preparation
 Gastrointestinal (i.e., duodenum, jejunum and ileum), kidney and brain tissues were harvested from 22 day old chickens (n=3), frozen on dry ice and stored at −80° C.
 RNA Extraction
 Total RNA was purified from the jejunum using STAT-60 (Teltest B, Friendswood, Tex.), and poly A+ mRNA was isolated using the Micro-FastTrack 2.0 Kit (Invitrogen, Carlsbad, Calif.).
 Chick Jejunum cDNA Library Construction
 cDNA was synthesized by reverse transcribing chick jejunum mRNA, prepared as described above. Selected cDNA fractions were ligated and packaged as ZAP libraries (ZAP-cDNA synthesis Kit and ZAP-cDNA Gigapack III Gold Cloning Kit, Stratagene, La Jolla, Calif.). Degenerate CaSR-specific DNA primers (dSK-F3: 5'-TGT CKT GGA CGG AGC CCT TYG GRA TCG C-3' (SEQ ID NO:9); dSK-R4: 5'-GGC KGG RAT GAA RGA KAT CCA RAC RAT GAA G-3' (SEQ ID NO:10) were used to selectively amplify a ~653 bp fragment of a chick CaSR transcript (FIG. 1), which was used as a probe for the isolation of a full length CaSR cDNA from chick jejunum. A total of 40,000 phage plaques were screened using duplicate filter lifts (Magna Nylon membranes, GE Osmonics) using the ~653 bp chicken CaSR probe created using degenerate CaSR primers that was $^{32}$P-labeled with the RadPrime DNA Labeling System (Invitrogen) to greater than 50% incorporation. Hybridization of the plate-lifts was carried out overnight at 68° C. in 6×SSC, 0.5% SDS, 5×Denhardt's solution, and membranes were washed under relatively stringent conditions (30 minutes in 2×SSC, 0.1% SDS, 30 minutes in 0.1×SSC, 0.1% SDS, all at 55° C.). A single positive plaque was picked, eluted, and plated. These plates were lifted onto nylon membranes and subjected to secondary and tertiary hybridization screening.
 DNA Sequencing
 Tertiary picks were excised from their Lambda-Zap phagemids and transformed into chemically competent DH5a cells. From this point on, the excised clone was in pBluescript SK−. Upon standard miniprep and confirmation of insert, the clone was midiprepped using the Wizard Plus Midiprep DNA Purification System (Promega) and sequenced using commercially available DNA sequencing facilities at the University of Maine DNA Sequencing Facility.
 Genomic Southern Analysis
 Genomic DNA from chicken heart tissue was prepared using the Wizard Genomic DNA Purification Kit (Promega), and a 10 μg of the DNA was digested overnight with EcoRI. The resulting genomic DNA digest was fractionated using a 0.7% agarose gel which was then stained and then transferred to a charged nylon membrane (Ambion BrightStar Plus). The resulting membrane was then hybridized overnight at 68° C. in 6×SSC, 0.5% SDS, 5×Denhardt's solution, using a $^{32}$P-labeled probe made from our full-length chicken clone (prepared with Invitrogen's RadPrime DNA Labeling System to greater than 50% incorporation). The blot was washed as follows: 30 minutes in 2×SSC, 0.1% SDS, 30 minutes in 0.2×SSC, 0.1% SDS, all at 53° C. (relatively stringent for Genomic Southern Blotting).

Results

A full-length cDNA encoding a CaSR from chick jejunum (FIGS. 2A-C) was isolated from a chick jejunum cDNA library using a 653 bp fragment of chick CaSR transcript that was selectively amplified using degenerate CaSR specific DNA primers as described above. Analysis of the full-length cDNA sequence revealed that the CaSR coding region of the clone is 5336 bp in length and contains a full length open reading frame of 5252 bp that is nearly identical to that of the known chicken calcium-sensing receptor (GenBank accession number XM 416491). The DNA sequence shown in FIGS. 2A-C differs from the GenBank sequence by 11 bases (nucleotides 329, 1397, 2087, 3818, 4145, 4637, 4740, 5036, 5078, 5139, and 5319), and encodes a predicted 1,059 amino acid polypeptide (FIG. 3).

Figure 4:
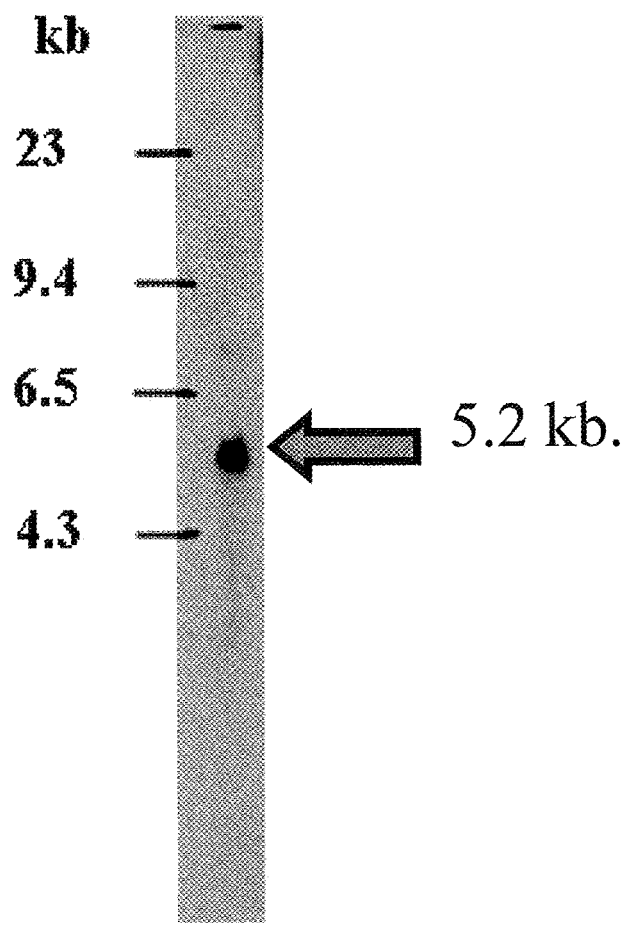
FIG. 4 is a Southern blot of chicken genomic DNA that was digested with EcoRI and probed with $^{32}$P-labeled cDNA containing chick intestinal CaSR cDNA sequence prepared from the sequence shown in FIG. 2. A 5.2 kb EcoRI fragment hybridizes to the CaSR cDNA sequence.

To verify that the CaSR cDNA sequence was contained in the genomic DNA of chickens, Southern blotting analysis was performed as described above after EcoRI digestion of isolated chicken genomic DNA, revealing a single 5.2 kb EcoRI genomic fragment that hybridized to the CaSR cDNA sequence (FIG. 4).

Figure 5A:
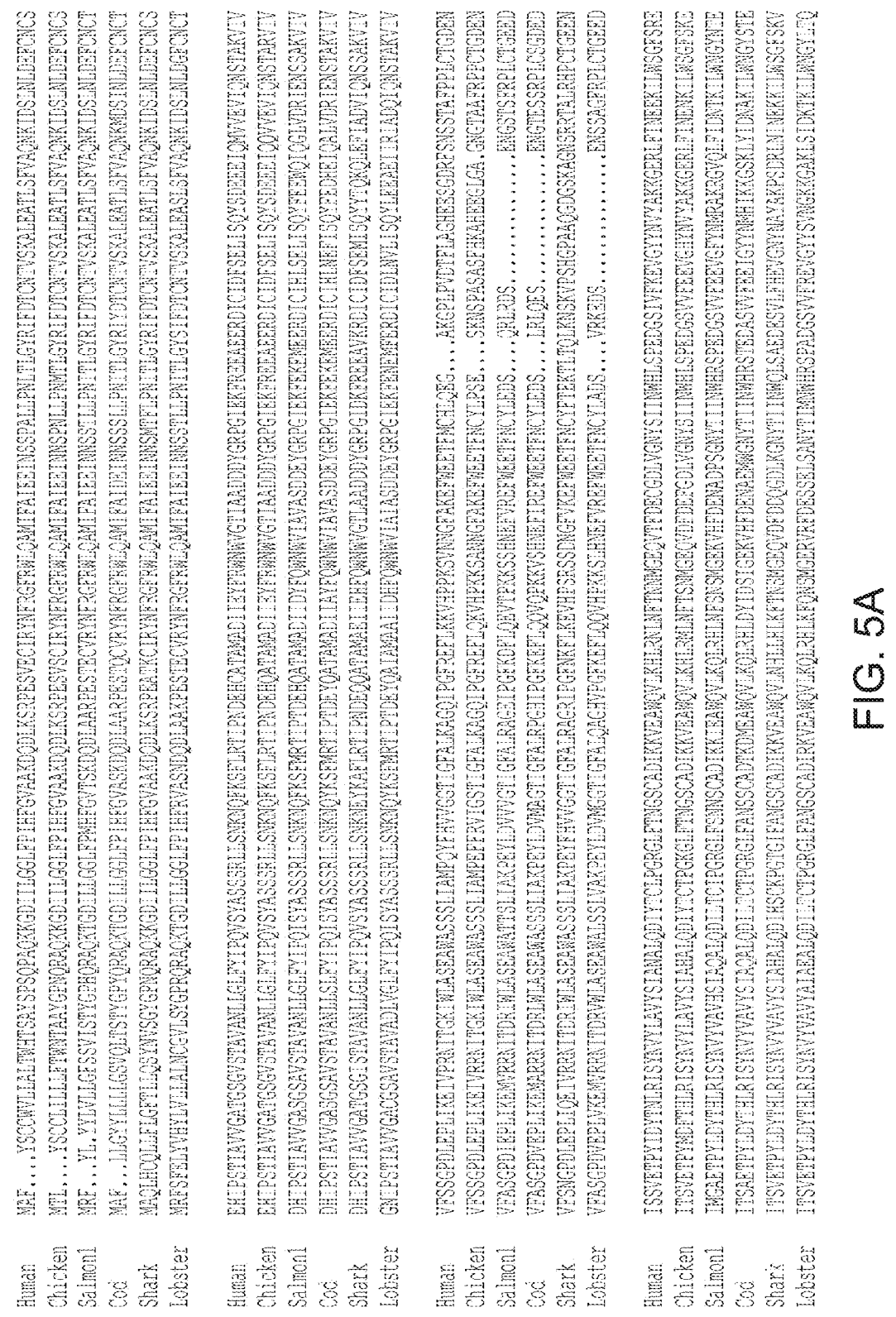
Figure 5B:
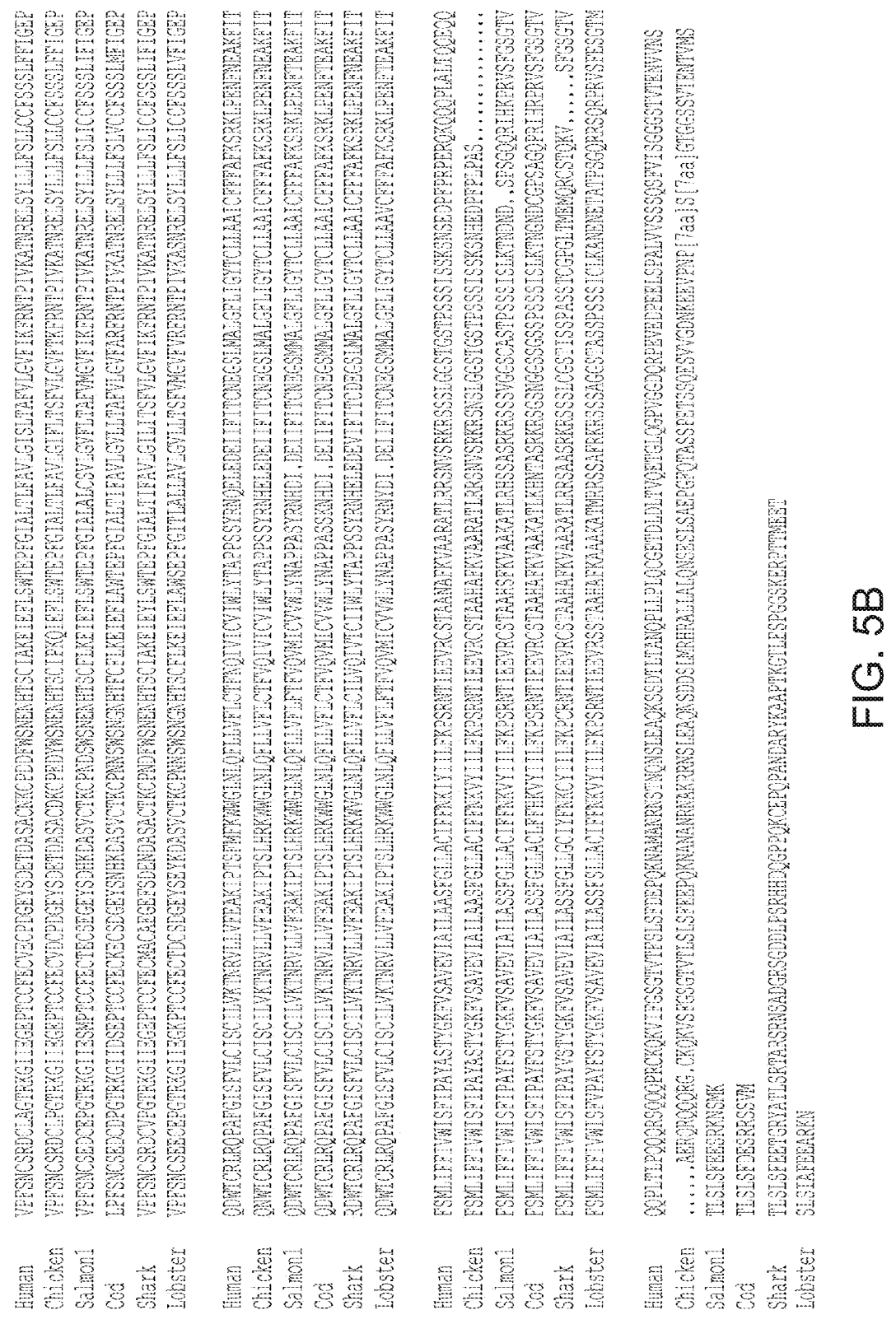

The putative amino acid sequence of the chicken jejunum CaSR protein was compared to CaSR proteins cloned from human parathyroid, salmon kidney, cod kidney, shark kidney and lobster genomic DNA by sequence alignment (FIG. 5A-B). All of these CaSR proteins display a high degree of homology and possess cysteine amino acids that have been demonstrated to be important in the overall structural characteristics of the CaSR molecule. Furthermore, the human and chicken CaSRs share a similar extended amino acid sequence that comprises a cytoplasmic domain in contrast to salmon, cod and lobster, which possess very short or truncated cytoplasmic domains by comparison. As shown at the bottom of FIG. 5, the cytoplasmic domain of the shark kidney calcium receptor is intermediate in length. Comparison of selected portions of the amino acid sequences for human and chicken CaSRs demonstrates that various antibodies that recognize specific domains on the human CaSR protein will likely recognize the corresponding domains on the chicken CaSR since their amino acid sequences in the region of antibody binding are identical.

Example 2

Chick Intestinal CaSR Protein Responds to Ca2+ Via Downstream Activation of the pERK Signal Transduction Pathway Materials and Methods Transfection of Chicken CaSR into HEK-293 Cells HEK-293 cells were plated into 6-well plates so that the cells were 90% confluent at the time of transfection. The linearized and non-linearized plasmids were ethanol precipitated and quantified spectrophotometrically. A ratio of DNA to lipofectamine of 1:3.5 (4 µg of DNA and 14 µl Lipofectamine 2000) was used for the transfection procedure. To provide a negative control, only Lipofectamine was added to some HEK cells. After exposure to lipofectamine, hygromycin B (400 µg/ml) was used to select for HEK cells that had been transfected since the plasmid containing the putative CaSR sequence also contained a hygromycin resistance element.

At the start of hygromycin selection, flasks were about 40% confluent. All flasks experienced a high percentage of die off cells. After an interval of 10 days, all the cells in the negative control flasks were dead. By contrast, the flasks with the non-linearized plasmid showed more colonies compared to the flasks with the linearized plasmid. Linear flask 1 and non-linear flask 1 were trypsinized by addition of 200 µl trypsin to redistribute dense colonies and prevent overcrowding 10 days after the start of hygromycin selection. New complete media was added containing 400 µg/ml hygromycin. At day 14, flasks had multiple colonies that were well spread out and were beginning to look overcrowded. Each flask was trypsinized, centrifuged and re-plated in a new flask, still under hygromycin selection. At day 17, transfected HEK cells were 60% confluent. On day 18, each flask was split into two flasks. All flasks were confluent two days later. One flask was harvested for immunoblotting analysis and the other was distributed into 4 vials per flask and frozen.

Results

To demonstrate that the open reading frame contained in the CaSR cDNA isolated from chick jejunum encodes a functional CaSR protein, the full-length cDNA clone described in Example 1 and FIGS. 2A-C was transfected into HEK cells and selected for HEK cells expressing protein derived from the cDNA using standard hygromycin B selection procedures. A series of cell colonies were identified that survived hygromycin B selection.

Figure 6:
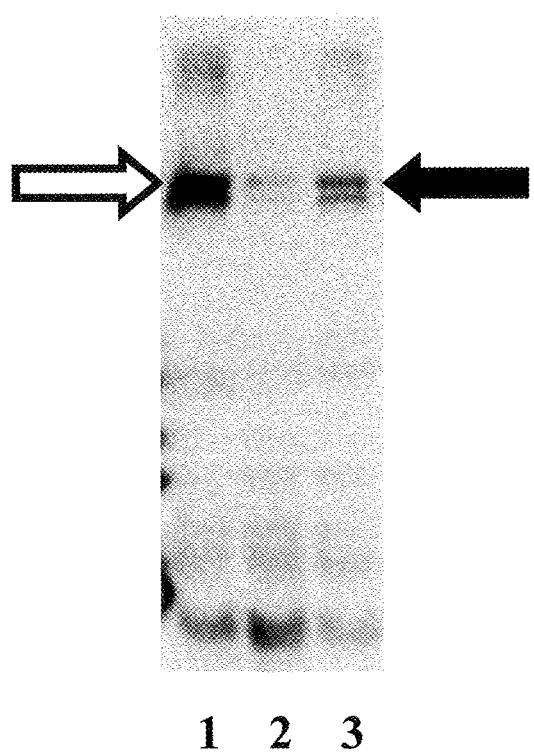
FIG. 6 is an immunoblot depicting the detection of CaSR proteins in HEK cell homogenates using a specific anti-CaSR antiserum. Lane 1: homogenate of HEK cells that were stably transfected with a human CaSR cDNA; Lanes 2 and 3: homogenates of HEK cells transfected with linearized chicken jejunum CaSR from two different transfection experiments. The open arrow indicates the position of a broad ~130 kD immunoreactive band in lane 1, while the black arrow indicates the position of two closely-spaced, similarly-sized immunoreactive bands in both lanes 2 and 3.
Figure 7A:
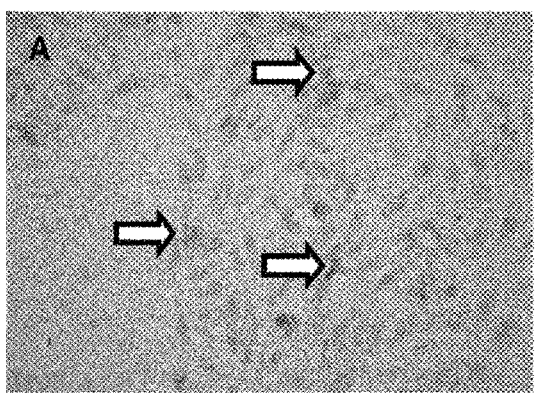
FIG. 7A is an image showing immunocytochemical staining of HEK cells that were transfected with a full length cDNA of chick intestinal CaSR using pre-immune serum. Damaged or dead cells that are nonspecifically labeled are indicated by the open arrows.
Figure 7B:
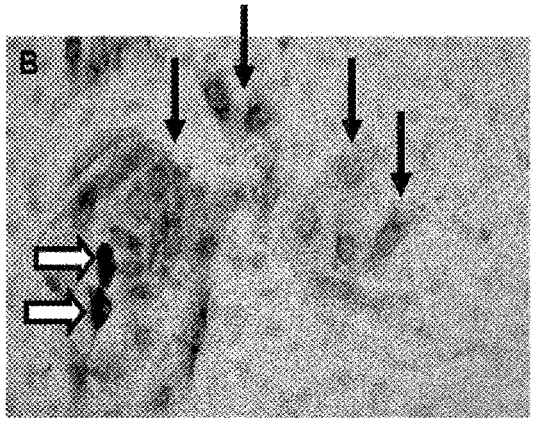
FIGS. 7B-D are images showing immunocytochemical staining of HEK cells that were transfected with a full length cDNA of chick intestinal CaSR using anti-CaSR antiserum. Downward pointing arrows indicate the presence of "nests" of cells that are labeled by anti-CaSR antiserum. Damaged or dead cells that are nonspecifically labeled are indicated by the open arrows.
Figure 7C:
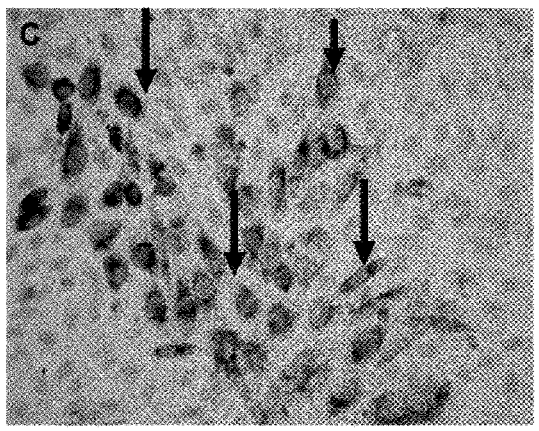
Figure 7D:
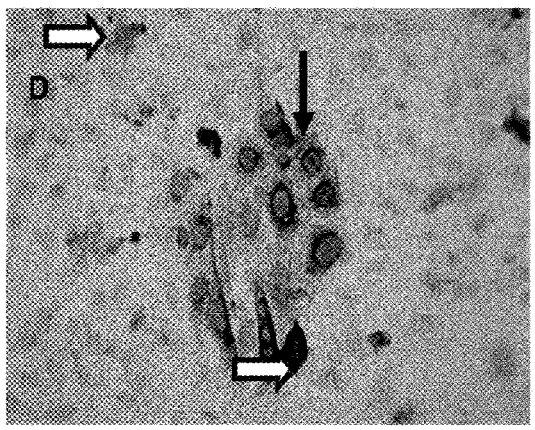

To demonstrate that recombinant CaSR proteins are expressed in transfected HEK cells, homogenates of HEK cells that had been either stably transfected with a human CaSR cDNA or HEK cells derived from two different transfections using linearized chicken CaSR cDNA were prepared and subjected to SDS-PAGE and immunoblotting using a specific anti-CaSR antiserum (FIG. 6). As shown by the rightward pointing open arrow in FIG. 6, cells expressing recombinant human CaSR protein displayed a broad immunoreactive band of ~130 kDa, which has been previously described. Similarly, homogenates derived from two different transfected HEK cell pools that were transfected with the chick jejunal CaSR cDNA each showed two closely spaced immunoreactive bands that co-migrate with the recombinant CaSR protein (see leftward pointing solid arrow in FIG. 6). These data demonstrate that HEK cells transfected with cDNA from the chick jejunum express recombinant chick CaSR protein that is recognized by specific anti-CaSR antiserum. These data are consistent with DNA sequence information that predicts that the size of the chicken CaSR protein should be nearly identical to that of human CaSR. Expression of chick intestinal CaSR in transfected HEK cells was also detected by immunocytochemistry (FIGS. 7A-D). Chick intestinal CaSR was strongly expressed by a few transfected cells in an manner identical to that of human parathyroid CaSR (FIGS. 7B-D).

Figure 8:
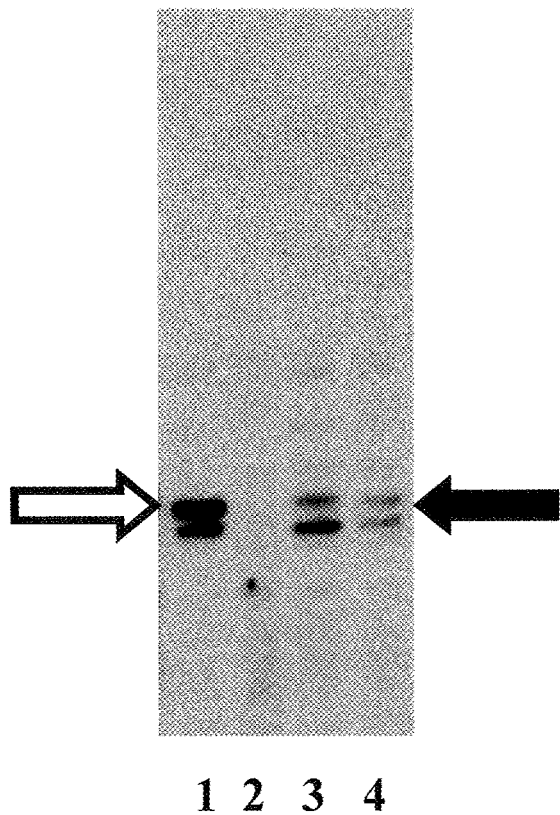
FIG. 8 is an immunoblot depicting the detection of phospho-ERK kinase in homogenates of HEK cells that were exposed to an increase in extracellular calcium using an antibody that is specific for phospho-ERK kinase, but does not recognize the dephosphorylated form of ERK kinase. Lane 1: HEK cells stably transfected with human CaSR cDNA and expressing recombinant human CaSR protein; Lane 2: HEK cells—non transfected control; Lane 3: HEK cells transfected with linearized chick jejunum CaSR cDNA and expressing recombinant chicken CaSR protein; Lane 4: HEK cells transfected with linearized chick jejunum CaSR cDNA in a different transfection experiment than those in Lane 3 and expressing recombinant chicken CaSR protein. Open arrow indicates phospho-ERK proteins in lane 1, while black arrow indicates phospho-ERK proteins in lanes 3 and 4.

Exposure of HEK cells transfected with the chick jejunal CaSR cDNA to an increase in extracellular Ca2+ ions (0.5 mM to 10 mM) produced selective activation of the extracellular regulated kinase (ERK) kinase pathway, as demonstrated using a phospho-ERK-specific antibody that does not recognize the dephosphorylated form of the ERK kinase (FIG. 8). To perform this experiment, CaSR-transfected HEK cells or untransfected HEK cells previously bathed in media containing 0.5 mM Ca2+ were then exposed to an increase in extracellular Ca2+ to 10 mM. Cells were then processed for immunoblotting and membranes probed with antibody specific for phospho-ERK. Cell fractions from HEK cells transfected with either human CaSR (rightward pointing open arrow) or two different HEK cell colonies expressing the chicken CaSR protein (left pointing solid arrow) contained phospho-ERK proteins. By contrast, untransfected HEK cells exposed to the same increase in extracellular Ca2+ showed no immunoreactivity with the anti-phospho-ERK antibody (downward pointing open arrow with asterisk). Taken together, the data shown in FIGS. 6-8 demonstrate that the transfected HEK cells express the chick jejunal CaSR protein and that this recombinant CaSR protein is able to respond to increases in extracellular Ca2+ via activation of appropriate downstream signaling pathways including phosphor-ERK.

Example 3

CaSR mRNA and Protein are Expressed in the Intestine of Chickens During Various Developmental Stages Materials and Methods
Northern Blot Analysis
Intestinal and kidney tissues were harvested from 3 several week old chicks and rinsed in RNA later (Ambion) after harvest. Epithelial cells were scraped from the mucosal surface of each respective intestinal segment and transferred immediately to Stat 60. Total RNA was isolated from the prep on the same day. To isolate poly A+ RNA, the MicroPoly (A) purist kit (Ambion) was used and the resulting poly-A RNA was quantified and precipitated overnight for use in Northern blot analysis the following day. The mRNA was fractionated using the NorthernMax formaldehyde-based system and a 1% agarose gel that was electrophoresed at 120 volts for 1 hour and 50 minutes. Subsequently, the contents of the gel were transferred to a BrightStar membrane for 2.5 hours using a downward transfer assembly and probed using $^{32}$P-labeled CaSR cDNA cloned from chick jejunum as described in Example 1.

Immunocytochemistry
Immunocytochemistry was performed on formaldehyde fixed and deparaffinized sections of intestine from 10 week old chicks using anti-CaSR specific antiserum. After de-paraffinization, tissues sections were incubated in a blocking solution to prevent nonspecific binding and then incubated for 2 hr or overnight in a solution containing either anti-CaSR antiserum or its corresponding pre-immune antiserum obtained from the same animal species. After incubation, the sections were rinsed with buffer to remove primary antisera and then incubated with secondary immune antiserum that will bind to and detect the presence of bound primary antibody at specific locations within the tissue section. After rising the excess secondary antiserum, the section was incubated in a color development reagent that localizes to the location and presence of bound antibody. Sections were then mounted and examined using standard microscopy techniques.

Results
To evaluate CaSR mRNAs expressed within chick intestine, poly A+ RNA from various segments of chick intestine was isolated, fractionated and probed with $^{32}$P-labeled full length chick intestinal CaSR isolated from 22 day old chick jejunum by Northern blotting (FIGS. 9A and B). A CaSR transcript that appears to co-migrate with the major CaSR mRNA transcript present in chick kidney was detected in proximal, middle and distal intestinal segments of chicks that appears to co-migrate with the major CaSR mRNA transcript present in chick kidney (see solid arrows in FIG. 9A). However, due to the much lower content of CaSR mRNA in intestinal tissue relative to kidney tissue, it appears that the level of steady state expression of CaSR mRNA in the intestine may be lower the intestine than the kidney and perhaps even the parathyroid.

Figure 10:
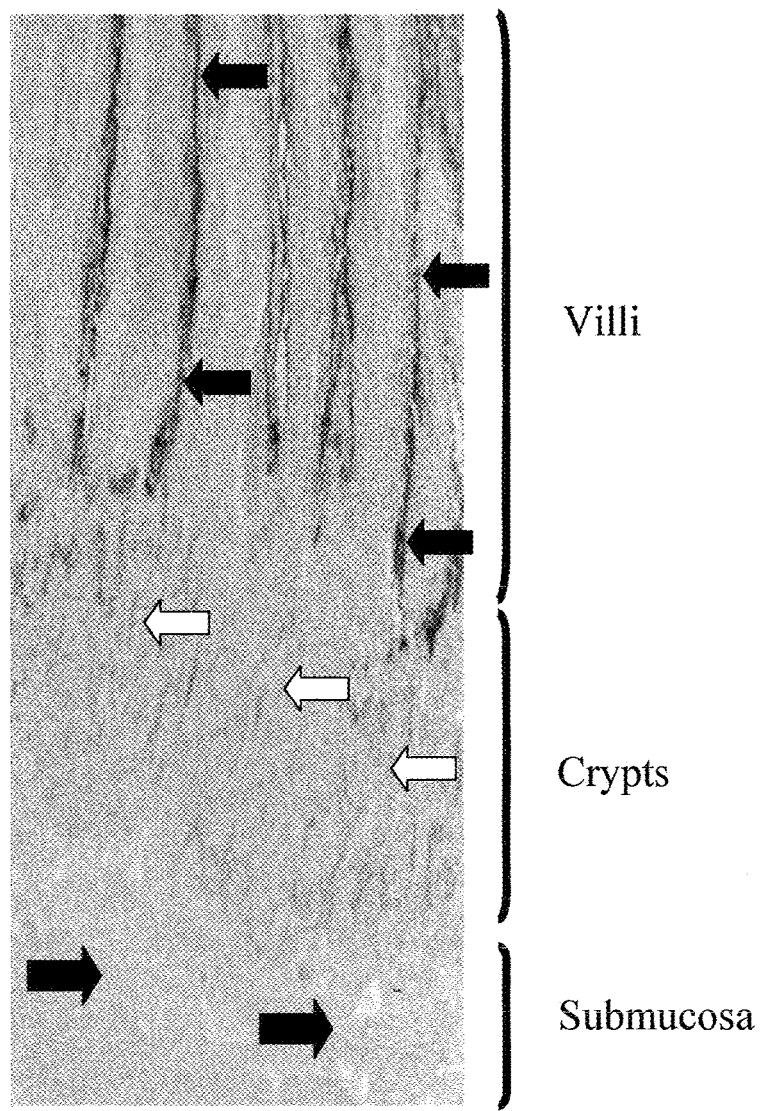
FIG. 10 is an image depicting immunolocalization of CaSR protein in a section of proximal intestine from a 10 week old chicken using anti-CaSR antiserum. The left-pointing solid arrows indicate localization of CaSRs in the mucosal layer of the intestine while the open arrows show CaSR protein in the area of the crypts. The right-pointing solid arrows indicate the absence of significant CaSR staining in the area of the submucosa.

To determine the location of CaSR protein in the proximal intestine of the developing chick, CaSR protein was localized to the epithelial cells of the mucosa and crypt areas by immunocytochemistry (FIG. 10). The location of the CaSR protein within the intestinal epithelia allows for it to be in contact with luminal sources of nutrients and ions that are ingested by the chick as well as being expressed by cells in the crypt area of the intestine where replacement and turnover of epithelial cells in the mucosa occur. From its location in crypts, CaSR may influence the overall trophic response of the chick intestine to the presence of nutrients and ions. Significant CaSR staining was not detected in the underlying submucosa (see bottom of FIG. 10).

The intestinal segments of chicks of various ages were also analyzed for the presence of CaSR protein using immunocytochemistry. As shown in FIG. 11A, CaSR protein is not very abundant in chicks immediately after hatching. As noted by the arrows, CaSR protein in the proximal intestine is localized to the epithelial cells (FIG. 11A), while CaSR protein in the distal intestine is localized to mucus cells (FIG. 11B). It is apparent by the intensity of the CaSR staining that the proximal intestines of older chicks (5 days and 10 weeks) (FIGS. 11C and D) express much more CaSR protein than newly hatched chicks. These data suggest that a significant increase in CaSR protein expression occurs after the chick has hatched.

Example 4

Figure 12:
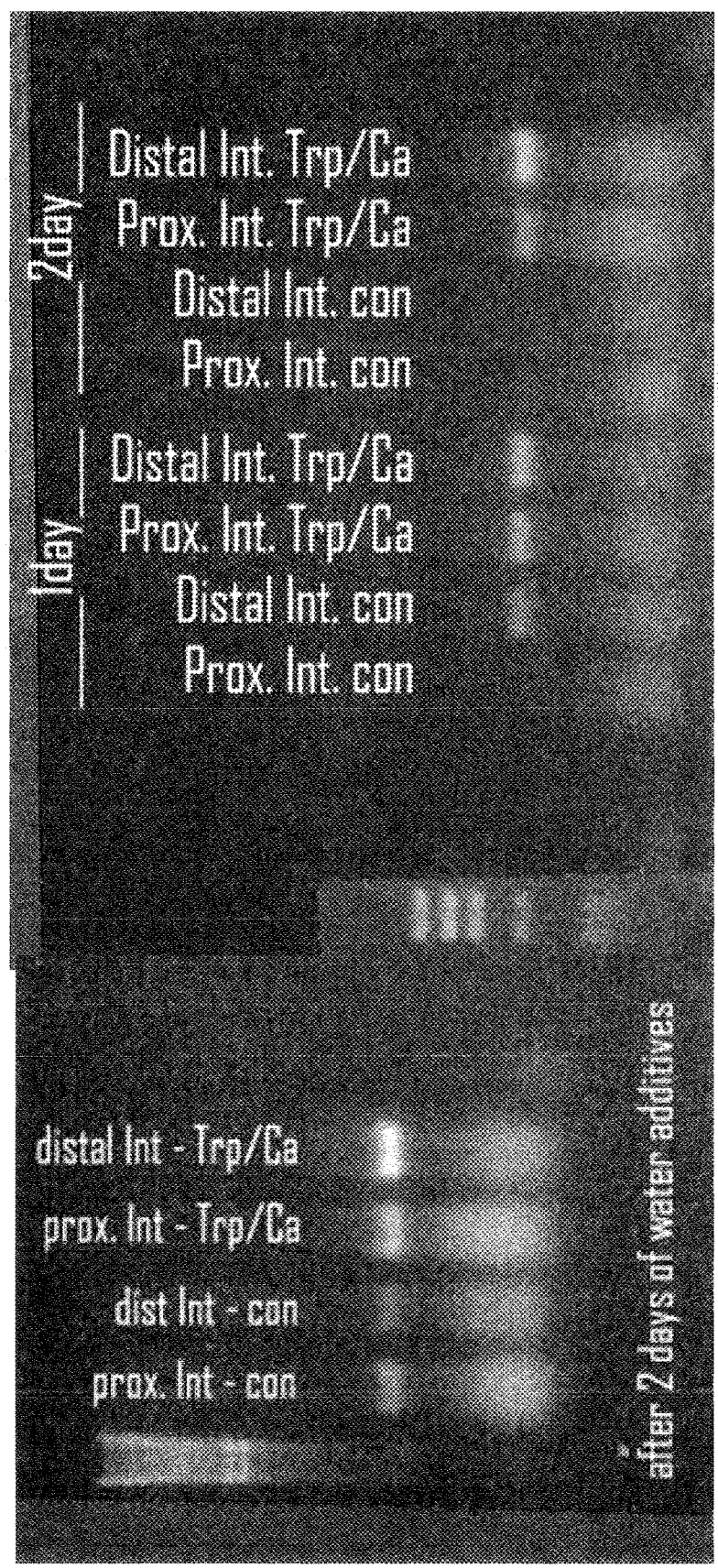
FIG. 12 is an image of an electrophoretic gel showing steady state CaSR mRNA levels, as measured by PCR, in the proximal intestine (Prox. Int.) or distal intestine (Distal Int.) of newly hatched chicks that were given water with no added CaSR modulators (con), or water to which the CaSR modulators calcium and tryptophan were added (Trp/Ca) for 1 or 2 days.
Figure 13A:
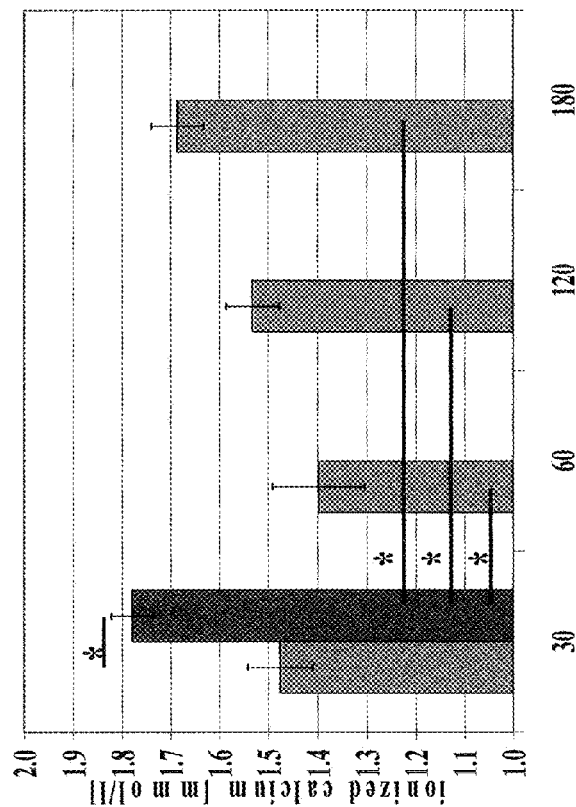
FIG. 13A is a bar graph depicting plasma calcium levels (Y-axis) in two week old male chicks that were gavaged either with a single 3 mg dose of MC 0100 at various intervals of time after gavage (X-axis). Asterisks indicate a significant difference in mean value as compared to the control.
Figure 13B:
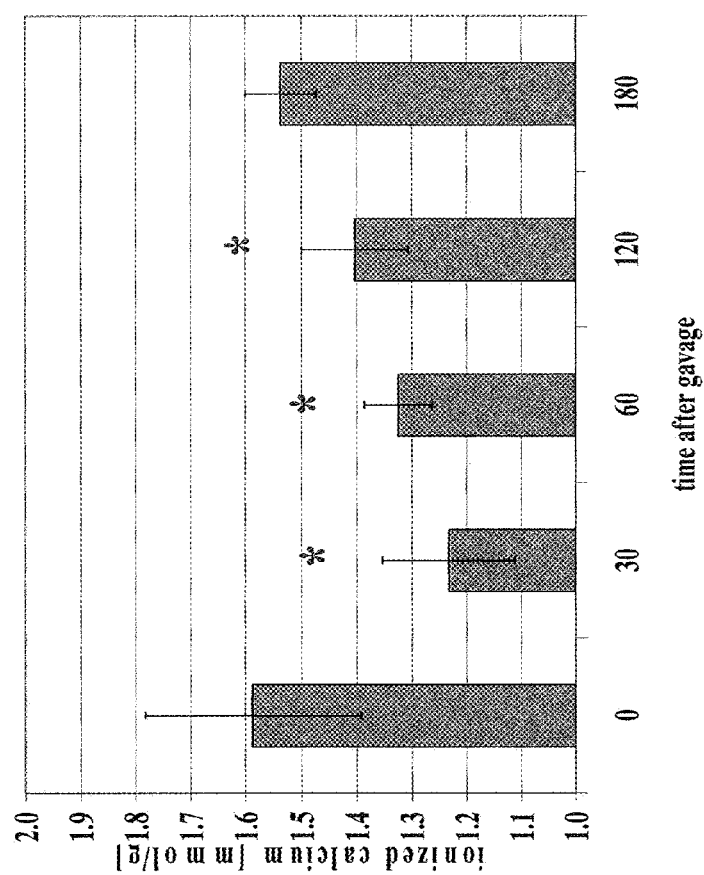
FIG. 13B is a bar graph depicting plasma calcium levels (Y-axis) in two week old male chicks that were gavaged either with a single 3 mg dose of MC 0100, or water alone, at various intervals of time after oral gavage (X-axis). Asterisks indicate a significant difference in mean value as compared to the control.
Figure 14:
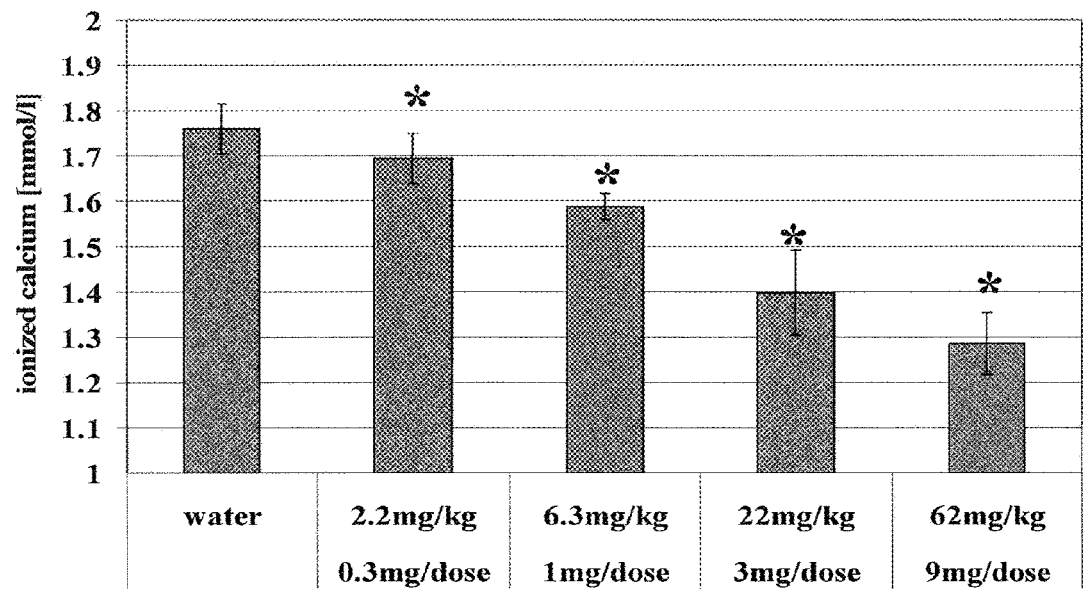
FIG. 14 is a bar graph from a dose response study depicting plasma calcium levels (Y-axis) in two week old chicks that were gavaged with different doses of MC 0100 or water alone. Asterisks indicate a significant difference in mean value as compared to water the control.
Figure 15A:
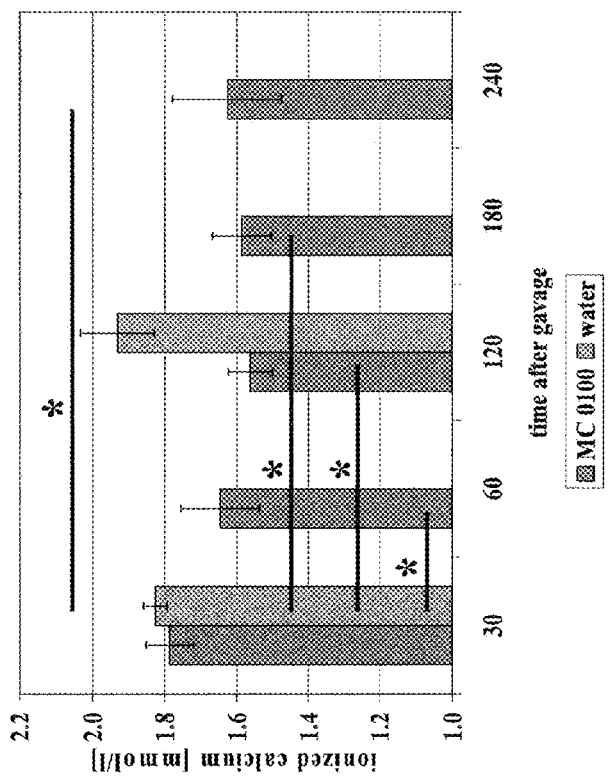
FIGS. 15A and B are bar graphs from a dose response study depicting plasma calcium levels (Y-axis) in newly hatched chicks at various times after oral gavage with a single 1 mg dose of MC 0100 or water alone. Asterisks indicate a significant difference in mean value as compared to the control.
Figure 15B:
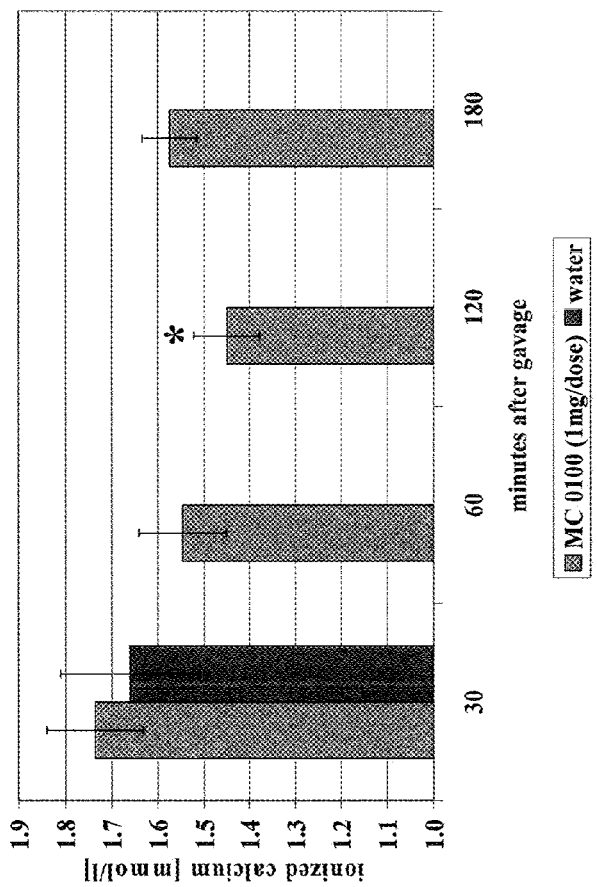
Figure 16:
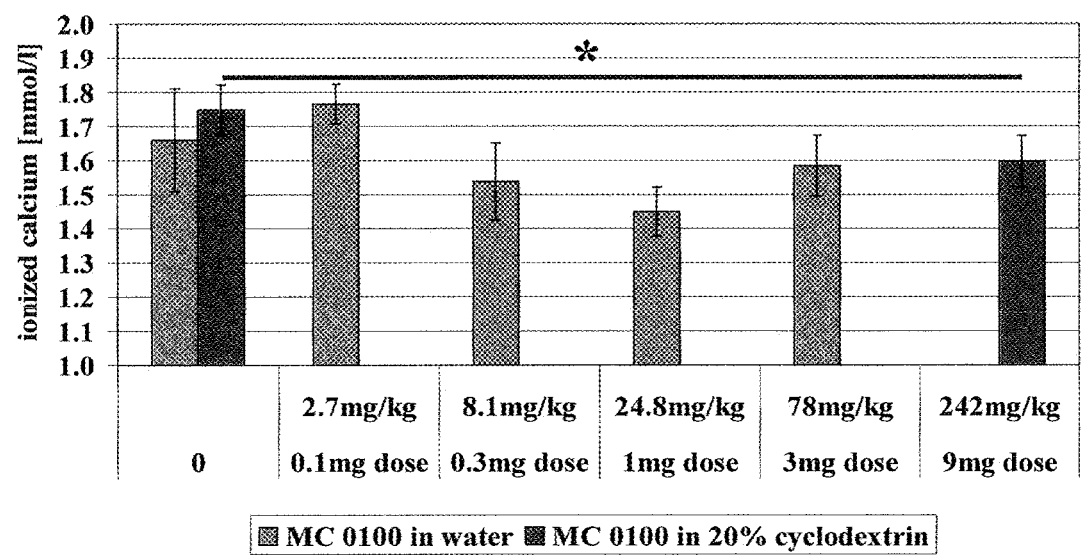
FIG. 16 is a bar graph from a dose response study depicting plasma calcium levels (Y-axis) in newly hatched chicks two hours after a 0.25 ml oral gavage with different doses of MC 0100 in water or 20% cyclodextrin carrier. Asterisks indicate a significant difference in mean value as compared to water the control.
Figure 17:
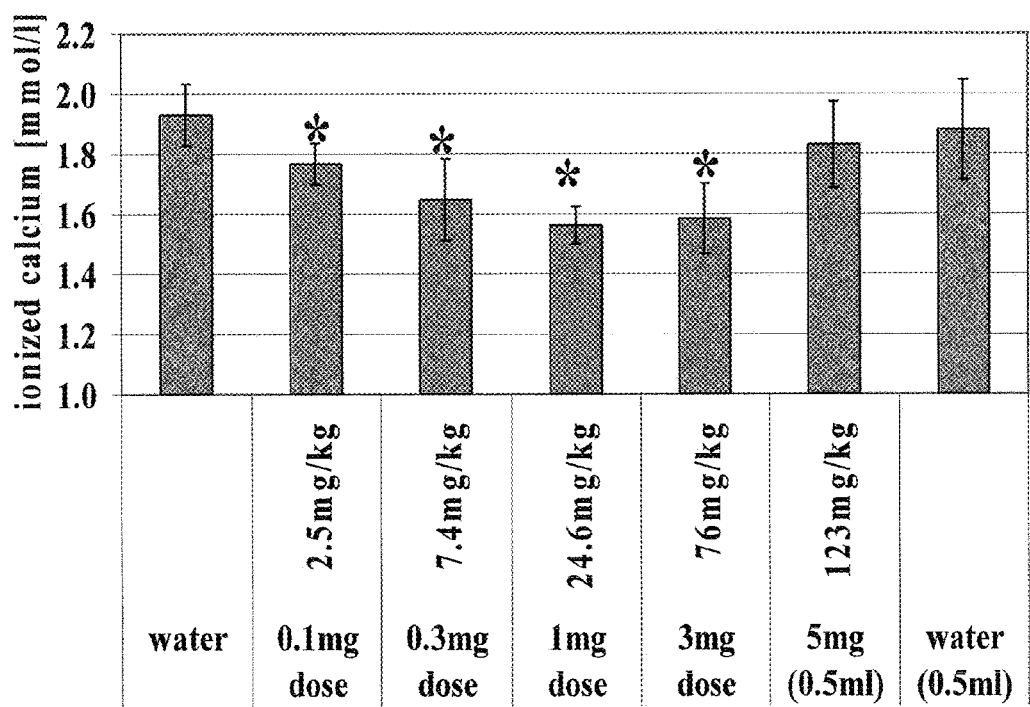
FIG. 17 is a bar graph from a dose response study depicting plasma calcium levels (Y-axis) in two week old chicks two hours after a 0.25 ml oral gavage with different doses of MC 0100 or water alone. Asterisks indicate a significant difference in mean value as compared to water the control. The highest dose included the use of cyclodextrin carrier that again interfered with the action of MC 0100.

Addition of CaSR Modulators to the Drinking Water of Newly Hatched Chicks Increases the Expression of CaSR mRNA in their Intestinal Tissue Materials and Methods
mRNA Expression
Newly hatched chicks were divided into two groups. One group was provided standard water and feed, while the second group was provided drinking water that was supplemented with the known CaSR agonists calcium and tryptophan, and standard feed. After various intervals (days 1 and 2), chicks were sacrificed and RNA was prepared from both proximal and distal intestinal segments. Using standard techniques, cDNA was prepared from the RNA and a 653 bp sequence of CaSR mRNA was selectively amplified using PCR and conditions identical to those described in Example 1 above.
Gavage
Male chicks (either newly hatched or 2 weeks of age) were gavaged with a single application of various doses of the specific CaSR modulator (MC 0100), a specific pharmacological modulator of CaSRs, to increase the apparent sensitivity of the CaSR to agonists such as calcium. An increase in the apparent sensitivity of the chick CaSR to extracellular calcium is expected to result in the "resetting" of the normal range of calcium within the chick to a lower level of plasma calcium since the functioning CaSR are all shifted leftward (more sensitive) on the dose response curve of CaSR for calcium.
Results
The addition of a combination of calcium and tryptophan to the drinking water of newly hatched chicks produced a significant increase in steady state CaSR mRNA, as measured by PCR (FIG. 12). As the diet of newly hatched chicks is primarily carbohydrate-based, the inclusion of specific CaSR agonists in the drinking water or diet of newly hatched chicks may allow for increased expression of CaSR protein and/or mRNA, leading to a variety of possible beneficial effects including growth, feed conversion, immunity, improved nutrient and ion absorption, as well as intestinal resistance to parasites or bacterial diseases.

To further demonstrate that CaSR proteins in chicks and chickens provide critical nutrient and ion sensing capabilities, as has been demonstrated in humans, newly hatched and 2 week old chicks were subjected to bolus treatments of MC 0100, a specific CaSR modulator that has been well characterized and is known to increase the sensitivity of CaSRs to changes in extracellular calcium. As shown in FIGS. 13-17, a single gavage treatment of both 2 week old (FIGS. 13 and 14) and newly hatched (FIGS. 15-17) chicks with various doses of the CaSR modulator produced an expected dose dependent decrease in plasma calcium after various intervals of time. These data demonstrate that CaSRs in chicks can be modulated to produce physiological changes in that include alterations in plasma calcium.

Example 5

CaSRs are Expressed in Epithelial Cells Lining Various Gastrointestinal Tissues of Developing Pigs Materials and Methods Stomach and duodenum tissue samples were obtained from a female weaned piglet (9 hours) of 11.5 lbs. at day 15-16. Immunocytochemistry (ICC) was performed using anti CaSR antibody (4641) at 1:500 dilution as described above.

Results

Figure 18A:
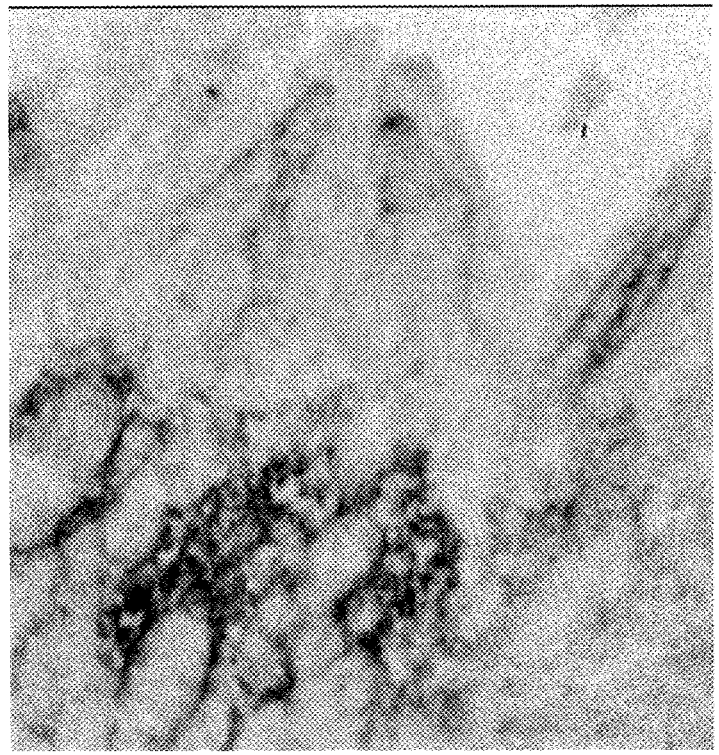
FIGS. 18A and B are images of fetal pig gastrointestinal tissue that show localization of CaSR protein (see rose-colored reaction product and arrows) to epithelial cells lining mucosal surfaces of the intestine, as determined by immunocytochemistry using anti-CaSR antibody.
Figure 18B:
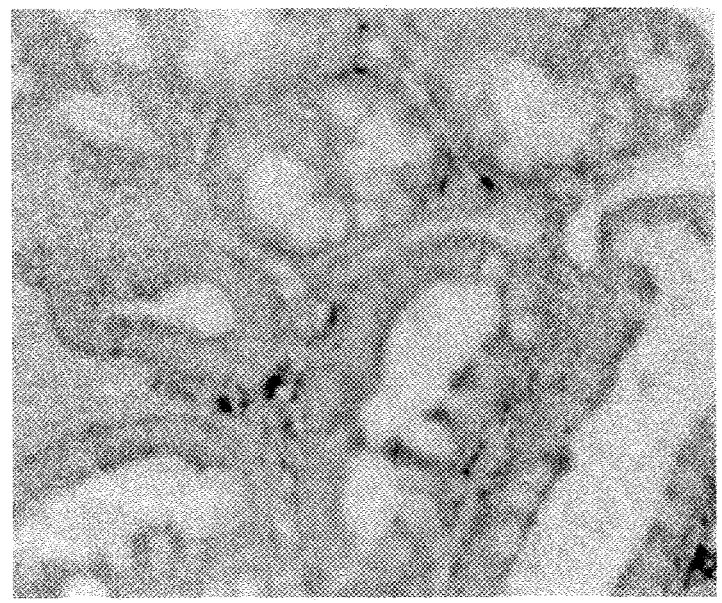
Figure 19A:
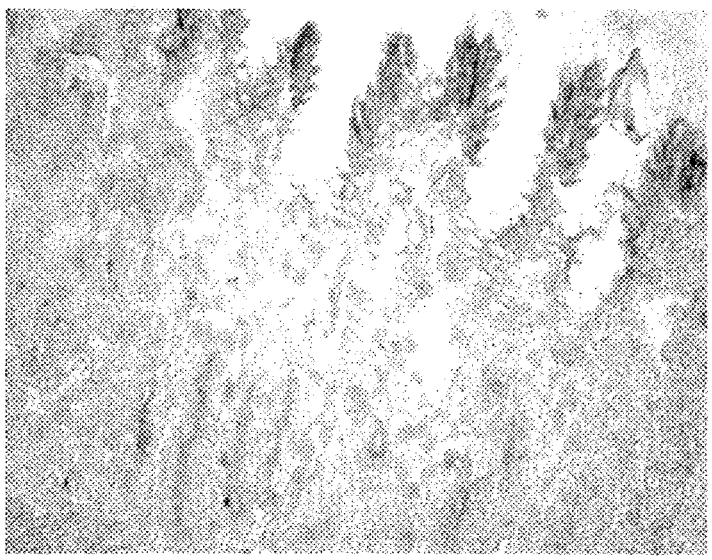
FIG. 19A is a tissue section of the antrum from a 15-16 day old female piglet after 9 hours of weaning, which shows localization of CaSR protein, as determined by immunocytochemistry using anti-CaSR antibody.
Figure 19B:
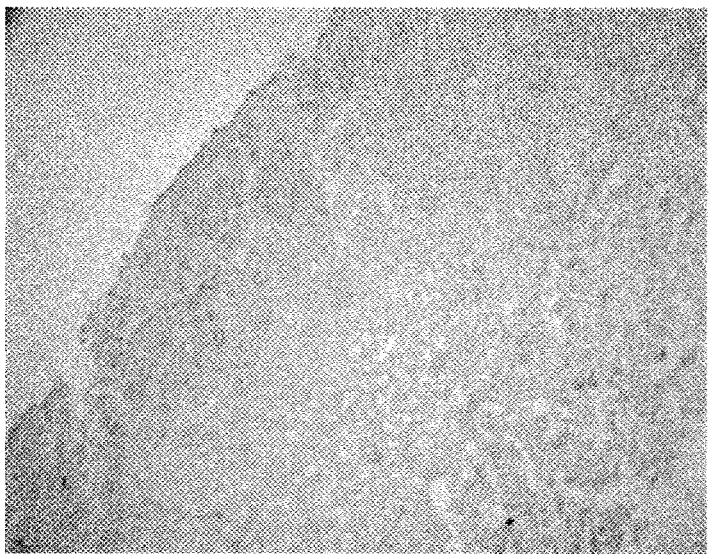
FIG. 19B is a tissue section of the pyloric region of the stomach of a 15-16 day old female piglet after 9 hours of weaning, which shows localization of CaSR protein (see rose-colored reaction product) as determined by immunocytochemistry using anti-CaSR antibody. The lumen of the stomach is the space at the left of the panel.
Figure 19C:
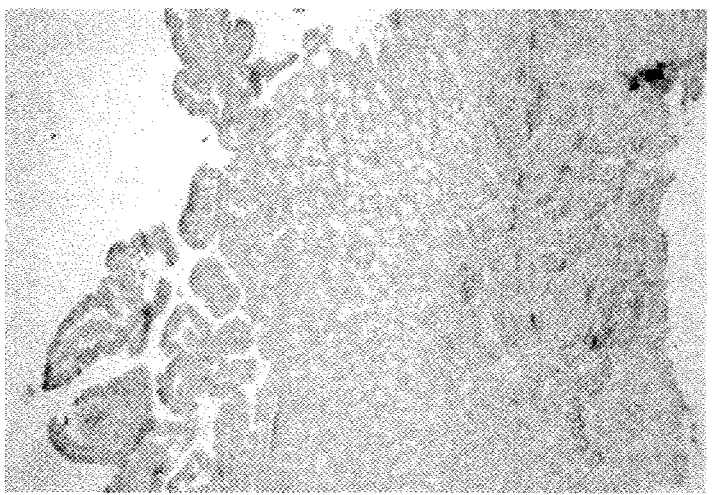
FIG. 19C is a tissue section of the duodenum of a 15-16 day old female piglet after 9 hours of weaning, which shows localization of CaSR protein, as determined by immunocytochemistry using anti-CaSR antibody. The lumen of the stomach is the space at the left of the panel.

To determine whether epithelial cells lining the intestine of fetal pigs express CaSR protein on their mucosal or serosal surfaces, immunolocalization of CaSR was performed using standard techniques. As shown in FIGS. 18A and B, epithelial cells lining the pig gastrointestinal tract express significant amounts of CaSR protein on the mucosal surface of the intestine. CaSR protein was also detected in the epithelial cells lining the antrum (FIG. 19A), stomach (FIG. 19B) and first segment of the intestine (duodenum) (FIG. 19C) of piglets that were weaned from sow's milk only 8 hr previously, thereby demonstrating that CaSR proteins are expressed in stomach and intestinal epithelial cells that are exposed to new dietary substances in piglets.

Example 6

Figure 20A:
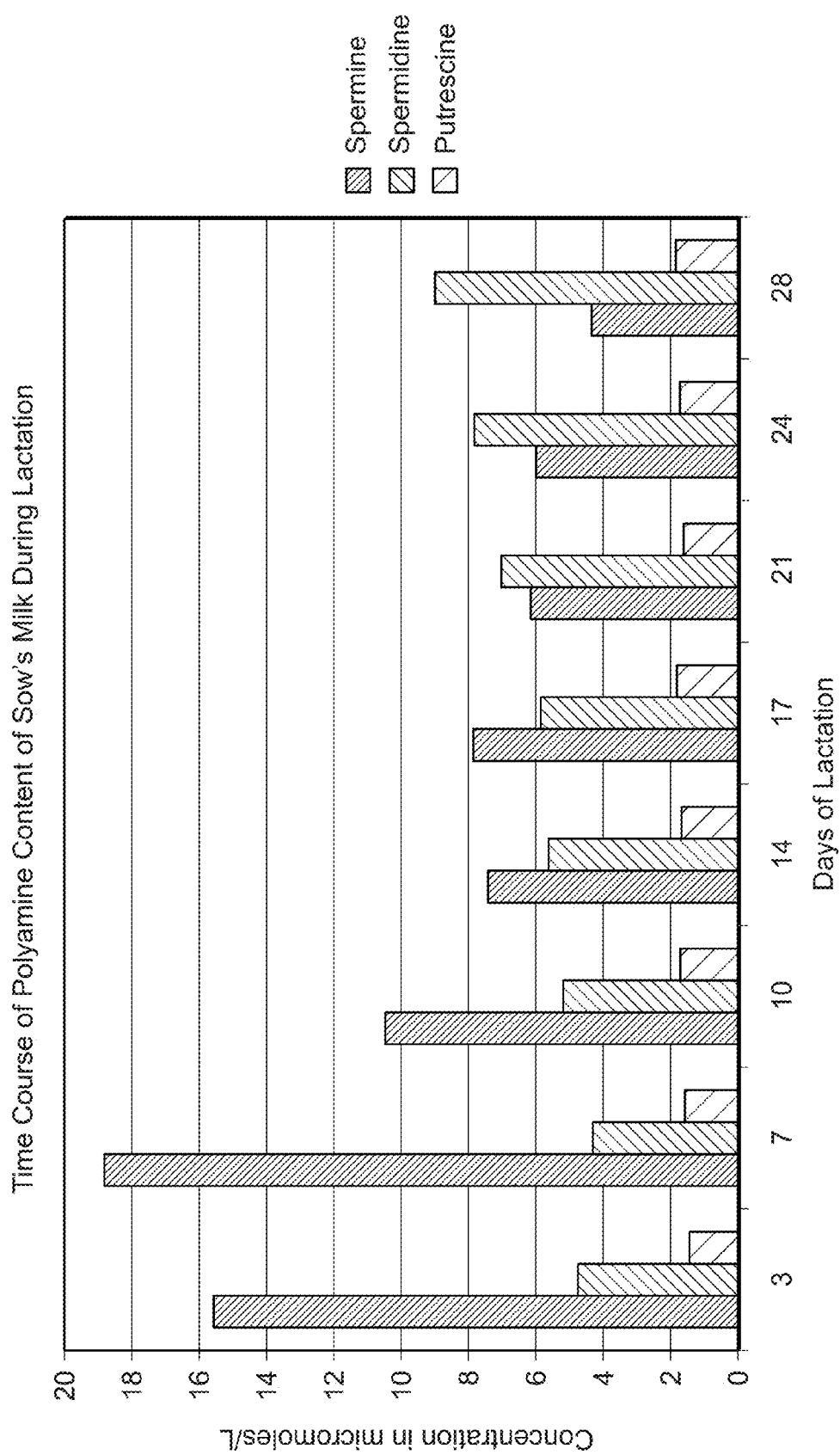
FIG. 20A is a bar graph depicting the concentration of the polyamines spermine, spermidine and putrescine in sow's milk at various time points during lactation.

CaSRs Present in the Intestinal Epithelia of Developing Pigs can be Stimulated by Various CaSR Agonists Background Under normal conditions, newborn piglets receive most of their nutrition via the ingestion of milk from their mothers. Published reports (Cheng et al., *Animal Sci.* 82: 95-99 (2006)) of the composition of sow colostrum and milk demonstrate that they are both rich in CaSR agonists and possess an ionic composition that would allow for the stimulation of CaSRs. As shown in FIG. 20A (adapted from Cheng et al.), colostrum and milk samples obtained during the early stages of milk production contain a high content of spermine, a potent CaSR agonist. Although the spermine content of milk decreases as days of lactation increase, the concentration of another potent CaSR agonist, spermidine, increases. As shown in FIG. 20B, the ionic composition of sow's milk and colostrum also favor the activation of CaSRs located in the suckling pig's intestine and stomach via CaSR agonists that are contained in the milk. The low concentration of Na+ ions coupled with the high concentration of Ca2+ ions present in sow's milk has been demonstrated to promote the activation of CaSRs using recombinant CaSR protein expression studies in HEK cells (Quinn, S M, C-P Yee, R. Diaz, O. Kifor, M. Bai, P. Vassilev and E Brown. *Am. J. Physiol.* 273:1315-1323, 1997). The elevated concentrations of calcium present in sow's milk provide for enhanced stimulation of CaSRs by spermine at concentrations that correspond to these found in sow milk (FIG. 20C).

Upon the weaning of nursing animals, the nutrient source that will maintain both the growth of the neonatal animal and its intestinal tissue will be exogenous food sources. Thus, the transition from milk to solid or semisolid food that occurs upon the weaning of animals is important to the future success and agriculture performance of the animals.

The milk of animals like swine and cows contain high quality nutrient proteins like casein. These nutrient proteins are acted upon by the enzymatic machinery of the gastrointestinal tract of young developing animals, and peptides derived from the hydrolysis of proteins contact the mucosal surface of the stomach and intestine. These proteins, peptides and amino acids are absorbed across the intestinal epithelial to be used as nutrients.

Materials and Methods

All methods and equipment utilized to perform experiments on HEK cells have been reported previously (Gama, L. and Breitwieser, G. E. 1998. A carboxyl-terminal domain controls the cooperativity for extracellular Ca2+ activation of the human calcium sensing receptor. A study with receptor-green fluorescent protein fusions. *J. Biol. Chem.* 273, 29712-29718; Bai, M., Quinn, S., Trivedi, S., Kifor, O., Pearce, S. H., Pollak, M. R., Krapcho, K., Hebert, S. C. and Brown, E. M. 1996. Expression and characterization of inactivating and activating mutations in the human Ca2+o-sensing receptor. *J. Biol. Chem.* 271, 19537-19544). Untransfected HEK cells or, alternatively, cells transfected and expressing CaSR protein were cultured in Dulbecco's Modified Eagle Medium containing 10% fetal bovine serum and 1% penicillin-streptomycin in 75 $cm^2$ flasks until they reached confluence. Media was removed from the flasks and cells were loaded by exposure to Loading Buffer (125 mM NaCl, 4 mM KCl, 1.0 mMCaCl$_2$, 1.0 mM MgCl$_2$, 1 mM NaH$_2$PO$_4$, 20 mM HEPES, 1 gm/liter bovine serum albumin, and 1 gm/l glucose, pH ~7.4, osmolality ~285) containing 4.1 micromolar FURA2-AM (Molecular Probes Inc. Eugene, Oreg.) for 2 hr. Cells were then scraped from the surface of the flask using a standard cell scraper (Costar 3010, Corning Inc.). Cells were then pelleted from the suspension by low speed centrifugation to remove loading buffer and rinsed twice to remove extracellular FURA2 dye by two sequential suspensions and pelleting steps using low speed centrifugation. Immediately prior to the start of the experiment, cells were resuspended in various experimental buffers for analyses as described below. The Standard Experimental Buffer used for many studies was composed of: 125 mM NaCl, 4 mM KCl, 0.5 mMCaCl$_2$, 0.5 mM MgCl$_2$, 20 mM HEPES, 1 g/l glucose, pH ~7.4, osmolality ~285. All other buffers were variations on this basic composition where specific components within the Standard Experimental Buffer were varied while the remaining components were held constant.

Cell suspensions consisting of a total volume of 3 ml were analyzed in a PTI fluorimeter (PTI Model 814 Photomultiplier Detection System equipped with SC-500 Shutter Controller and PTI Driver and Analysis Software) within approximately 20 min after exposure to experimental buffers. Data was acquired using standard ratio image analysis as described previously using a data acquisition rate of 1.3 sec. for 500 or 1000 second intervals.

In selected experiments, the detergent Triton X-100 was added in order to lyse the cells and quantify differences in FURA2 ratio fluorescence. Triton X-100 was added to the cells to obtain a maximal fluorescence signal from the FURA2 for purposes of quantification.

Results

Figure 21A:
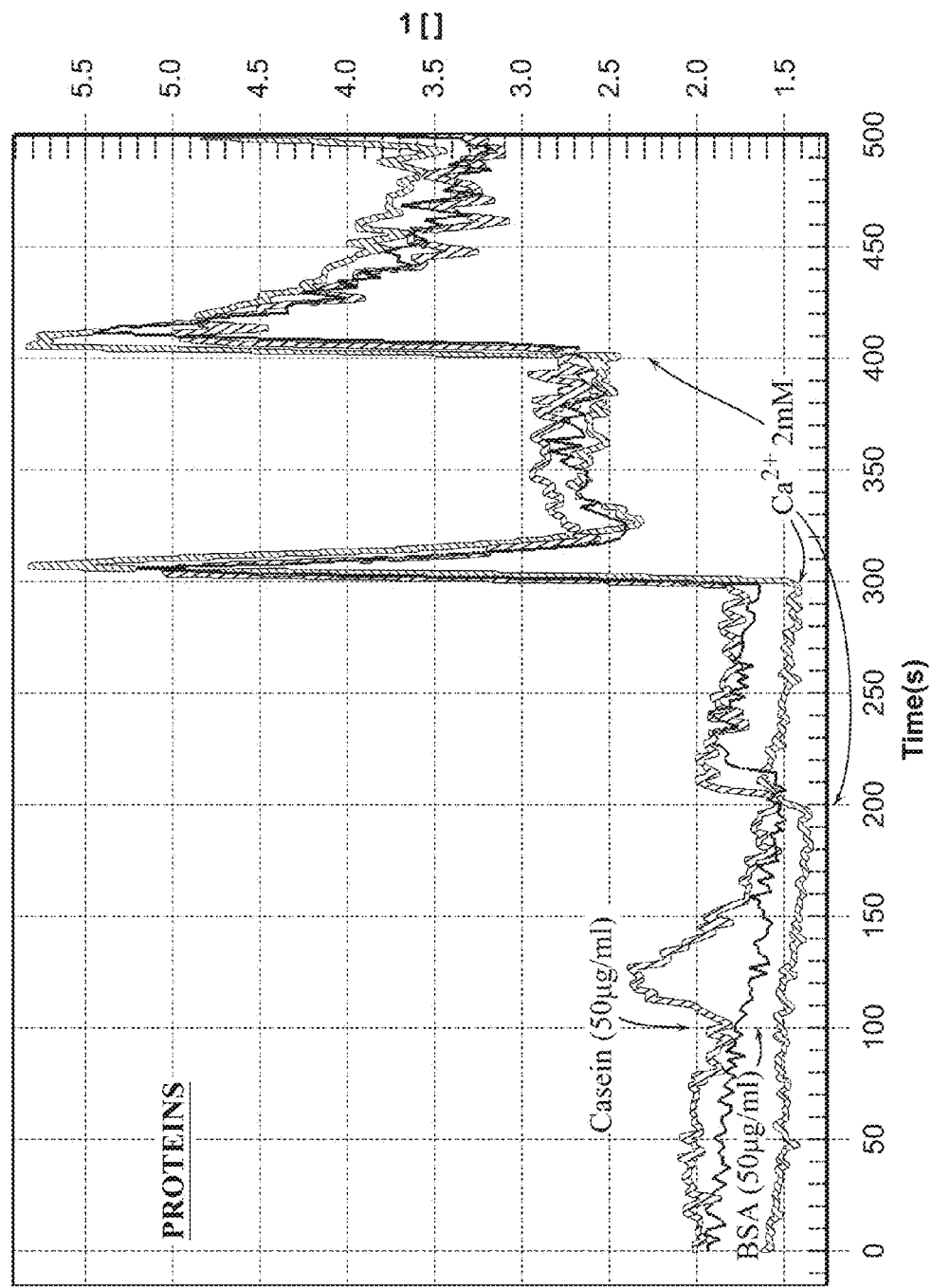
FIG. 21A is a graph depicting the effect of casein and bovine serum albumin (BSA) on activation of recombinant human CaSR protein expressed in HEK cells.
Figure 21B:
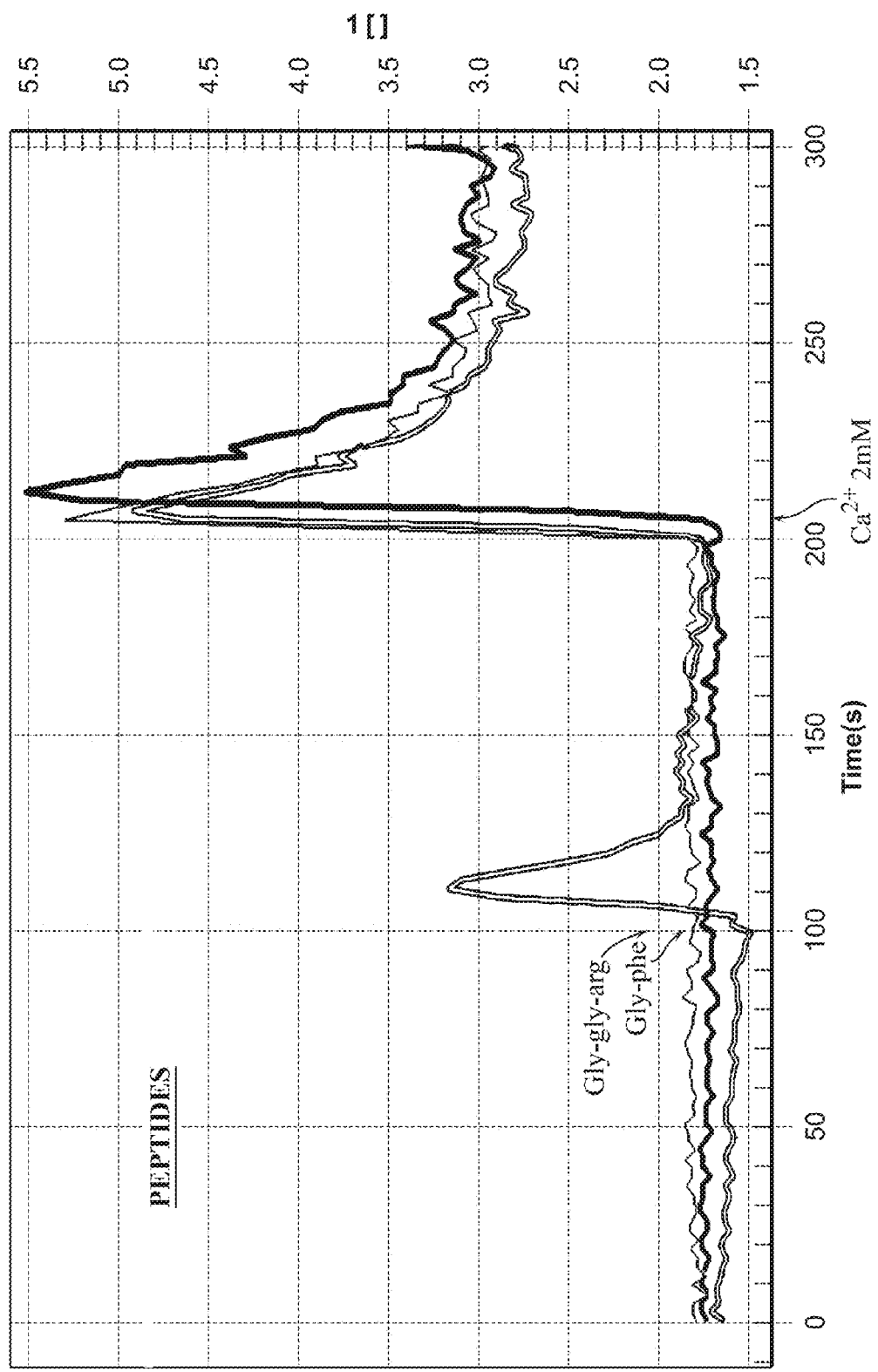
FIG. 21B is a graph depicting the effect of the peptides glycine-glycine-arginine (gly-gly-arg) and glycine-phenylalanine (gly-phe) on activation of recombinant human CaSR protein expressed in HEK cells.
Figure 22:
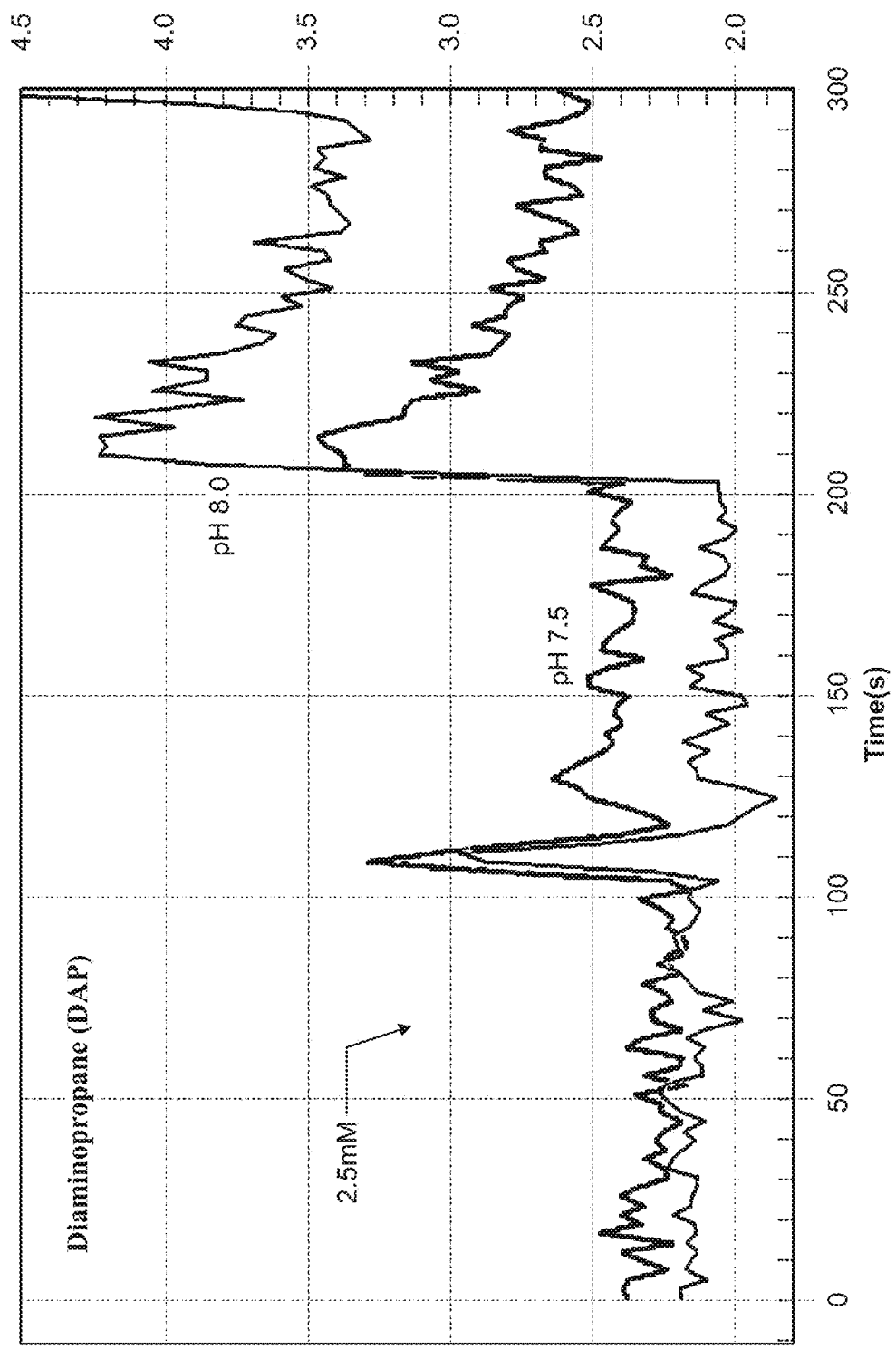
FIG. 22 is a graph depicting the effect of diaminopropane, a small positively charged organic molecule, on activation of recombinant human CaSR protein expressed in HEK cells.

Casein, a calcium binding protein and constituent of milk, acts as an agonist to recombinant human CaSR protein expressed in HEK cells (FIG. 21A), while bovine serum albumin (BSA), a protein that also binds calcium, has no effect on human CaSR. Similarly, the tripeptide glycine-glycine-arginine (gly-gly-arg) produced a significant activation of recombinant human CaSR protein while exposure of the CaSR to the dipeptide, glycine-phenylalanine (gly-phe), does not activate the CaSR under identical extracellular ionic conditions (FIG. 21B). Furthermore, exposure of recombinant human CaSR to diaminopropane, a small positively charged organic molecule, results in a sharp increase in intracellular calcium similar to that produced by the exposure of the CaSR to increases in extracellular calcium (FIG. 22). These data demonstrate that certain milk proteins and their hydrolysis products, as well as specific peptides from other proteins, can activate CaSR proteins present on the mucosal surface of the gastrointestinal tract of nursing neonatal animals.

Example 7

Figure 26A:
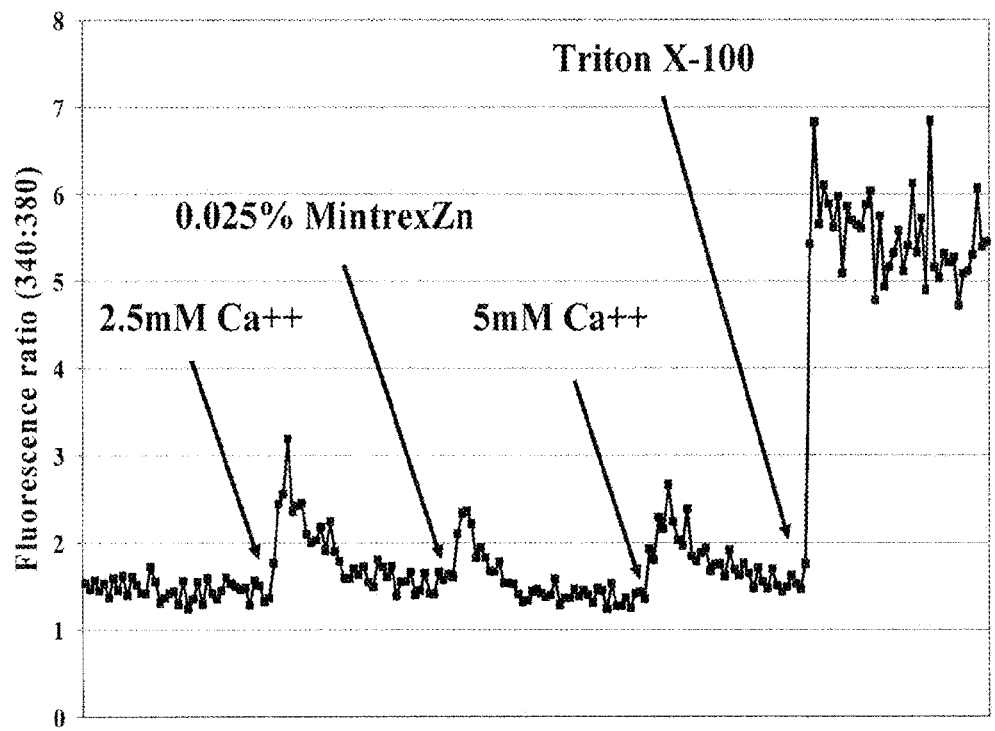
FIGS. 26A-D are graphs showing that the CaSR agonists, MC0100 (a calcimimetic) or 2.5 mM Ca2+, potentiate the response of the mammalian CaSR to the chelated mineral—Mintrex Zn. All tracings shown in FIGS. 26A-D were obtained from a single aliquot of CaSR transfected cells analyzed on the same day.
Figure 26B:
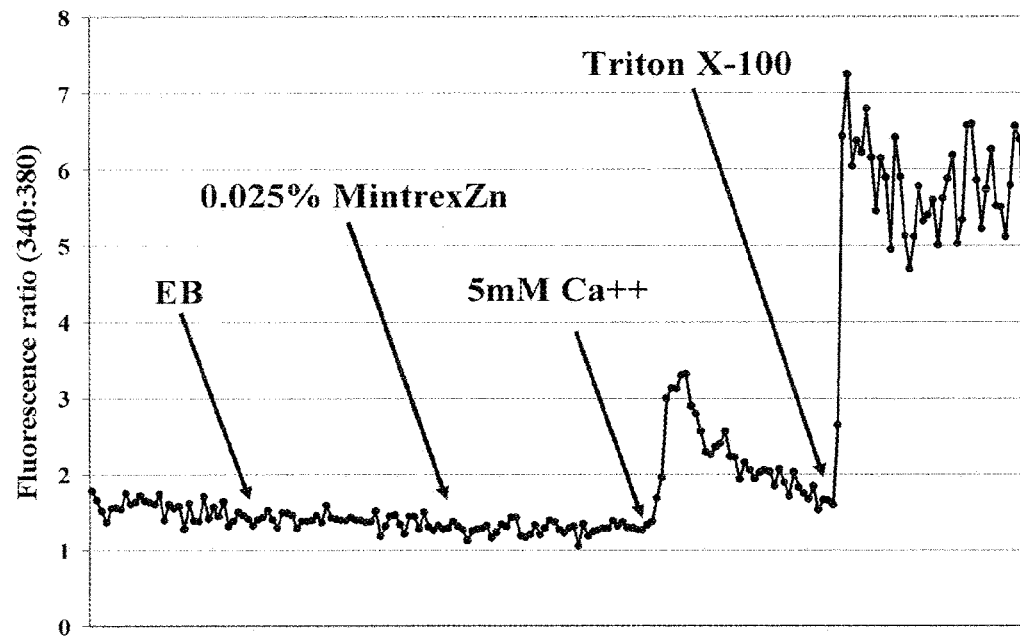
Figure 26C:
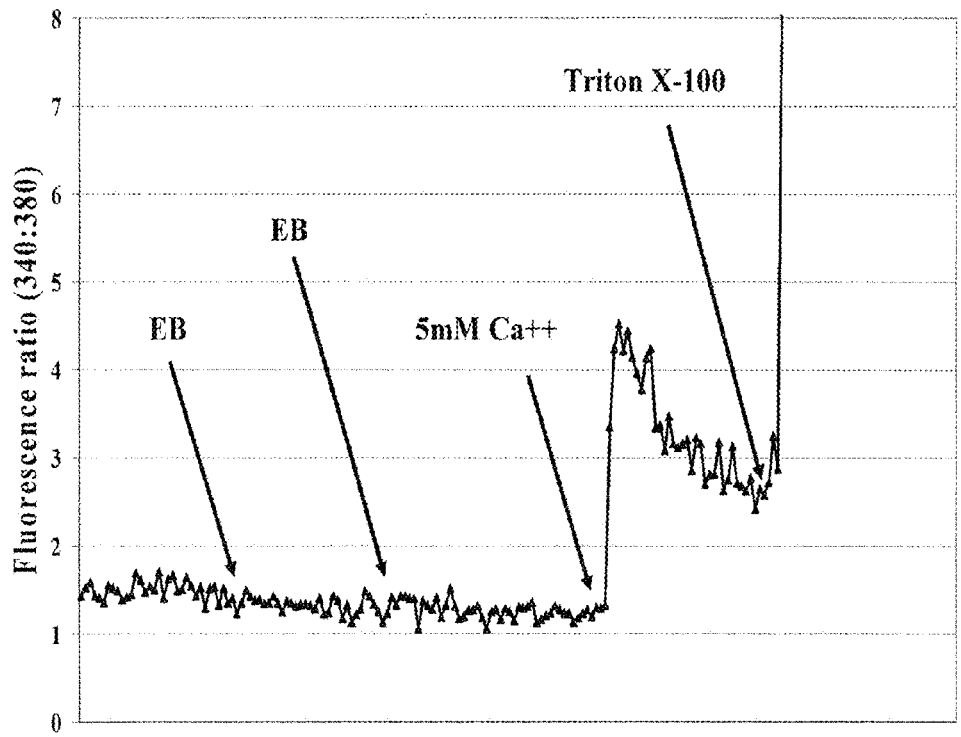
Figure 26D:
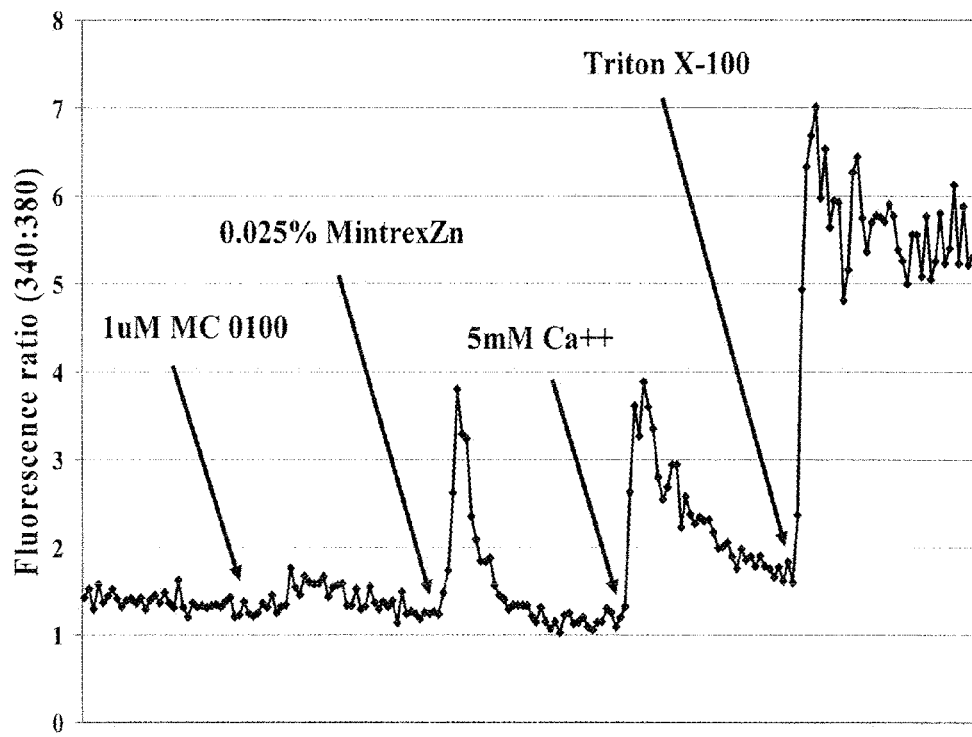

CaSR Modulators Effect the Response of Mammalian and Avian CaSRs to MINTREX® ZN, an Organic Acid Chelated Mineral Experiments on HEK cells were performed generally as described in Example 6 herein. After an initial addition of 2.5 mM Ca2+ the mammalian CaSR showed a response to the addition of 0.025% Mintrex Zn. Subsequent addition of Ca2+ to a final concentration of 5 mM produced an additional response (see FIG. 26A). No response was observed upon addition of 0.025% Mintrex Zn after the addition of experimental buffer (EB) (see FIG. 26B). Addition of the CaSR modulator, MC0100, to a final concentration of 1 micromolar produced a very small CaSR response and subsequent addition of 0.025% Mintrex Zn elicited a response as did a subsequent addition of Ca2+ to a final concentration of 5 mM. The CaSR responded to 0.025% Mintrex Zn only after the addition of 1 micromolar MC0100 (see FIG. 26D), as no response to Mintrex Zn stimulation was observed in the absence of previous addition of MC0100 (FIG. 26B). In addition, the magnitude of the CaSR response to 5 mM Ca2+ was diminished by previous addition of Mintrex Zn. This reduction in response is partially restored by previous addition of MC0100 (FIG. 26D).

Figure 27:
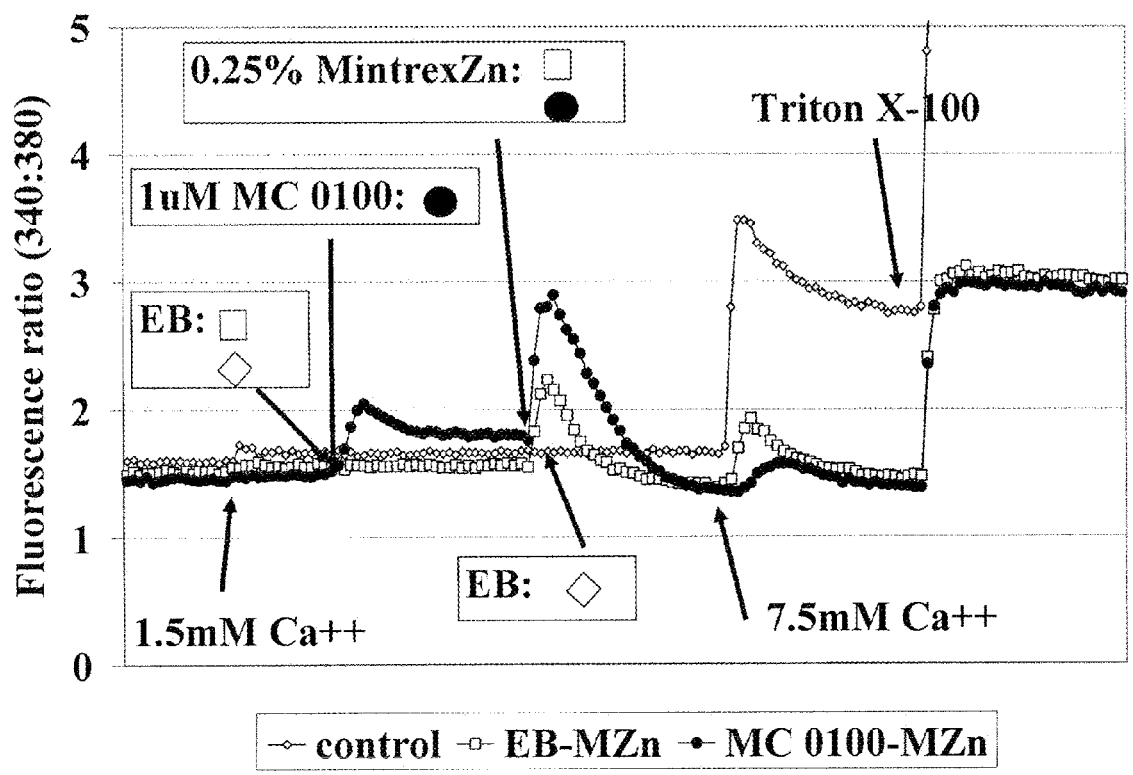
FIG. 27 is a graph showing that the CaSR agonist MC0100 (a calcimimetic) potentiates the response of the avian CaSR to the chelated mineral Mintrex Zn. As shown in the Control tracing indicated by the open diamonds, 2 additions of experimental buffer (EB) to cells suspended in buffer containing 1.5 mM Ca2+ do not produce a response by the avian CaSR. However, after addition of 7.5 mM Ca2+ to the same cell suspension, there is a response by the avian CaSR as indicated by the large upward deflection of the curve. By contrast, as indicated by the open squares, after an identical addition of EB, addition of 0.25% Mintrex Zn produces a response from the CaSR followed by a diminished response to the addition of Ca2+ to a final concentration of 7.5 mM. A third experimental run from the same collection of cells denoted by solid circles yielded a response upon addition of MC0100 to a final concentration of 1 micromolar followed by a significantly larger response of the avian CaSR upon addition of 0.25% Mintrex Zn. However, the subsequent CaSR response to Ca2+ addition to 7.5 mM was reduced. All 3 tracings are derived from a single pool of cells.

Similar results were obtained for the avian CaSR. The CaSR modulator MC0100 (calcimimetic) potentiated the response of the avian CaSR to the chelated mineral Mintrex Zn. Two additions of experimental buffer (EB) to cells suspended in buffer containing 1.5 mM Ca2+ did not produce a response by the avian CaSR. However, after addition of 7.5 mM Ca2+ to the same cell suspension, there was a response by the avian CaSR as indicated by the large upward deflection of the curve (FIG. 27). By contrast, after an identical addition of EB, addition of 0.25% Mintrex Zn produced a response from the CaSR followed by a diminished response to the addition of Ca2+ to a final concentration of 7.5 mM. A third experimental run from the same collection of cells yielded a response upon addition of MC0100 to a final concentration of 1 micromolar followed by a significantly larger response of the avian CaSR upon addition of 0.25% Mintrex Zn. However, the subsequent CaSR response to Ca2+ addition to 7.5 mM was reduced. All 3 tracings are derived from a single pool of cells.

Figure 28A:
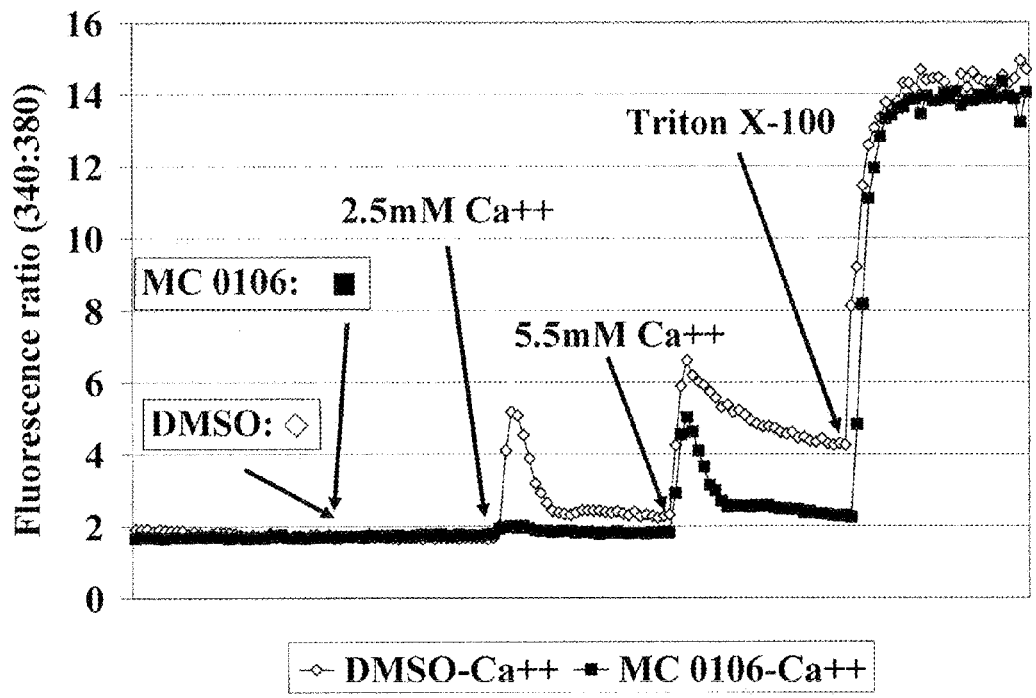
FIGS. 28A and B are graphs showing that the CaSR antagonist, MC106 (a calcilytic) reduces or eliminates the CaSR response to either Ca2+ or the chelated mineral, Mintrex Zn.

The CaSR antagonist, MC106, a calcilytic, reduced or eliminated the CaSR response to either Ca2+ or the chelated mineral, Mintrex Zn. After an initial addition of dimethylsulfoxide (DMSO) addition of Ca2+ to a final concentration of 2.5 mM elicited a response by the CaSR that is also present upon subsequent addition of Ca2+ to a final concentration of 5 mM (FIG. 28A). By contrast, addition of 1 micromolar MC106 suspended in the same concentration of DMSO did not itself produce a CaSR response but eliminated the CaSR response to 2.5 mM Ca2+ and reduced the subsequent response to 5 mM Ca2+ (FIG. 28A).

Figure 28B:
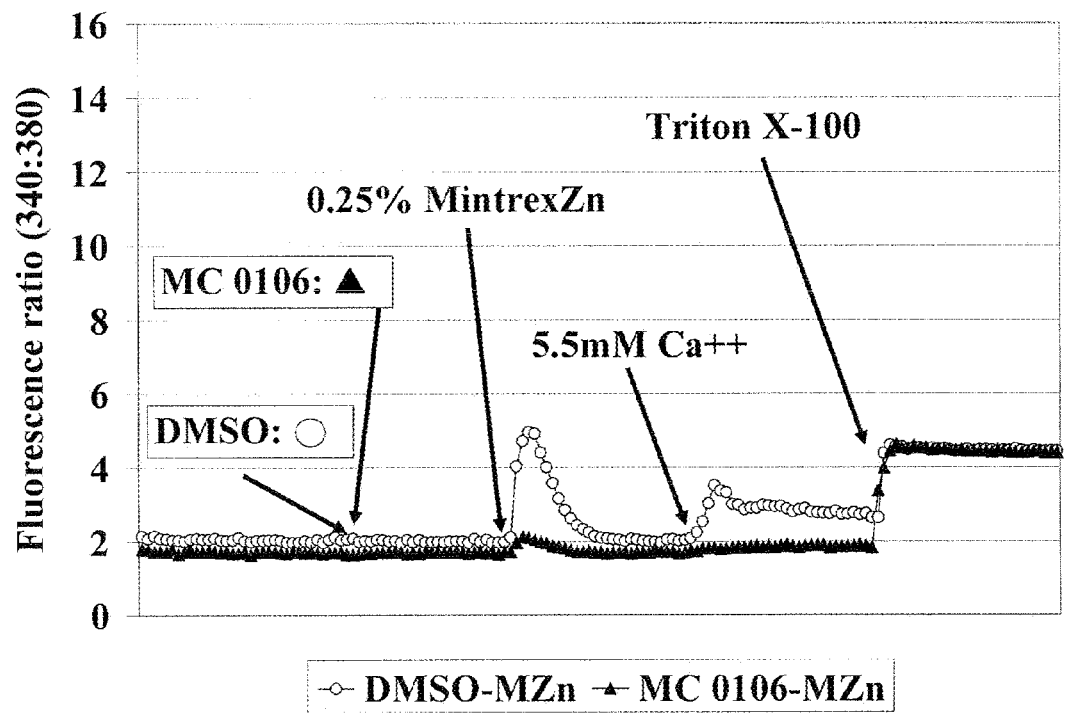
FIG. 28B: The tracing indicated by open circles shows that addition of DMSO elicits no CaSR response itself while subsequent addition of 0.25% Mintrex Zn and 5.5 mM Ca2+ produce responses by the mammalian CaSR. By contrast, as shown by the solid triangles, initial addition of 1 micromolar MC 106 in the same concentration of DMSO as before does not elicit a CaSR response but also reduces or eliminates responses by the CaSR to either 0.25% Mintrex ZN or 5.5 mM Ca2+. The final addition of the detergent Triton X-100 serves as an internal control in that it lyses the HEK cells and liberates all FURA2 dye for calibration purposes.

The addition of DMSO elicited no CaSR response itself while subsequent addition of 0.25% Mintrex Zn and 5.5 mM Ca2+ produced responses by the mammalian CaSR. By contrast, initial addition of 1 micromolar MC106 in the same concentration of DMSO as before did not elicit a CaSR response but also reduced or eliminated responses by the CaSR to either 0.25% Mintrex ZN or 5.5 mM Ca2+ (FIG. 28B). The final addition of the detergent Triton X-100 served as an internal control in that it lyses the HEK cells and liberates all FURA2 dye for calibration purposes.

Example 8

Figure 29A:
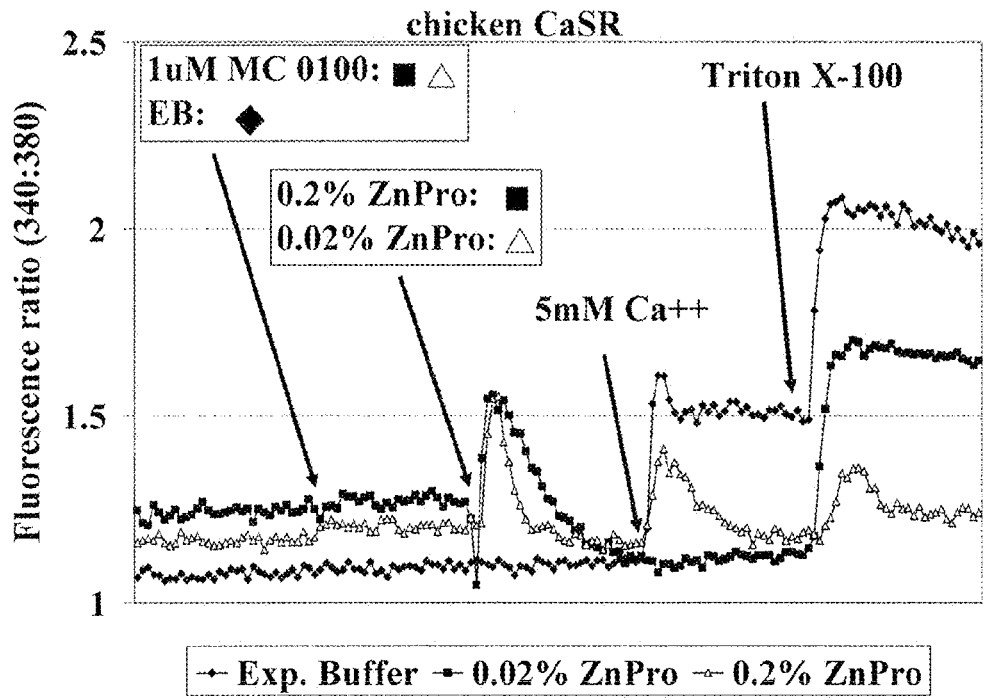
FIG. 29A is a graph showing that the CaSR modulator MC0100 potentiates the response of the avian CaSR to the chelated mineral amino acid complex, ZnPro. As shown in the Control tracing (solid diamonds), 2 additions of experimental buffer (EB) to cells suspended in buffer containing 0.5 mM Ca2+ do not produce a response by the avian CaSR. By contrast, after addition of the CaSR modulator, MC0100 (solid squares or open triangles) followed by addition of either 0.02% ZinPro (open triangles) or 0.2% ZnPro (solid squares) produced responses from avian CaSRs (indicated by upward deflections). Subsequent addition of Ca++ to a final concentration of 5 mM also produced a response. In all aliquots, the detergent Triton X-100 was added as the last addition to lyse the cells.

CaSR Modulators Effect the Response of Mammalian and Avian CaSRs to ZnPro, an Amino Acid Chelated Mineral The ability of the CaSR modulator MC0100 to potentiate the response of avian and mammalian CaSRs to the chelated mineral amino acid complex, ZnPro, was tested. For avian CaSR experiments, three individual aliquots from a single pool of HEK cells that stably express the recombinant avian CaSR protein were used for ratio imaging fluorimetry assays of CaSR activation generally as described in Example 6 herein. Two additions of experimental buffer (EB) to cells suspended in buffer containing 0.5 mM Ca2+ did not produce a response by the avian CaSR (FIG. 29A). By contrast, after addition of the CaSR modulator, MC0100 followed by addition of either 0.02% ZinPro or 0.2% ZnPro produced responses from avian CaSRs. Subsequent addition of Ca++ to a final concentration of 5 mM also produced a response. In all aliquots, the detergent Triton X-100 was added as the last addition to lyse the cells (FIG. 29A).

Figure 29B:
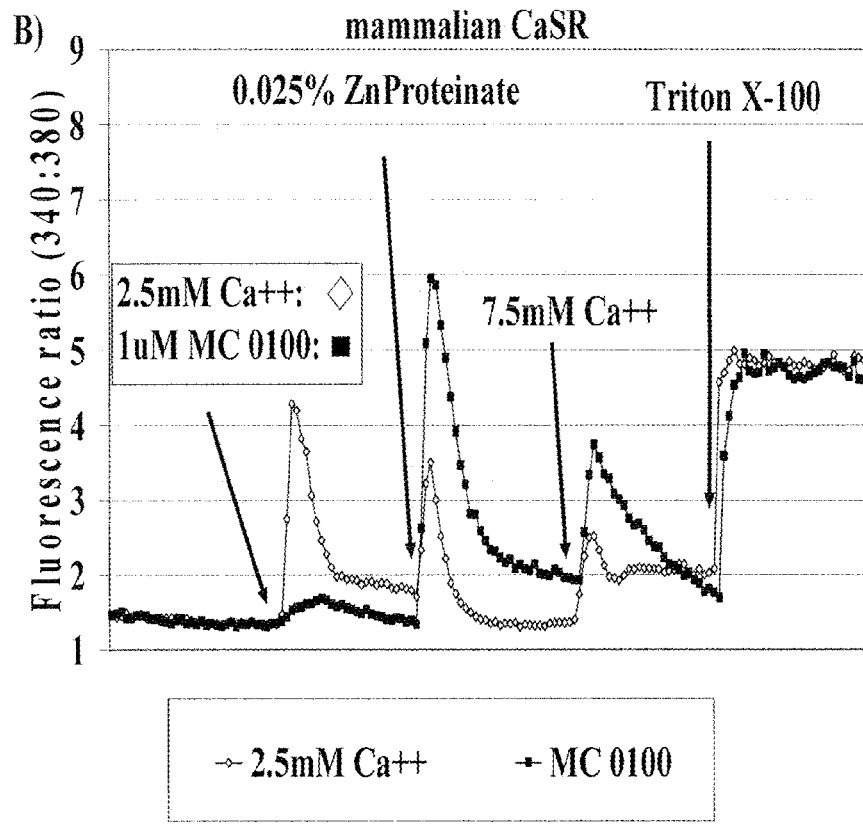
FIG. 29B is a graph showing that the CaSR modulator MC0100 potentiates the response of the mammalian CaSR to a zinc proteinate. Two individual aliquots from a single pool of HEK cells that stably express the recombinant mammalian CaSR protein were used for ratio imaging fluorimetry assays of CaSR activation as described previously. As shown in the tracing indicated by open diamonds, addition of Ca++ to a final concentration of 2.5 mM produced a CaSR response (upward deflection) that was also followed by responses after subsequent additions of 0.025% Zn proteinate followed by Ca++ to a final concentration of 7.5 mM. By contrast, addition of 1 micromolar MC0100, a CaSR modulator (shown in tracing with solid squares) did not itself produce a large response but instead increased the response of the CaSR to the same dose of 0.025% Zn Proteinate. There was also a response to a subsequent dose of Ca++ to a final concentration of 7.5 mM. In both tracings, the detergent Triton X-100 was added as a final step to lyse the cells.

For mammalian CaSR experiments, two individual aliquots from a single pool of HEK cells that stably express the recombinant mammalian CaSR protein were used for ratio imaging fluorimetry assays of CaSR activation generally as described in Example 6 herein. Addition of Ca++ to a final concentration of 2.5 mM produced a CaSR response that was also followed by responses after subsequent additions of 0.025% Zn proteinate followed by Ca++ to a final concentration of 7.5 mM (FIG. 29B). By contrast, addition of 1 micromolar MC0100, a CaSR agonist, did not itself produce a large response but instead increased the response of the CaSR to the same dose of 0.025% Zn Proteinate. There was also a response to a subsequent dose of Ca++ to a final concentration of 7.5 mM (FIG. 29B). In both tracings, the detergent Triton X-100 was added as a final step to lyse the cells.

Example 9

Figure 30A:
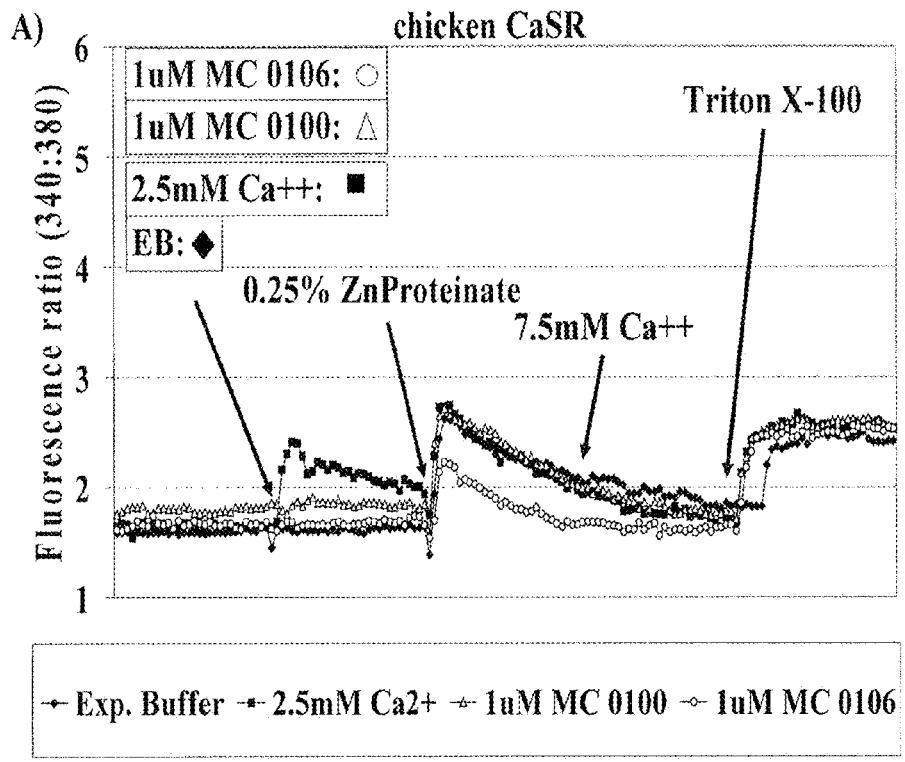
FIGS. 30A-D are graphs depicting a comparison of the effects of the CaSR modulators MC0100 and MC106 on avian vs. mammalian CaSRs stimulated by either zinc proteinate or the zinc organic acid complex, Mintrex Zn. Multiple aliquots of HEK cells stably expressing either the avian CaSR (FIGS. 30A and C) or mammalian CaSR (FIGS. 30B and D) were used to perform ratio imaging fluorimetry to determine the effects of CaSR modulators MC0100 or MC 106 on CaSR stimulation by chelated minerals.
Figure 30B:
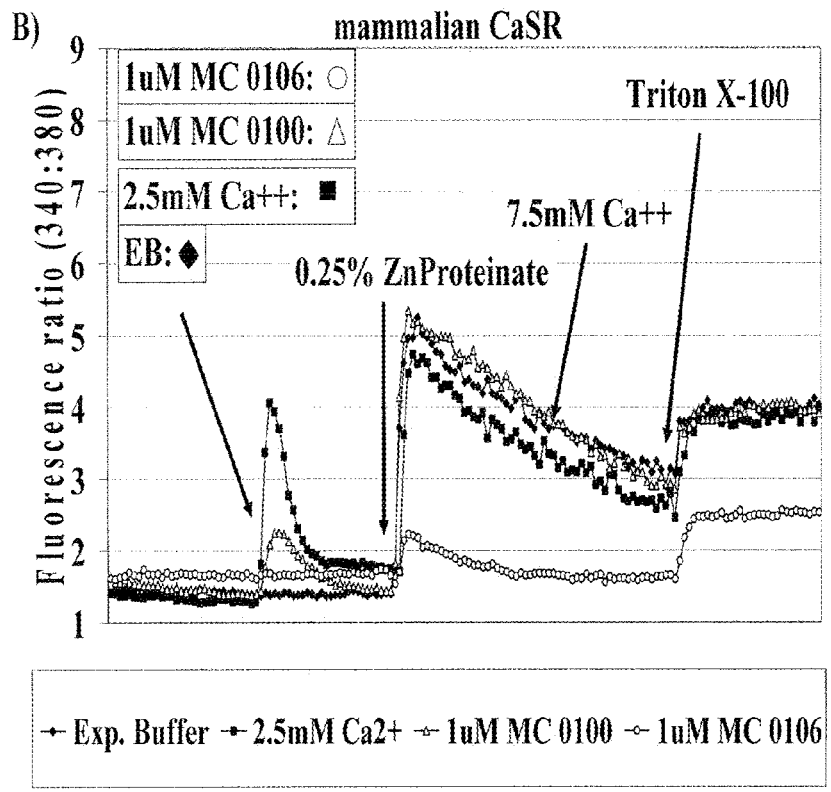
Figure 30C:
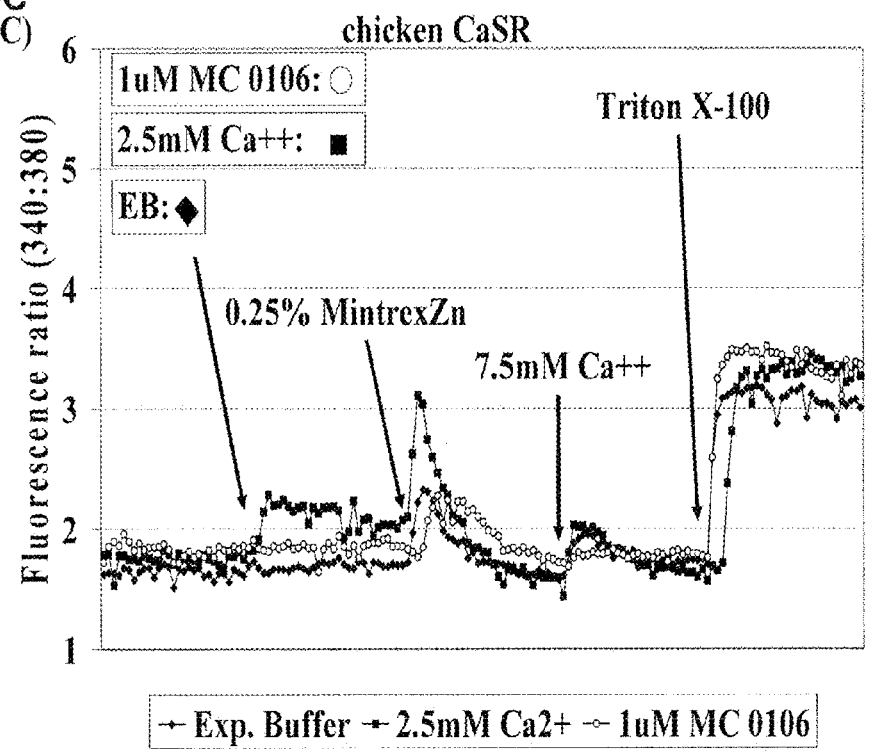
Figure 30D:
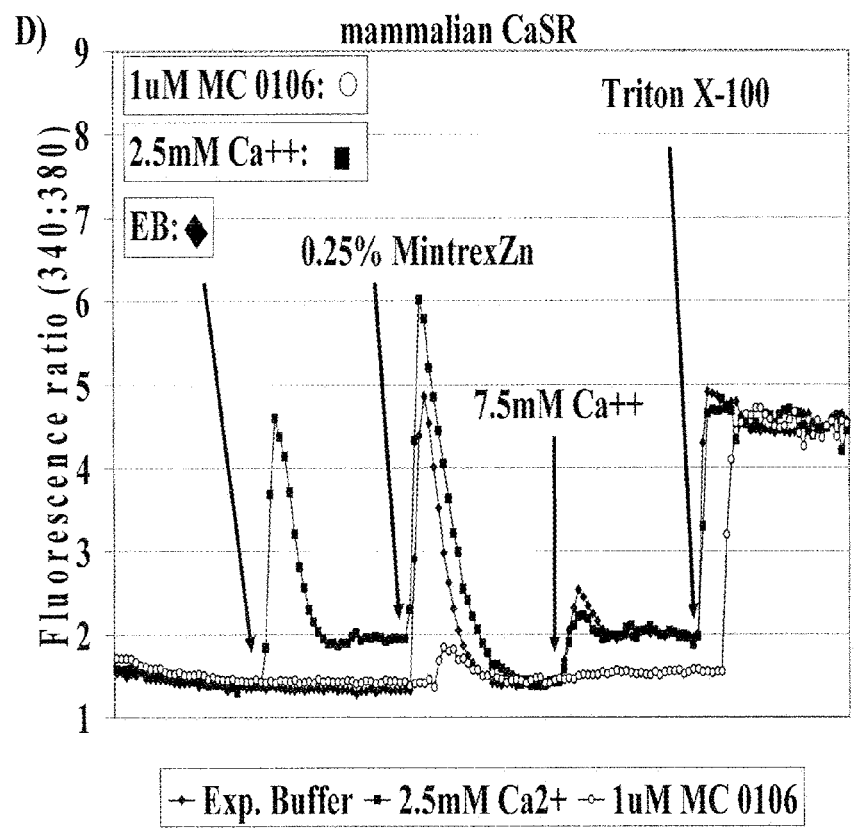

CaSR Modulators Effect the Response of Mammalian and Avian CaSRs to Zinc Proteinate Experiments on HEK cells were performed generally as described in Example 6 herein. The effects of the CaSR Modulators MC0100 and MC106 were compared on avian vs. mammalian CaSRs stimulated by either zinc proteinate or the zinc organic acid complex, Mintrex Zn. Multiple aliquots of HEK cells stably expressing either the avian CaSR (FIGS. 30A and C) or mammalian CaSR (FIGS. 30B and D) were used to perform ratio imaging fluorimetry to determine the effects of CaSR modulators MC0100 or MC106 on CaSR stimulation by chelated minerals. Prior addition of Ca++ to a final concentration of 2.5 mM or 1 micromolar produced a similar response of the avian CaSR as did experimental buffer (EB) alone when 0.25% Zinc Proteinate was then added to the cells (FIG. 30A). Subsequent addition of additional Ca++ to a final concentration of 7.5 mM to any of the 3 aliquots (EB alone; MC0100 or 2.5 mM Ca++) produced little or no CaSR response. By contrast, prior addition of 1 micromolar MC106 reduced the avian CaSR's response to Zn Proteinate (FIG. 30A). A similar analysis of the effects of prior addition of Ca++, MC0100 or MC106 on the response of the mammalian CaSR to Zinc Proteinate was performed. A similar pattern of inhibition by MC106 on the CaSR response to Zinc Proteinate was observed (FIG. 30B). Similar results were obtained for the avian and mammalian CaSRs using the zinc organic acid chelate, Mintrex Zn (FIGS. 30C, D).

Example 10

Figure 31A:
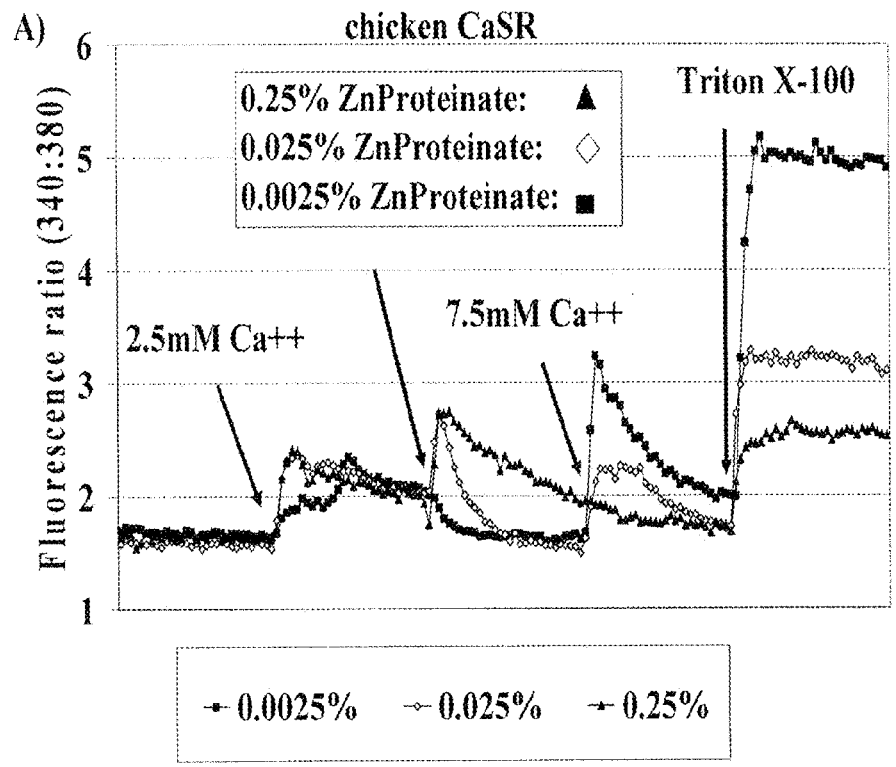
FIGS. 31A-D are graphs showing that the divalent metal ion-proteinate complex termed Zn Proteinate, activates both the avian and mammalian CaSRs in a manner similar to that produced by the divalent metal ion organic acid complex termed Mintrex Zn in a dose response relationship.
Figure 31B:
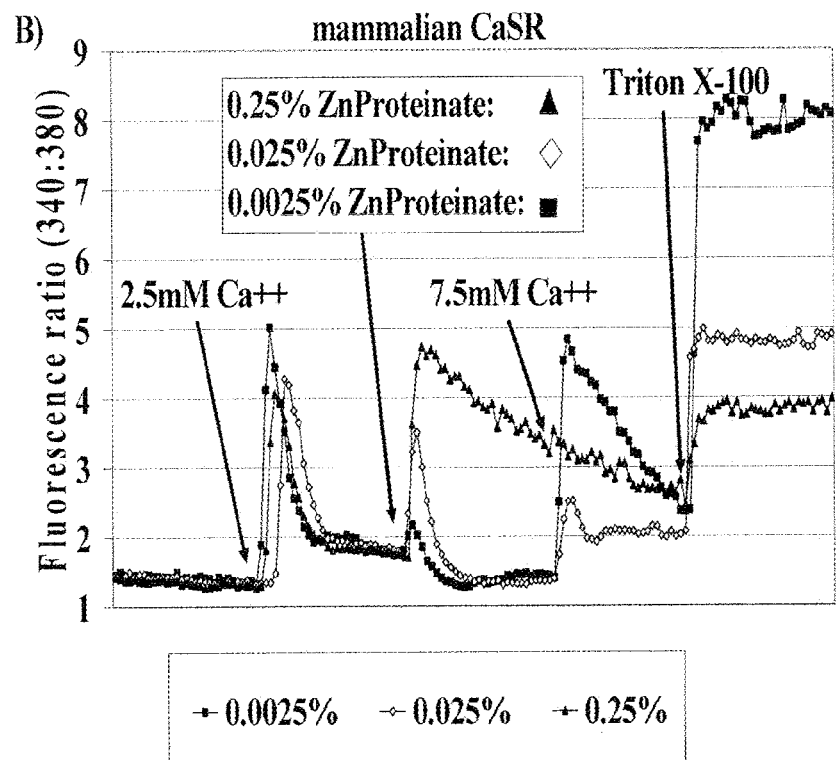
Figure 31C:
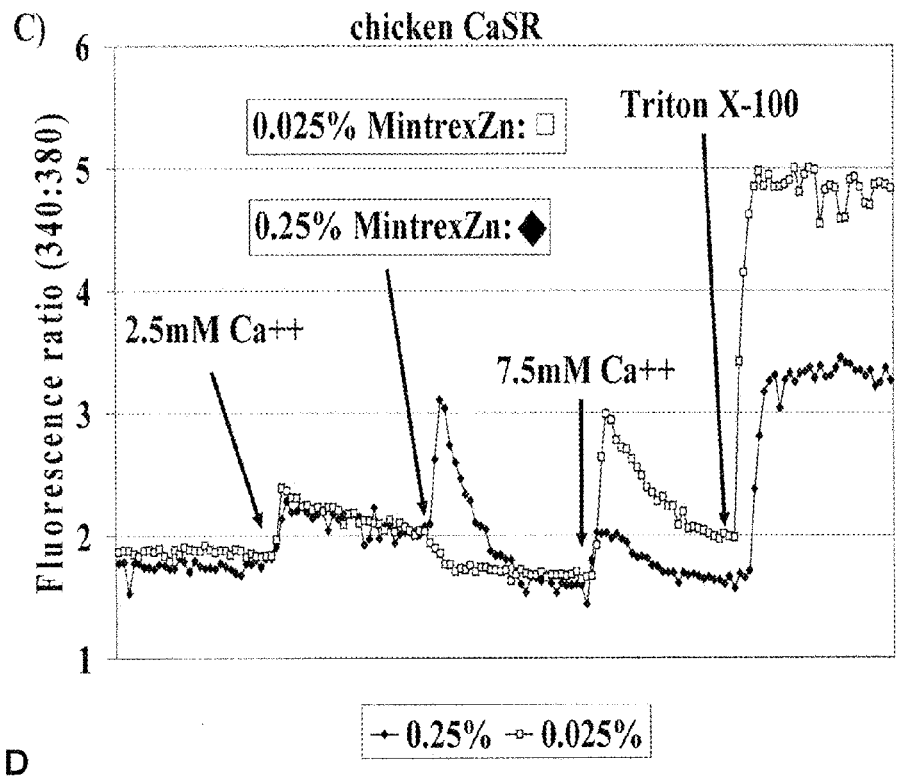
Figure 31D:
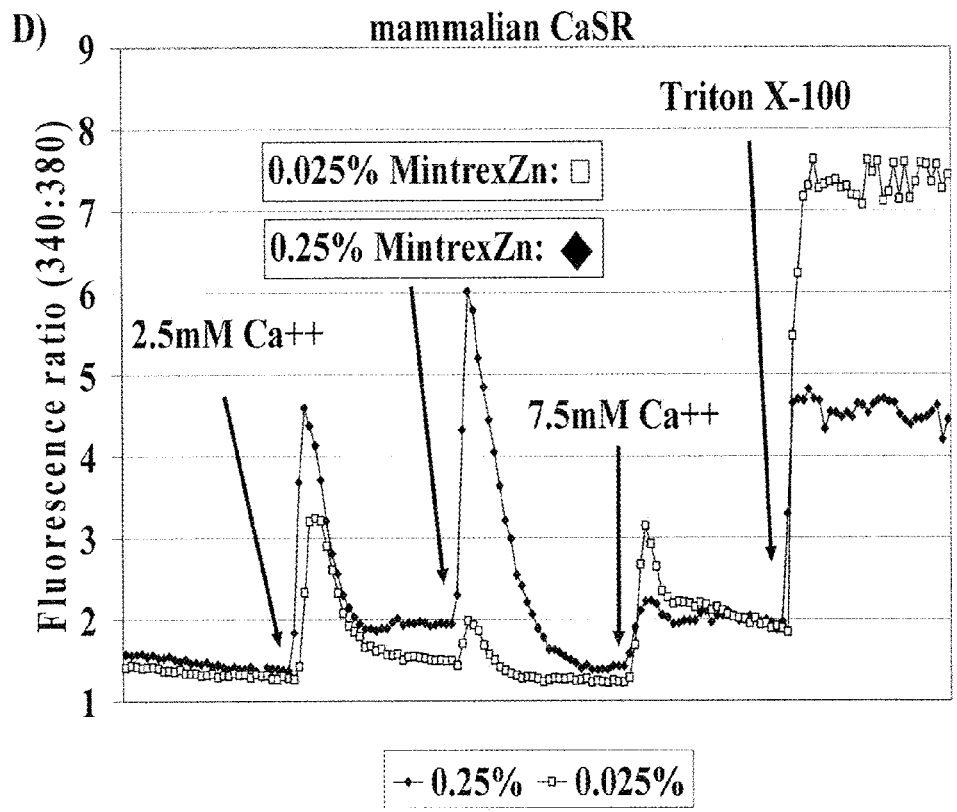

Zn Proteinate, a Divalent Metal Ion-Proteinate Complex, Activates Both the Avian and Mammalian CaSRs in a Dose Response Relationship in a Manner Similar to Mintrex Zn From a single pool of HEK cells stably expressing the avian CaSR, aliquots of cells were removed and analyzed using ratio imaging fluorimetry generally as described in Example 6 herein. After a standard addition of Ca++ to a final concentration of 2.5 mM, either 0.0025%, 0.025% or 0.25% Zinc Proteinate was added followed by a second addition of Ca++ to a final concentration of 7.5 mM. Subsequently, an aliquot of the detergent Triton X-100 was added to lyse the cells. 0.0025% elicited little or no CaSR response while 0.025% and 0.25% produced increasing responses from the avian CaSR (FIG. 31A). The magnitude of the subsequent CaSR response to Ca++ was reduced via increasing Zn Proteinate stimulation. The mammalian CaSR also displayed a similar dose response pattern as the avian CaSR (FIG. 31B). Similar results were obtained for the avian and mammalian CaSRs using the zinc organic acid chelate, Mintrex Zn (FIGS. 31C, D).

Example 11

Figure 32:
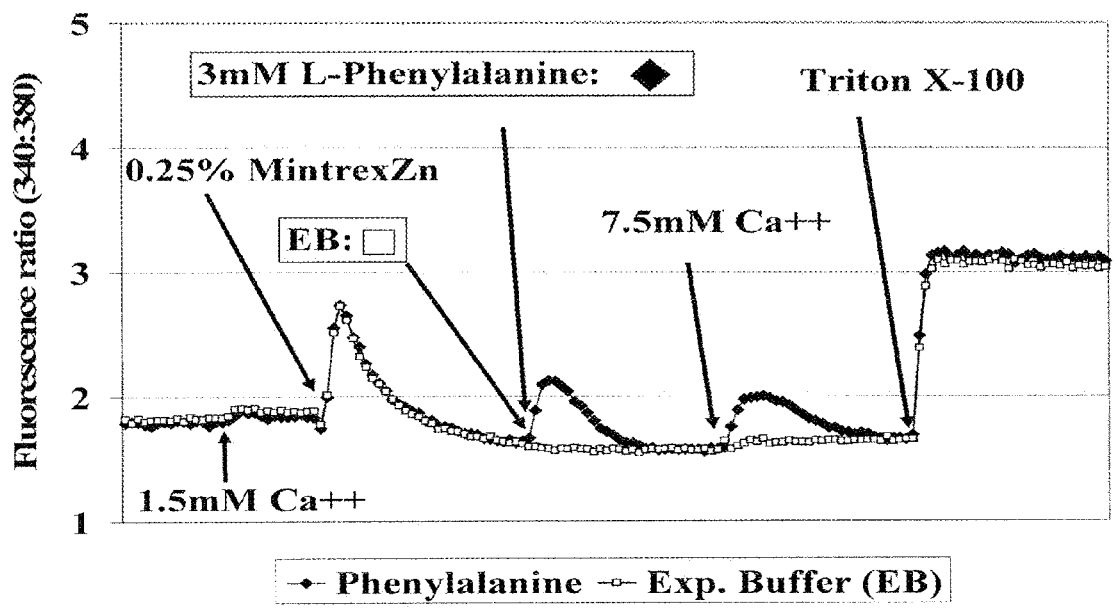
FIG. 32 is a graph showing that the addition of 3 mM L-Phenylalanine (L-Phe) reverses Mintrex-Zn's inhibition of the avian CaSR's response to a Ca++ stimulus. As shown by the open squares, prior addition of 0.25% Mintrex Zn to the recombinant chicken CaSR expressed in HEK cells produces an initial receptor response (indicated by upward deflection) but then no CaSR response is obtained after the addition of Ca++ to a final concentration of 7.5 mM. The detergent Triton X-100 was added last to lyse the cells. By contrast, identical fluorimetry analysis of a separate aliquot from the same pool of cells as shown by the solid diamonds, shows that addition of 3 mM L-Phe after CaSR stimulation with 0.25% Mintrex Zn now produces a response to addition of Ca++ to 7.5 mM. Thus, prior addition of L-Phe reverses or rescues the avian CaSR from its inhibition by the chelated mineral Mintrex Zn.

The CaSR Modulator L-Phenylalanine (L-Phe) Reverses the Inhibitory Effect of Chelated Minerals on Response to a Ca++ Stimulus in Mammalian and Avian CaSRs Experiments on HEK cells were performed generally as described in Example 6 herein. Addition of 3 mM L-Phenylalanine (L-Phe) reversed Mintrex-Zn's inhibition of the avian CaSR's response to a Ca++ stimulus. Prior addition of 0.25% Mintrex Zn to the recombinant chicken CaSR expressed in HEK cells produced an initial receptor response, but no subsequent CaSR response was obtained after the addition of Ca++ to a final concentration of 7.5 mM (FIG. 32). The detergent Triton X-100 was added last to lyse the cells. By contrast, identical fluorimetry analysis of a separate aliquot from the same pool of cells revealed that addition of 3 mM L-Phe after CaSR stimulation with 0.25% Mintrex Zn produced a response to addition of Ca++ to 7.5 mM (FIG. 32). Thus, prior addition of L-Phe reversed or rescued the avian CaSR from its inhibition by the chelated mineral Mintrex Zn.

Figure 33:
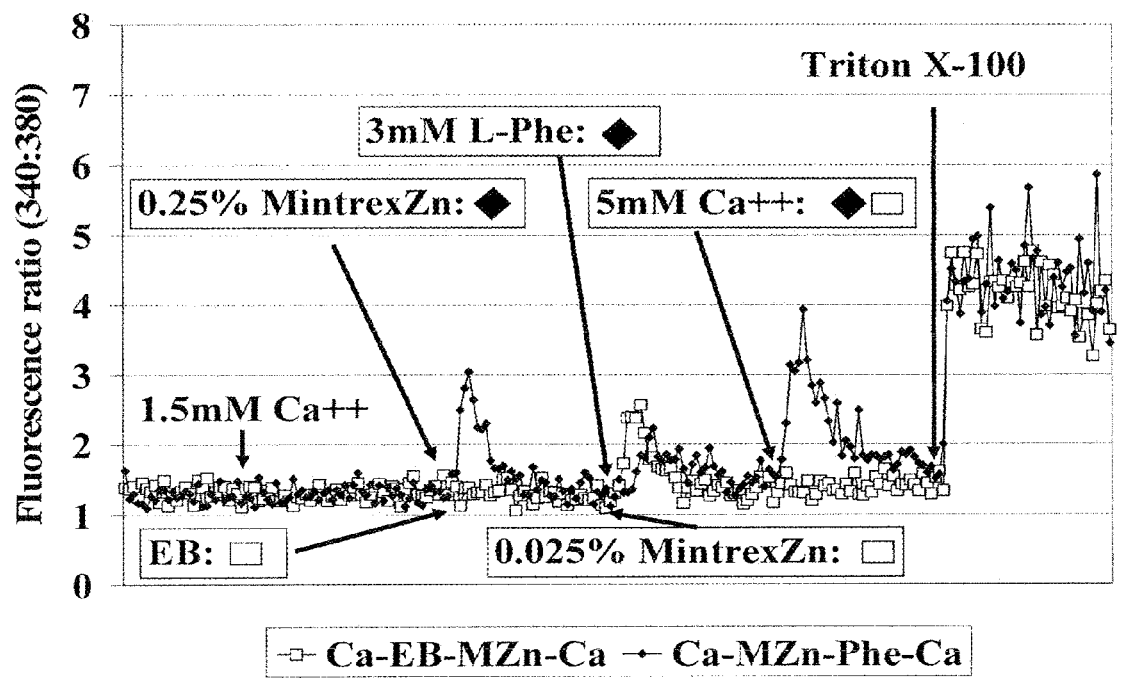
FIG. 33 is a graph showing that the addition of 3 mM L-Phenylalanine (L-Phe) reverses Mintrex-Zn's inhibition of the mammalian CaSR's response to a Ca++ stimulus at extracellular calcium concentrations that correspond to mammalian serum (1.5 mM Ca++). As shown by the open squares, addition of experimental buffer alone (EB) produces no response by the recombinant mammalian CaSR expressed in HEK cells. However, addition of 0.025% Mintrex Zn produces an initial receptor response (indicated by upward deflection) but then no CaSR response is obtained after the addition of Ca++ to a final concentration of 5 mM. The detergent Triton X-100 was added last to lyse the cells. By contrast, identical fluorimetry analysis of a separate aliquot from the same pool of cells as shown by the solid diamonds, shows that addition of 3 mM L-Phe after CaSR stimulation with 0.025% Mintrex Zn now produces a response to addition of Ca++ to 5 mM. Thus, prior addition of L-Phe reverses or rescues the mammalian CaSR from its inhibition by the chelated mineral Mintrex Zn in a manner similar to that shown for the avian receptor in FIG. 32.

In a separate experiment, addition of 3 mM L-Phenylalanine (L-Phe) reversed Mintrex-Zn's inhibition of the mammalian CaSR's response to a Ca++ stimulus at extracellular calcium concentrations that correspond to mammalian serum (1.5 mM Ca++). Addition of experimental buffer alone (EB) produced no response by the recombinant mammalian CaSR expressed in HEK cells (FIG. 33). However, addition of 0.025% Mintrex Zn produced an initial receptor response, but no subsequent CaSR response was obtained after the addition of Ca++ to a final concentration of 5 mM. The detergent Triton X-100 was added last to lyse the cells. By contrast, identical fluorimetry analysis of a separate aliquot from the same pool of cells revealed that addition of 3 mM L-Phe after CaSR stimulation with 0.025% Mintrex Zn produced a response to addition of Ca++ to 5 mM (FIG. 33). Thus, in a manner similar to that shown for the avian receptor, prior addition of L-Phe reversed or rescued the mammalian CaSR from its inhibition by the chelated mineral Mintrex Zn.

Example 12

Mammalian and Avian CaSR Proteins are Able to Respond to Metal Proteinates Via Activation of Downstream Signaling Pathways Like CaSR Dependent ERK 1/2 Phosphorylation Materials and Methods HEK cells transfected with the chicken CaSR were cultured under standard conditions (DMEM with 10% FCS). Confluent flasks were serum-starved overnight in DMEM supplemented with 0.2% BSA and pre-incubated for 60 min at 37° C. in the following medium: 125 mM NaCl, 4 mM KCl, 20 mM Hepes, 0.1% glucose, 0.8 mM NaH2PO4, 1 mM $MgCl_2$, 0.1% BSA, 0.5 mM $CaCl_2$, pH 7.45. The cells were then incubated in the same medium without BSA in the presence of different mineral chelates at different concentrations (see below) for 15 min at 37° C. At the end of the incubation treatment media was removed and cells were washed with PBS and than lysed in 250 microliter of M-PER lysis buffer (Pierce Chemical Company, Rockford, Ill.) containing 10 ul/ml of protease inhibitors (Pierce Chemical Company, Rockford, Ill.). Cell lysates were centrifuged for 10 min at 4° C. at 14,000×g. The protein content in the supernatants was analyzed using the BCA Protein Assay system from Pierce Chemical Company, Rockford, Ill. Equal amounts of protein (20 ug) were combined with 4× loading buffer and 100 uM DTT, heated to 95° C., separated by SDS gel electrophoresis and electrotransferred to PVD membranes. The membranes were incubated in 1% BSA in TBS-T (TRIS-buffered saline containing Tween 20 at 0.1%) overnight. After 4 washes in TBS-T the membranes were incubated with primary antibody (anti phosphoERK at 1:400 dilution; this antibody recognizes the phosphorylated form of ERK 1/2) for 1.5 hours at room temperatures, washed 4 times and incubated with secondary antibody (anti mouse at 1:50,000 dilution). After 4 washes in TBS-T the membranes were developed using the ECL Western Blotting system.

The experiments described in FIGS. 34 A and B used the following metal chelate treatments: ZnProteinate, CuProteinate and MnProteinate (Balchem Corporation, New Hampton, N.Y.) at the following concentrations: 0.025% and 2.5%, or at a concentration of 0.025% with 1 micromolar MC 0100 (a calcimimetic); or various concentrations of bacitracin Zn.

Results

Figure 34A:
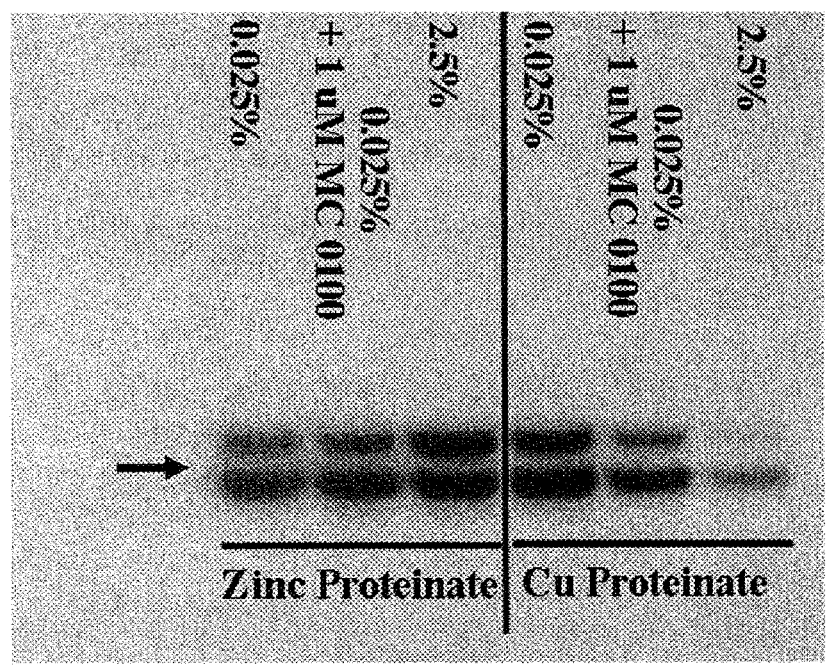
FIGS. 34A and B are Western blots showing that the avian CaSR protein is able to respond to metal chelates via activation of downstream signaling pathways like CaSR dependent ERK 1/2 phosphorylation. Arrows denote the bands corresponding to phosphorylated ERK1/2 protein. As shown, the Zn Proteinate and Mn Proteinate resulted in an increase in ERK1/2 phosphorylation with increasing concentration (FIG. 34A, left and right panels). By contrast, Cu Proteinate displayed the highest ERK1/2 phosphorylation after exposure of HEK cells to the lowest concentration of 0.025% (FIG. 34B). The calcimimetic MC 0100 strongly enhanced the ERK1/2 phosphorylation response to 0.025% Mn Proteinate and to a lesser degree to Zn Proteinate. Note that Zn Proteinate at 0.025% already showed a higher phosphorylation response when compared to the response to 0.025% Mn Proteinate. By contrast, the addition of MC 0100 in combination with 0.025% Cu Proteinate results in a net reduction of the ERK1/2 phosphorylation response when compared to other metal chelate complexes tested.
Figure 34B:
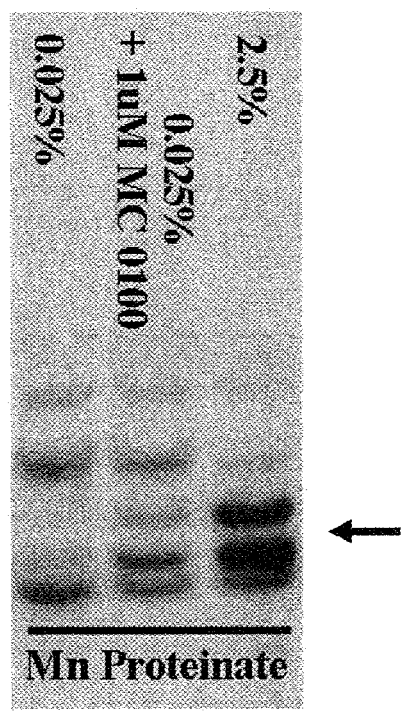

All 3 chelated mineral complexes displayed a dose dependent response. The Zn Proteinate (FIG. 34A) and Mn Proteinate (FIG. 34B) resulted in an increase in ERK1/2 phosphorylation with increasing concentration. By contrast, Cu Proteinate displayed the highest ERK1/2 phosphorylation after exposure of HEK cells to the lowest concentration of 0.025% (FIG. 34A). The calcimimetic MC 0100 strongly enhanced the ERK1/2 phosphorylation response to 0.025% Mn Proteinate and to a lesser degree to Zn Proteinate. Notably, Zn Proteinate at 0.025% already showed a higher phosphorylation response when compared to the response to 0.025% Mn Proteinate. By contrast, the addition of MC 0100 in combination with 0.025% Cu Proteinate results in a net reduction of the ERK1/2 phosphorylation response when compared to other metal chelate complexes tested.

Figure 35:
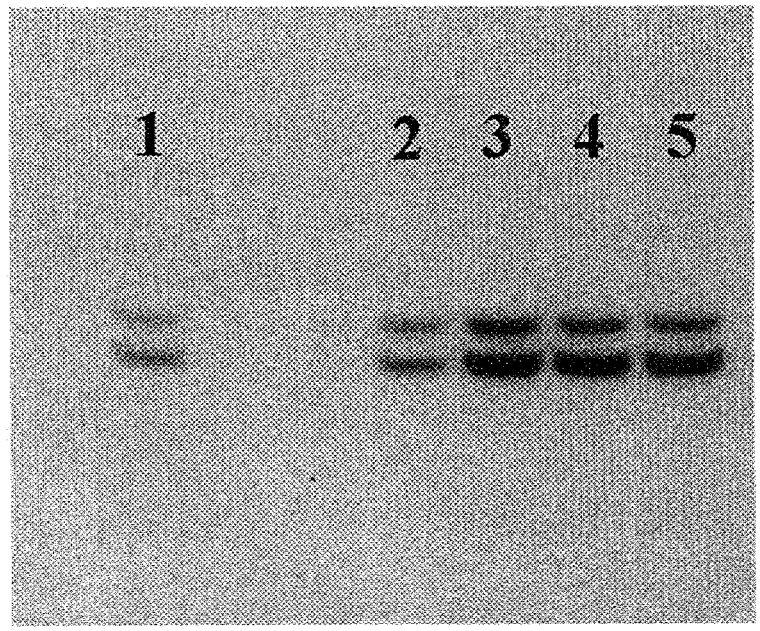
FIG. 35 is a Western blot showing that the avian CaSR protein is able to respond to the growth promoting antibiotic Bacitracin Zn via the activation of downstream signalling pathways like CaSR dependent ERK 1/2 phosphorylation. Arrows denote the bands corresponding to phosphorylated ERK1/2 protein. As shown, exposure of HEK cells stably expressing the chicken CaSR to bacitracin Zn resulted in an increase in ERK1/2 phosphorylation as compared to Ca++ with MC0100.

Exposure of HEK cells stably expressing the chicken CaSR to bacitracin Zn resulted in an increase in ERK1/2 phosphorylation as compared to Ca++ with MC0100 (FIG. 35).

Example 13

The Phenylalkylamine Compounds Fendiline and Prenylamine Stimulate Avian and Mammalian CaSRs in a Manner Similar to MC0100

Fluorimetry analysis was performed on HEK cells expressing the recombinant chicken CaSR protein generally as described in Example 6 herein.

Figure 36:
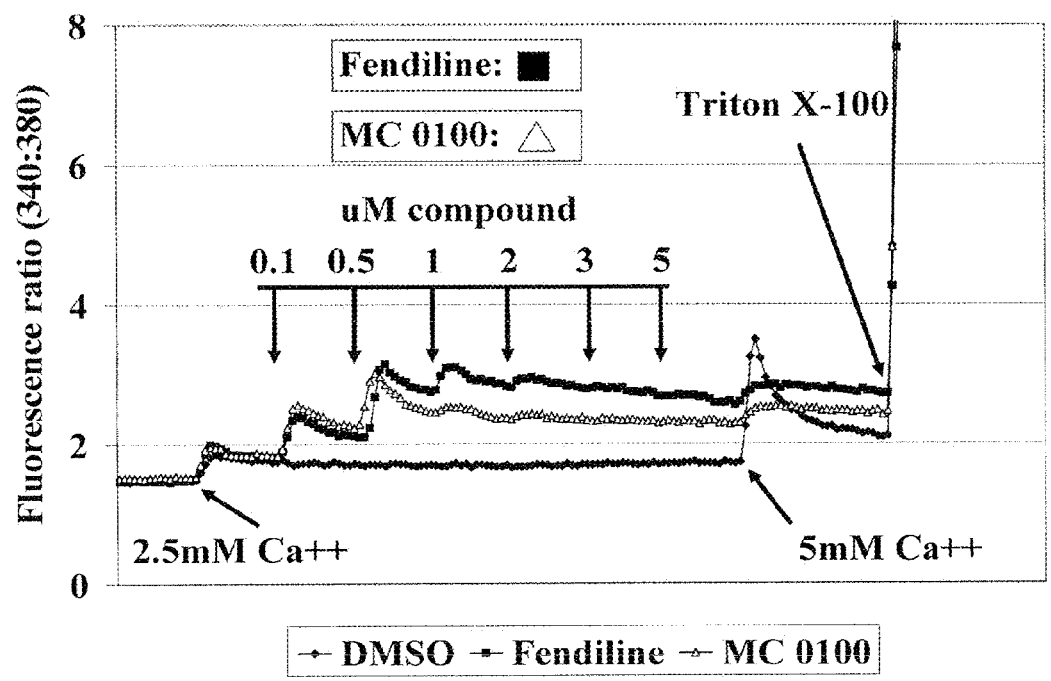
FIG. 36 is a graph showing that fendiline stimulates the avian CaSR similar to the responses observed for the CaSR agonist MC0100. Fluorimetry analysis was performed on HEK cells expressing the recombinant chicken CaSR protein. As shown by the open triangles symbols, after addition of 2.5 mM Ca++, a series of stepwise additions of the known CaSR modulator, MC0100, causes increased responses of the CaSR as indicated by the series of upward deflections and elevation of the baseline. In a similar manner, additions of fendiline (shown by the solid squares) to a second aliquot of the same CaSR-HEK cells produce similar responses in the avian CaSR. As a control, no such responses were observed when additions of the vehicle DMSO only was added as indicated by the solid diamonds followed by a single addition of Ca++ to a final concentration of 5 mM. The addition of the detergent Triton X-100 was added last to each cuvette to lyse the cells at the end of each analysis run.
Figure 37:
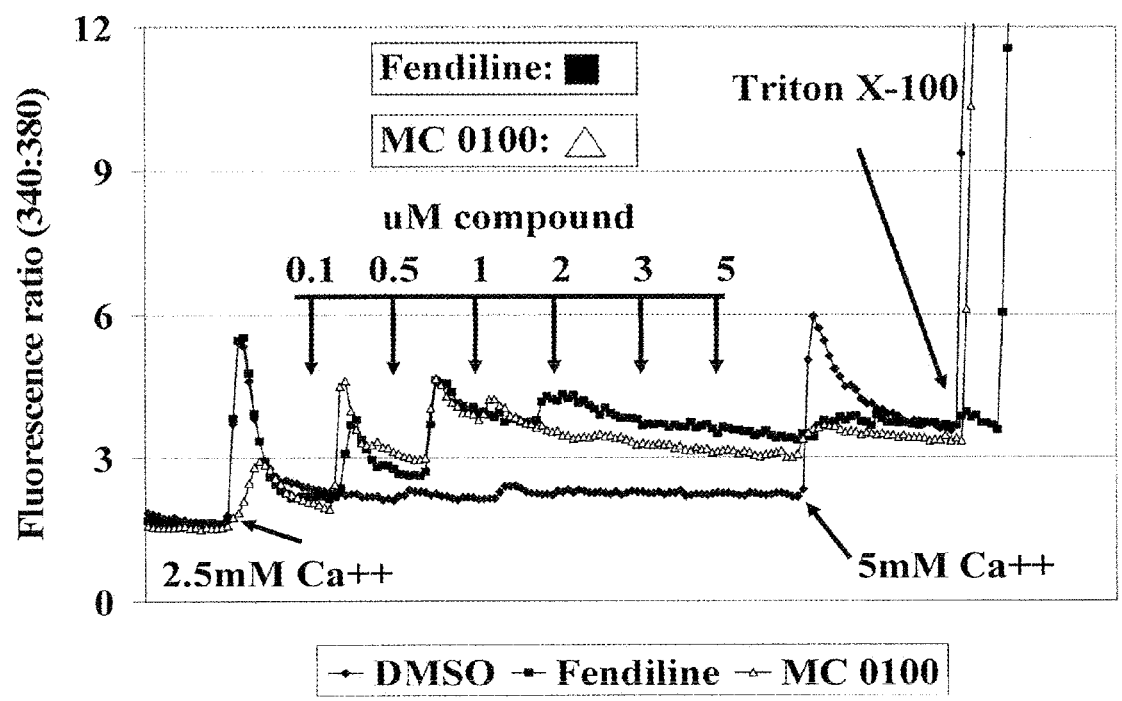
FIG. 37 is a graph showing that fendiline stimulates the mammalian CaSR similar to the responses observed for the CaSR agonist MC0100. Fluorimetry analysis was performed on HEK cells expressing the recombinant mammalian CaSR protein. As shown by the open diamond symbols, after addition of 2.5 mM Ca++, a series of stepwise additions of the known CaSR modulator, MC0100, causes increased responses of the CaSR as indicated by the series of upward deflections and elevation of the baseline. In a similar manner, additions of fendiline (shown by the solid squares) to a second aliquot of the same CaSR-HEK cells produce similar responses in the avian CaSR. As a control, no such responses were observed when additions of the vehicle DMSO only was added as indicated by the solid diamonds followed by a single addition of Ca++ to a final concentration of 5 mM. The addition of the detergent Triton X-100 was added last to each cuvette to lyse the cells at the end of each analysis run.

In a first experiment, after addition of 2.5 mM Ca++, a series of stepwise additions of the CaSR agonist, MC0100, caused increased responses of the mammalian CaSR (FIG. 36). In a similar manner, additions of fendiline to a second aliquot of the same CaSR-HEK cells produced similar responses in the avian CaSR (FIG. 37). As a control, no such responses were observed when additions of the vehicle DMSO only was added followed by a single addition of Ca++ to a final concentration of 5 mM. The addition of the detergent Triton X-100 was added last to each cuvette to lyse the cells at the end of each analysis run.

Figure 38:
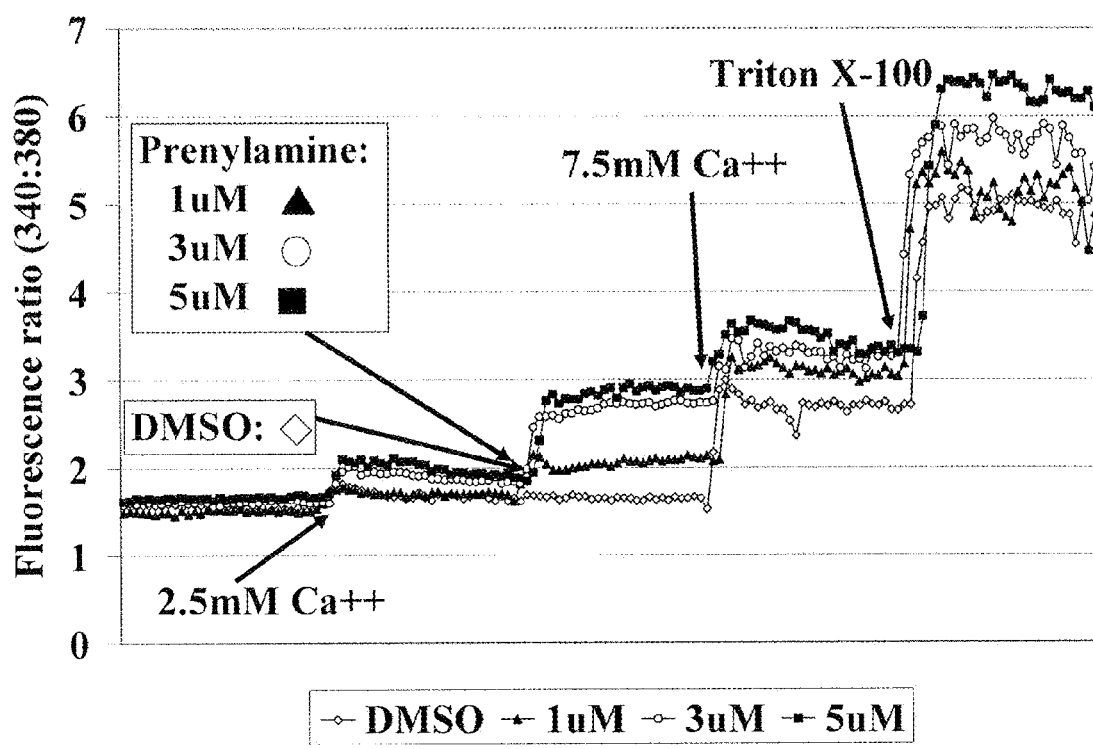
FIG. 38 is a graph showing that prenylamine stimulates the avian CaSR similar to the responses observed for other CaSR agonists. Fluorimetry analysis was performed on HEK cells expressing the recombinant chicken CaSR protein. Analysis was performed on 3 separate aliquots obtained from a single pool of CaSR-HEK cells using either 1 micromolar (solid triangles), 3 micromolar (open circles) or 5 micromolar (solid squares) prenylamine after addition of Ca++ to a final concentration of 2.5 mM. After the addition of prenylamine, each aliquot of cells received a subsequent addition of Ca++ to a final concentration of 7.5 mM. A CaSR response is shown as an upward deflection and elevation of the baseline. As a control, no such response was observed when addition of the vehicle DSMO (shown as the open diamonds) was added. The addition of the detergent Triton X-100 was added last to each cuvette to lyse the cells at the end of each analysis run.
Figure 39:
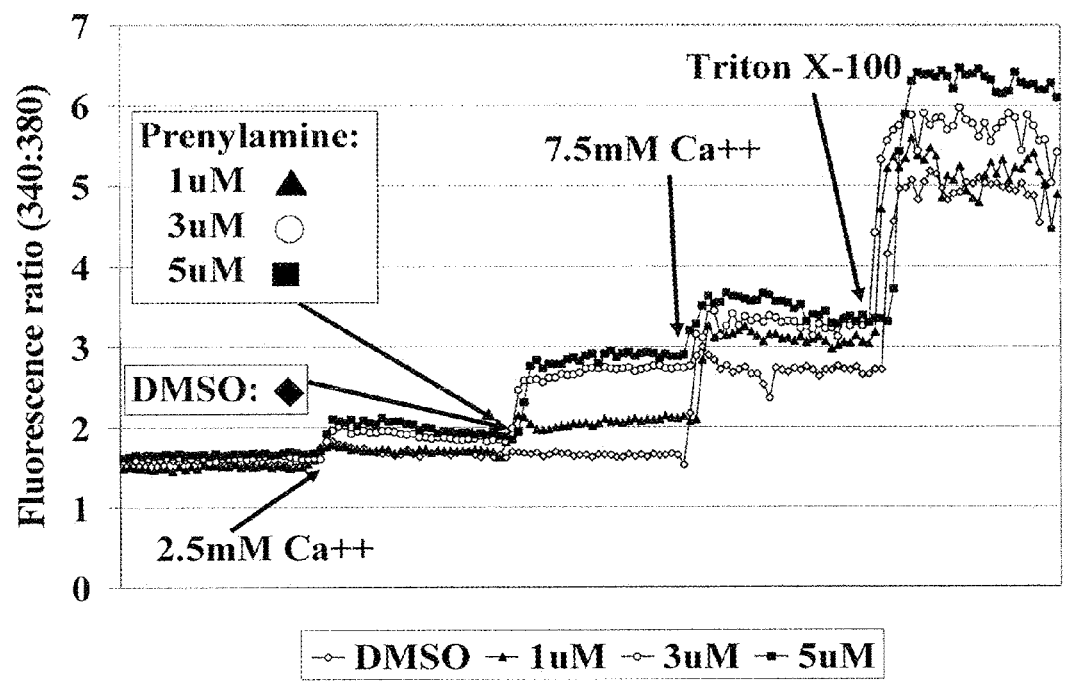
FIG. 39 is a graph showing that prenylamine stimulates the mammalian CaSR similar to the responses observed for other CaSR agonists. Fluorimetry analysis was performed on HEK cells expressing the recombinant mammalian CaSR protein. Analysis was performed on 3 separate aliquots obtained from a single pool of CaSR-HEK cells using either 1 micromolar (solid diamonds), 3 micromolar (open circles) or 5 micromolar (solid squares) prenylamine after addition of Ca++ to a final concentration of 2.5 mM. After the addition of prenylamine, each aliquot of cells received a subsequent addition of Ca++ to a final concentration of 7.5 mM. A CaSR response is shown as a upward deflection and elevation of the baseline. As a control, no such response were observed when addition of the vehicle DSMO (shown as the open circles) was added. The addition of the detergent Triton X-100 was added last to each cuvette to lyse the cells at the end of each analysis run.

In another experiment, 3 separate aliquots obtained from a single pool of CaSR-HEK cells were treated with either 1 micromolar, 3 micromolar or 5 micromolar prenylamine after addition of Ca++ to a final concentration of 2.5 mM. After the addition of prenylamine, each aliquot of cells received a subsequent addition of Ca++ to a final concentration of 7.5 mM. A CaSR response was observed for both the mammalian and avian CaSRs (FIGS. 38 and 39). As a control, no such response were observed when addition of the vehicle DSMO was added. The addition of the detergent Triton X-100 was added last to each cuvette to lyse the cells at the end of each analysis run.

Example 14

CaSR Proteins Localize to Stratum Corneum, and Epidermal and Dermal Tissues, in the Skin of Broiler Chicken Feet Materials and Methods Standard immunocytochemistry was performed on permeabilized fixed tissue sections of broiler chicken skin from the foot pad region of feet using either specific anti-CaSR antiserum or pre-immune anti-CaSR antiserum.

Results

Figure 40A:
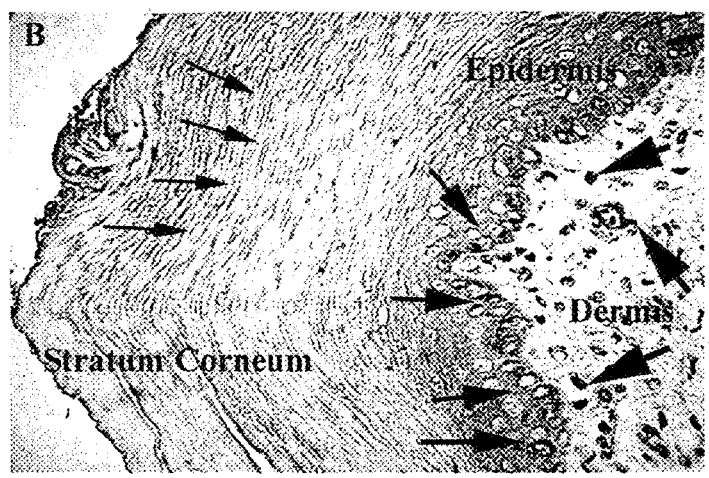
FIGS. 40A-C are images of fixed tissue sections of broiler chicken skin from the foot pad region of broiler chicken feet depicting the localization of calcium sensing receptor protein (CaSR) in epidermal and dermal tissues. Standard immunocytochemistry was performed on permeabilized fixed tissue sections of broiler chicken skin from the foot pad region of feet using either specific anti-CaSR antiserum (FIGS. 40A and C) or pre-immune anti-CaSR antiserum (FIG. 40B). The presence of bound anti-CaSR antibody (dark areas of staining) that denotes the location of CaSR protein is indicated by the arrows shown in FIG. 40A (see staining present in stratum corneum, epidermis and dermal skin regions) and FIG. 40C (see areas of intensely stained cells within dermis).
Figure 40B:
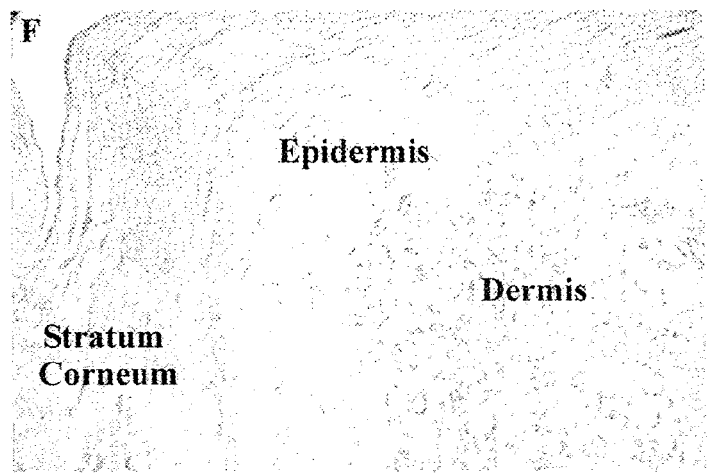
Figure 40C:
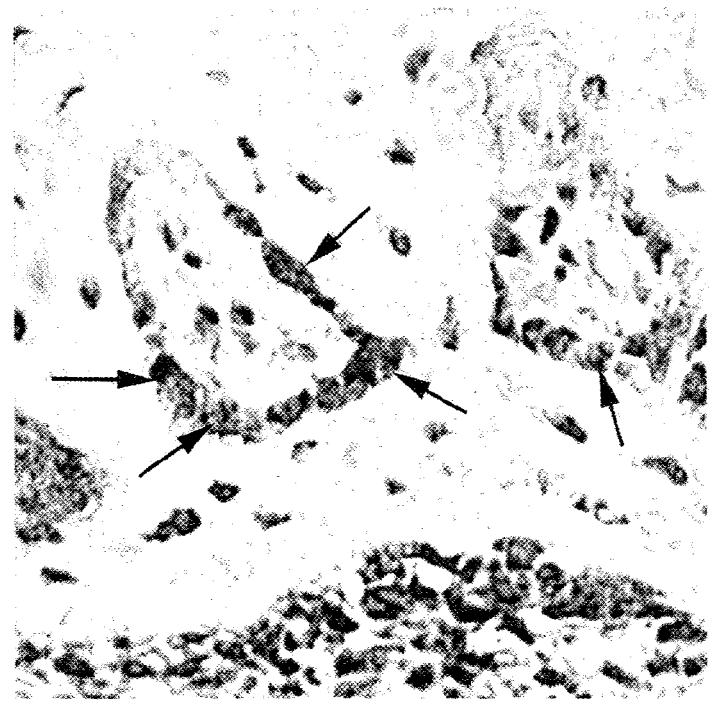

The presence of CaSR was detected in stratum corneum, epidermis and dermal skin regions (FIG. 40A) and within the dermis (FIG. 40C) of the skin of broiler chicken feet.

Example 15

42-Day Broiler Study

This MariCal broiler trial was conducted to investigate the benefits of chelated minerals in commercial broiler production.

Principal Objective: The principal objective of this 42 day floor pen study was to determine if the CaSR modulators MC 0100 or MC 106 produce alterations in broilers that were subjected to zinc depletion and then received oral zinc in the form of Mintrex Zn. The primary endpoints of the study were the measurement of growth, feed utilization and footpad scores in male broiler chickens raised under conditions resembling those used for commercial poultry production (floor pens with used litter).

Study Design: The study was divided into 3 phases for various experimental and control groups. All groups were sequentially fed identical base feeds that included starter (until Day 25), grower (Days 26-30) and finisher (Days 31-42) formulations that differed only in their zinc content or source. For the 4 experimental groups (B-E), these 3 phases included a 10 day interval of zinc depletion followed by a zinc repletion phase to Day 25 followed by rearing to Day 42. The 5th control group (Group A) was not subjected to an initial interval of zinc depletion and received a standard commercial diet until Day 25. The MC 100 and MC 106 compounds were administered in feed in combination with Mintrex Zn and compared to experimental treatment groups receiving either Mintrex alone (Mintrex ZN) or a low inorganic zinc-content diet (Zn Low). These groups were compared to the corresponding control group that was fed a standard inorganic-zinc content diet until day 25. After evaluation and analysis on Day 25, all study groups were continued through Day 42 without the addition of the MC compounds.

Protocol details for Groups A-E are outlined in Tables I-IV. Group A was not subjected to zinc depletion and was fed standard feed containing supplemental zinc (125 ppm zinc sulfate). After zinc depletion, each of the Groups B-E was fed different zinc replete diet. The diet of Group B was supplemented with 40 ppm zinc as zinc sulfate. By contrast, the diet of Group C was supplemented with Mintrex Zn alone (20 ppm supplemental Zn). The diet of Group D contained the same Mintrex Zn as in Group C plus MC 0100 (10 mg/kg BW or 70 mg/kg feed) while the diet fed to Group E contained Mintrex Zn plus MC 0106 (10 mg/kg BW or 70 mg/kg feed). After analysis on Day 25, the feeds of Groups C-E contained Mintrex Zn only without MC 100 or MC106.

TABLE I

Designation of Treatment Groups and sampling schedule
(*Grower and Finisher zinc content see below)

| Treatment Group | Lethal Bleed Day | Treatment | N |
|---|---|---|---|
| A | D 25, D 43 | Regular feed (zinc-supplemented throughout study at 100 ppm Zn as zinc sulfate*) | 8 pens |
| B | D 25, D 43 | Low-content zinc feed (zinc-supplemented at 40 ppm Zn as zinc sulfate starting on Day 10) | 8 pens |
| C | D 24, D 42 | Mintrex Zn (zinc-supplemented at 20 ppm Zn as Mintrex Zn starting on Day 10) | 8 pens |
| D | D 24, D 42 | MC 0100 (70 ppm in feed) + Mintrex Zn (zinc-supplemented at 20 ppm Zn as Mintrex Zn starting on Day 10) | 8 pens |
| E | D 24, D 42 | MC 0106 (70 ppm in feed) + Mintrex Zn (zinc-supplemented at 20 ppm Zn as Mintrex Zn starting on Day 10) | 8 pens |

Table II shows the feeding schedule and targeted concentrations of zinc designed for each of the treatment groups.

Table III shows the results of confirmatory QC zinc content analyses for each of the feeds conducted after completion of the trial by an outside contract analysis laboratory. Note that this analysis revealed the zinc content of all feeds were appropriate with the exception of Group A where a misformulation in both the grower and finisher diets provided no supplemental zinc as required by the protocol. Thus, data from the Group A control broilers is only valid for this comparison study from Day 0-25 and not thereafter.

TABLE II

Feeding schedule and targeted concentration of added zinc in feed for each Treatment Group

| | A inorganic Zn | B inorganic Zn | C Mintrex Zn | D Mintrex Zn + MC 0100 | E Mintrex Zn + MC 0106 |
|---|---|---|---|---|---|
| Day 0-9 Starter Feed | 100 ppm | * | * | * | * |
| Day 10-24/25 Starter Feed | 100 ppm | 40 ppm | 20 ppm | 20 ppm (1) | 20 ppm (2) |
| Day 25-30 Grower Feed | 100 ppm | 40 ppm | 20 ppm | 20 ppm | 20 ppm |
| Day 31-42 Finisher Feed | 100 ppm | 40 ppm | 20 ppm | 20 ppm | 20 ppm |

* No supplemental zinc added
(1) MC 0100 added to feed at 70 ppm
(2) MC 0106 added to feed at 70 ppm

TABLE III

Feeding schedule and actual concentration of zinc in feed for each Treatment Group

| | A inorganic Zn | B inorganic Zn | C Mintrex Zn | D Mintrex Zn + MC 0100 | E Mintrex Zn + MC 0106 |
|---|---|---|---|---|---|
| Day 0-9 Starter Feed | 128.5 ppm | 36.1 ppm* | 36.1 ppm* | 36.1 ppm* | 36.1 ppm* |
| Day 10-24/25 Starter Feed | 128.5 ppm | 72.6 ppm | 64.2 ppm | 58.8 ppm (1) | 60.4 ppm (2) |
| Day 25-30 Grower Feed | 39.7 ppm* | 78.8 ppm | 57.3 ppm | 57.3 ppm | 57.3 ppm |

TABLE III-continued

Feeding schedule and actual concentration of zinc in feed for each Treatment Group

| | A inorganic Zn | B inorganic Zn | C Mintrex Zn | D Mintrex Zn + MC 0100 | E Mintrex Zn + MC 0106 |
|---|---|---|---|---|---|
| Day 31-42 Finisher Feed | 32.9 ppm* | 71.9 ppm | 54.2 ppm | 54.2 ppm | 54.2 ppm |

*No supplemental zinc added
(1) MC 0100 added to feed at 70 ppm
(2) MC 0106 added to feed at 70 ppm Table IV summarizes the diet composition for Starter, Grower and Finisher feed used in this trial. For Trace Minerals a special Zn-free mix provided by NOVUS was used in all feed types and supplemented with zinc at specific target concentrations (see Tables II&III).

TABLE IV

Diet composition of Trial Feeds (g/kg)

| FEED TYPE | Starter g/kg | | Grower g/kg | Finisher g/kg |
|---|---|---|---|---|
| Corn, Yellow #2 | 598 | Corn AS 101 14 | 645 | 701 |
| Soymeal 48% | 308 | Soybean Meal A | 265 | 207 |
| Pork Meat&Bone | 50.00 | Pork Meat&Bone | 50.00 | 56.93 |
| Fat. Animal Stb | 23.62 | Animal Fat 340 | 23.18 | 22.82 |
| Deflour Phosph | 5.01 | Salt | 4.31 | 4.68 |
| Limestone | 4.59 | Limestone | 4.10 | 3.14 |
| Salt 96+% | 4.08 | Deflour Phosph | 3.50 | 0.00 |
| Methionine DL | 2.20 | DL-Methionine | 2.32 | 1.75 |
| Vitamins.Broiler[1] | 1.00 | Poultry Vitamin | 1.00 | 1.00 |
| Trace Minerals | 1.00 | Poultry Trace Min | 1.00 | 1.00 |
| choline Cl-60 | 0.94 | Choline Chloride | 0.87 | 0.57 |
| L-Lysine HCl | 0.91 | L-Lysine | 0.59 | 0.17 |
| Calcium (%) | 0.890 | | 0.82 | 0.72 |
| Avail Phosphorus (%) | 0.420 | | 0.39 | 0.35 |

[1]Vitamin premix provides (mg kg$^{-1}$ diet): thiamin, 1.9; riboflavin, 7.7; pantothenic acid, 12.1; niacin, 27.6; pyridoxine, 3.1; folacin, 1.00; biotin, 0.088; vitamin B$_{12}$, 0.014; vitamin K, 1.93; vitamin A, 10,472 IU; vitamin D, 3031 IU.

Animals

One day old broiler chicks (Cobb 500) were randomly allocated (8 pens per treatment in a block design with 5 pens per block and 27 birds/pen). Following their pen placement, all chicks from Groups B-E were zinc depleted by feeding a low zinc-content diet for 9 Days. By contrast, Group A received standard starter feed with supplemental zinc (see Table III) until Day 25. On Day 10 the bird count was adjusted to 24 in each pen and feed containing the respective experimental treatments (see Tables I-III) was administered until Day 25. After sampling on Days 24 and 25, the bird count was adjusted to 14 in each pen (feed treatments see Table II&III). The birds were allowed free access to both feed and water ad libitum. Feed consumption was quantified on Days 10, 24, 30 and 42. Individual bird weights were determined on Days 10, 24 and 42 and pen weights were taken on Days 25 and 30.

Sampling and Processing

On Day 24, eight birds were selected randomly from each pen from Treatment Groups C, D, and E and whole blood (~3 ml) was obtained by heart puncture. The blood was allowed to clot and serum was separated by centrifugation (IEC HN-SII centrifuge, 10 min at 2000 rpm at RT). Serum parameters (ionized calcium, sodium, chloride and potassium) were determined the same day using the ABL 70 Radiometer (Radiometer, Copenhagen). The remaining serum was frozen and stored at −20° C. until analysis of additional parameters (see below). At the time of blood sampling, the footpads of each birds were scored for severity of lesions by a single experienced analyst (scores 0-3). Tissue samples (mid jejunum and ileo-cecal junction) were removed from 16 randomly selected birds from each group within 5-15 min after heart puncture.

On Day 25 eight birds were selected randomly from each pen in Treatments A and B and processed as described above.

At the end of the trial (Days 42 and 43) the same number of birds were sampled as described above.

Serum Analysis

Total protein (Pierce 660 nm Protein Assay) and total calcium, magnesium, phosphorus and glucose (Stanbio Laboratories) were determined (triplicates/sample) using commercial kits and a plate reader (Versamax, Molecular Devices).

Statistical Methods

Data were analyzed using the general linear models procedure in SYSTAT 10 followed by Tukey HSD Multiple Comparisons.

Results

Figure 41:
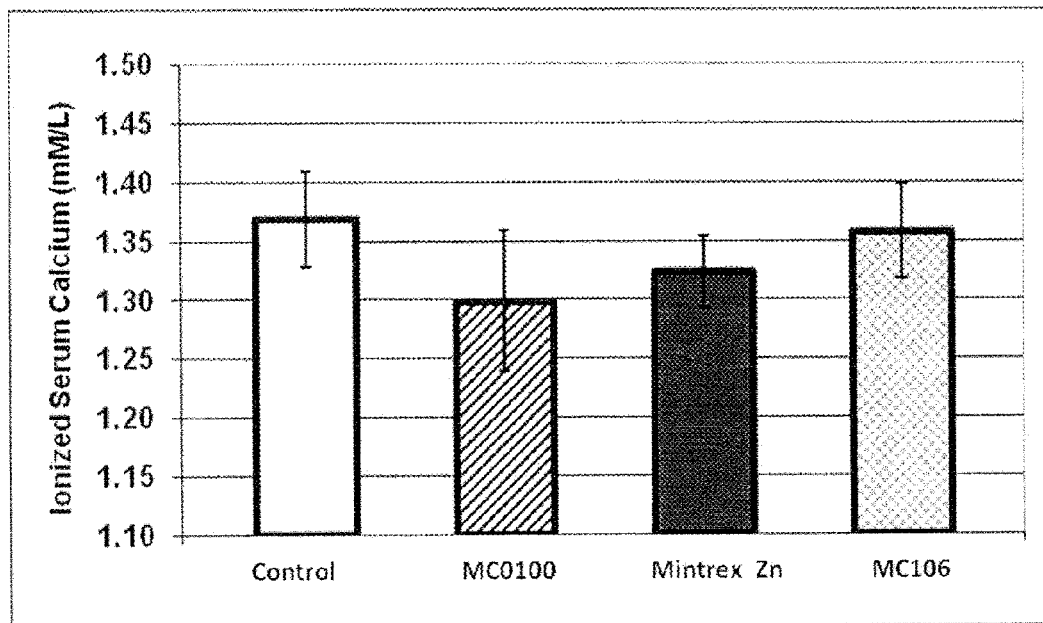
FIG. 41 is a graph depicting a comparison of the effects of inclusion of the CaSR modulators MC0100 and MC106, or Mintrex Zn, on the serum calcium in broiler chickens under nonstressed pen trial conditions. As compared to Control values, significant reductions in the mean serum calcium concentration were observed for the two groups of birds receiving either MC0100 or Mintrex Zn as a feed additive. No differences in serum pH, Na+, K+ or Cl− were observed for any of the groups tested.

Male Cobb strain broiler chickens were reared in standard minipens and fed standard feed. As part of the feed additives, either MC0100 (10 mg/kg) or Mintrex Zn (250 mg/kg or MC 106 (10 mg/kg) were included in individual groups of birds. Blood samples were obtained by heart puncture on Day 14 of the study and the Serum calcium concentrations determined using a radiometer blood gas instrument (Radiometer, Copenhagen). As compared to Control values, significant reductions in the mean serum calcium concentration was observed for the two groups of birds receiving either MC0100 or Mintrex Zn as a feed additive (FIG. 41). No differences in serum pH, Na+, K+ or Cl− were observed for any of the groups tested.

Figure 42A:
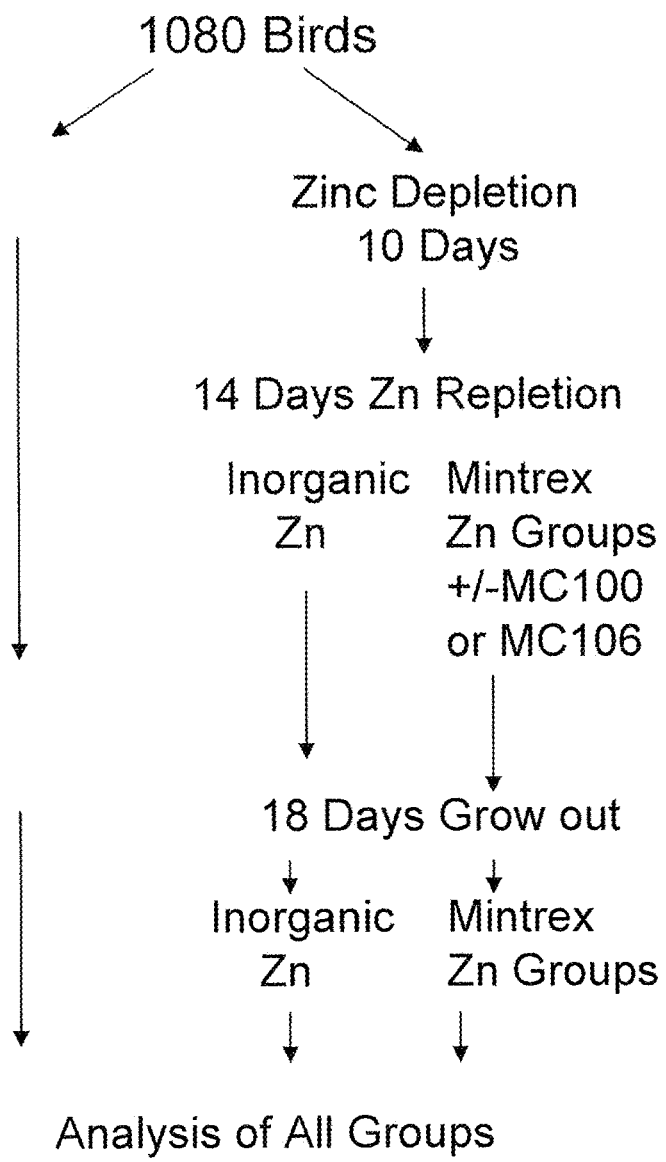
FIG. 42A is a schematic showing the division of a total of 1080 male Cobb strain birds into 5 different treatment groups that were subjected to identical rearing conditions that included being reared using dirty litter conditions to simulate standard large scale chicken rearing facilities.
Figure 42B:
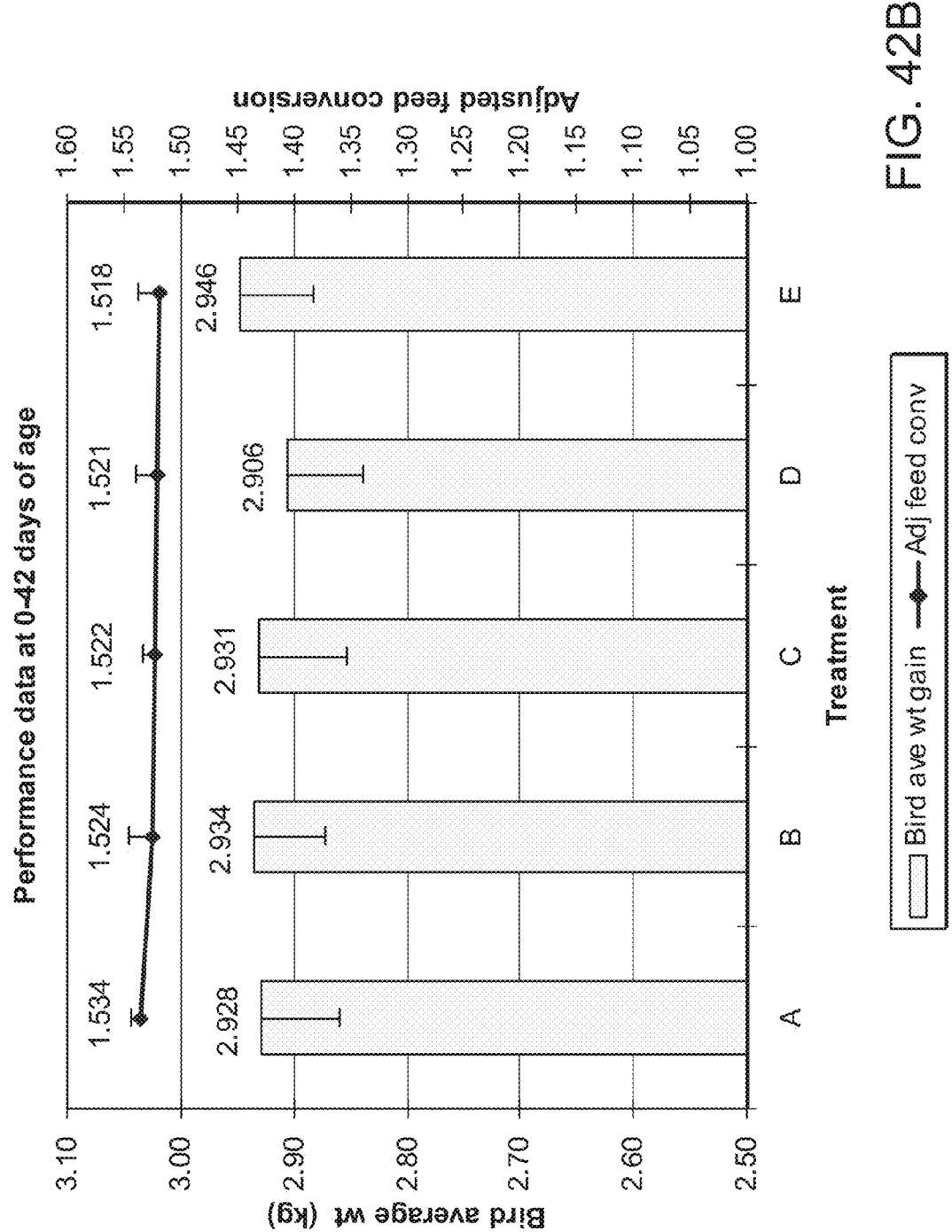
FIG. 42B is a graph showing a comparison of performance parameters for broiler chicken groups shown in FIG. 42A, including mean values for both average weight and adjusted feed conversion ratio (FCR) in the animals from 5 treatment groups. Control Group A received standard feeds which included 100 ppm inorganic zinc throughout the 42 day grow out. Groups B-E were subjected to a 10 day interval of zinc depletion followed by zinc repletion using different sources of dietary zinc (Group B—40 ppm inorganic zinc), Mintrex Zn (Group C—20 ppm Zinc), Mintrex Zn +MC0100 (Group D—20 ppm Zinc; 70 ppm MC0100) or Mintrex Zn+MC106 (Group E—20 ppm zinc; 70 ppm MC 106). While there were no significant differences in the means between the 5 groups, Group E achieved the largest mean body weight and lowest FCR.

A comparison of performance parameters for broiler chickens reared under dirty litter conditions and subjected to zinc depletion for a 10 day interval prior to grow out for a total of 42 days was performed. A total of 1080 male Cobb strain birds were divided into 5 different treatment groups (FIG. 42A). These 5 groups were subjected to identical rearing conditions that included being reared using dirty litter conditions to simulate standard large scale chicken rearing facilities. The 5 groups included a Control group (A) that received standard feeds which included 100 ppm inorganic zinc throughout the 42 day grow out. By contrast, the remaining 4 groups were subjected to a 10 day interval of zinc depletion whereby the zinc content of their food was reduced to minimal levels. Following this interval of zinc depletion, the birds received a 14 day interval of zinc repletion using different sources of dietary zinc. These included either inorganic zinc (Group B-40 ppm inorganic zinc), Mintrex Zn (Group C—20 ppm Zinc), Mintrex Zn+MC0100 (Group D—20 ppm Zinc;

70 ppm MC0100) or Mintrex Zn+MC106 (Group E—20 ppm zinc; 70 ppm MC106). After a total of 24 days of grow out, Groups C-E all received Mintrex Zn only (20 ppm Zinc) until their harvest analysis at day 42 of age. Performance data for Groups A-E is shown FIG. 42B and includes mean values for both average weight and adjusted feed conversion ratio (FCR). While there were no significant differences in the means between the 5 groups, the group that achieved the largest mean body weight and lowest FCR was Group E, which received the combination of Mintrex Zn and MC106.

Figure 43A:
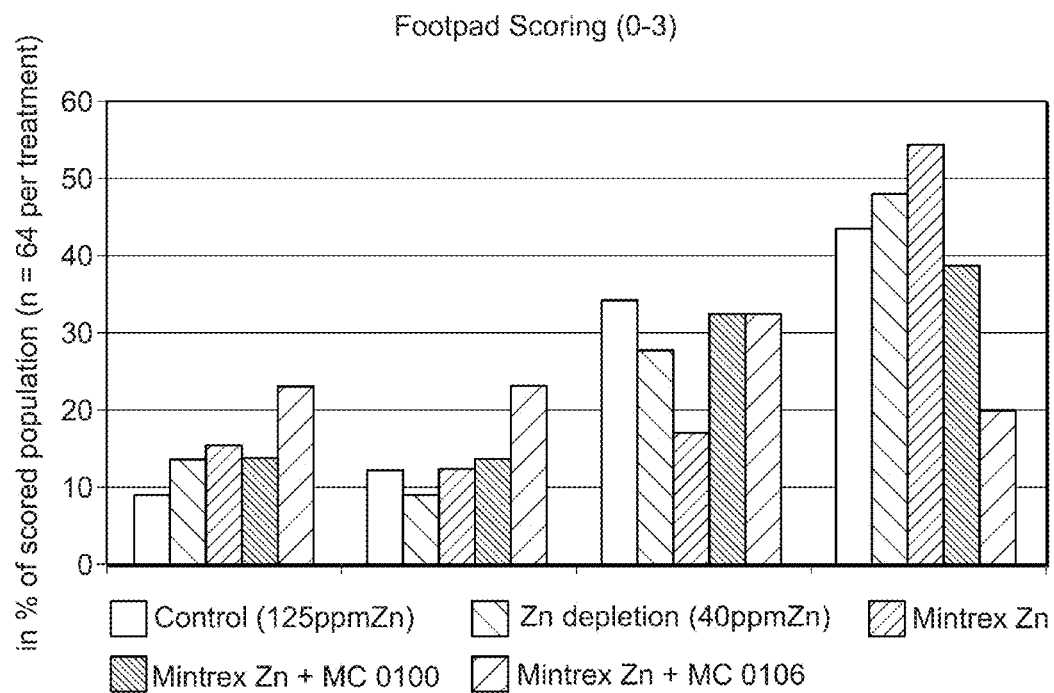
FIG. 43A is a graph showing the frequency of foot pad lesions in broiler chickens for the 5 treatment groups shown in FIG. 42B after 24/25 days of rearing under dirty litter conditions. The group receiving the combination of Mintrex Zn+MC 106 displayed a significant reduction in the severity and frequency of foot pad lesions as compared to all other groups.
Figure 43B:
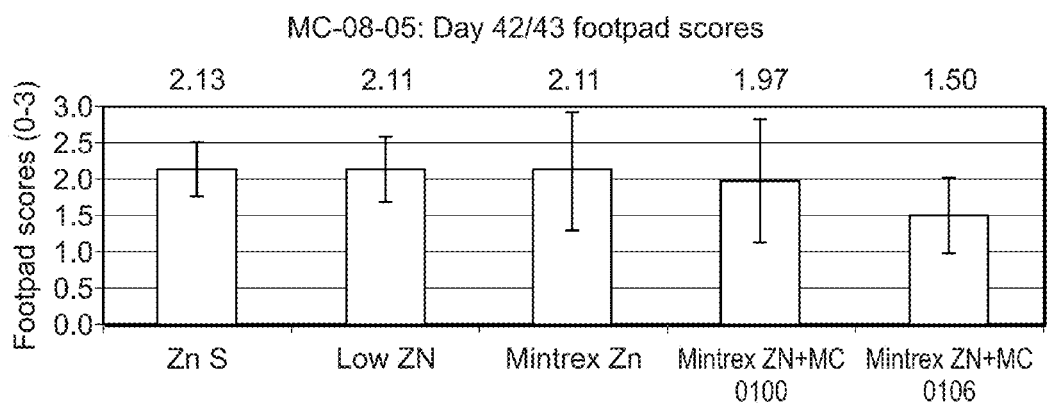
FIG. 43B is a graph showing the severity of foot pad lesions in broiler chickens for the 5 treatment groups shown in FIG. 42B after 24/25 days of rearing under dirty litter conditions. The severity of the foot pad lesions present was graded on a scale from 0 (no lesions present), 1 (mild lesions present), 2 (moderate lesions present) and 3 (severe lesions present). Mean scores for foot pad severity for each of the 5 test groups are shown. There was a significant reduction in the mean foot pad severity score of the group receiving Mintrex Zn+MC 106 as compared to all other groups.

A comparison of the frequency and severity of foot pad lesions present in broiler chickens after 24/25 days of rearing under dirty litter conditions and, in selected cases, subjected to a 10 day interval of zinc depletion. A total of 1080 Cobb strain birds were divided into 5 different treatment groups as described above. On days 23 and 24 of grow out, the foot pads of all groups were examined and the frequency and severity of foot pad lesions were determined by an experienced animal veterinarian. The severity of the foot pad lesions present was graded on a scale from 0 (no lesions present), 1 (mild lesions present), 2 (moderate lesions present) and 3 (severe lesions present). As compared to the other 4 experimental groups, the group receiving the combination of Mintrex Zn+MC106 displayed a significant reduction in the severity and frequency of foot pad lesions as compared to all other groups (FIG. 43A). In addition, there was a significant reduction in the mean foot pad severity score of the group receiving Mintrex Zn+MC 106 as compared to all other groups (FIG. 43B).

Figure 44A:
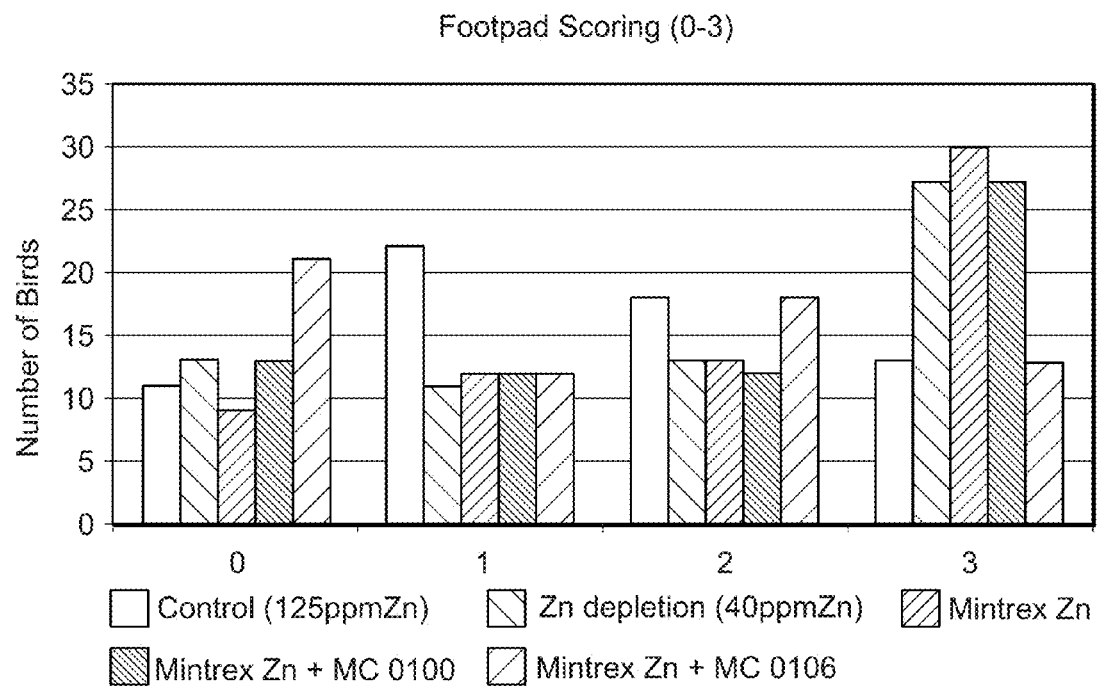
FIG. 44A is a graph showing the frequency of foot pad lesions in broiler chickens for the 5 treatment groups shown in FIG. 42B after 42/43 days of rearing under dirty litter conditions. The 5 groups included a Control group (ZnS) that received standard feeds which included 100 ppm inorganic zinc throughout the 42 day grow out. The group receiving the combination of Mintrex Zn+MC106 displayed a significant reduction in the frequency of foot pad lesions as compared to all other groups.
Figure 44B:
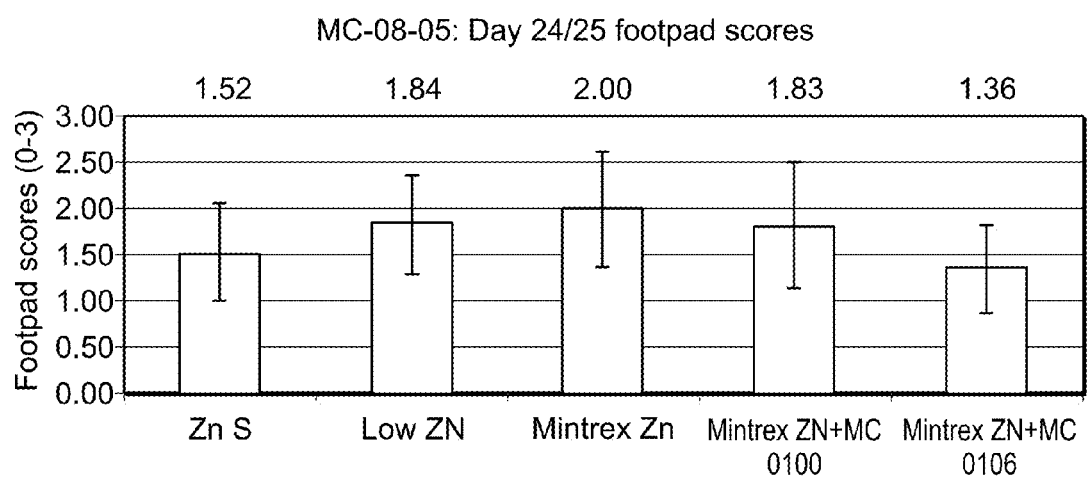
FIG. 44B is a graph showing the severity of foot pad lesions in broiler chickens for the 5 treatment groups shown in FIG. 42B after 42/43 days of rearing under dirty litter conditions. The 5 groups included a Control group (ZnS) that received standard feeds which included 100 ppm inorganic zinc throughout the 42 day grow out. The severity of the foot pad lesions present was graded on a scale from 0 (no lesions present), 1 (mild lesions present), 2 (moderate lesions present) and 3 (severe lesions present). Mean scores for foot pad severity for each of the 5 test groups are shown. There was a significant reduction in the mean foot pad severity score of the group receiving Mintrex Zn+MC 106 as compared to all other groups.

A comparison of the frequency and severity of foot pad lesions present in broiler chickens after 42/43 days of rearing under dirty litter conditions and, in selected cases, subjected to a 10 day interval of zinc depletion, was determined. The group receiving the combination of Mintrex Zn+MC 106 displayed a significant reduction in the severity and frequency of foot pad lesions as compared to all other groups (FIG. 44A). There was a significant reduction in the mean foot pad severity score of the group receiving Mintrex Zn+MC106 as compared to all other groups (FIG. 44B).

A comparison of the ionized and total serum calcium of broiler chickens on Day 24/25 of a 42 Day Grow Out. Birds receiving the combination of Mintrex Zn+MC0100 displayed a ionized calcium concentration that was significantly lower than all other test groups (FIG. 45A). Mean values for the total serum calcium concentration for each of the 5 test groups were obtained from the same samples used for determination of ionized calcium shown in FIG. 45A. The birds receiving the combination of Mintrex Zn+MC106 displayed the highest total calcium concentrations (FIG. 45B).

The relevant teachings of all patents, published applications and references cited herein are incorporated by reference in their entirety.

While this invention has been particularly shown and described with references to example and preferred embodiments thereof, it will be understood by those skilled in the art that various changes may be made therein without departing from the scope of the invention encompassed by the appended claims and equivalents thereof.

What is claimed is:

1. A method of inhibiting foot pad lesions in a non-human terrestrial animal, comprising administering to the animal an effective amount one or more Calcium Sensing Receptor (CaSR) modulator(s), thereby inhibiting foot pad lesions in the animal.

2. The method of claim 1, wherein the one or more CaSR modulator(s) is a CaSR antagonist.

3. The method of claim 2, wherein the CaSR antagonist is a phenylalkylamine.

4. The method of claim 3, wherein the phenylalkylamine is MC106.

5. The method of claim 1, wherein the one or more CaSR modulator(s) is a naturally occurring compound.

6. The method of claim 1, wherein the animal has ingested an agent that adversely affects calcium homeostasis.

7. The method of claim 6, wherein the agent is a chelated mineral compound.

8. The method of claim 7, wherein the chelated mineral compound comprises at least one divalent cation selected from the group consisting of $Zn^{2+}$, $Cu^{2+}$ and $Mn^{2+}$.

9. The method of claim 7, wherein the chelated mineral compound comprises (2-hydroxy-4-methylthio)butanoic acid (HMTBa) and $Zn^{2+}$.

10. The method of claim 9, wherein the chelated mineral compound is MINTREX®Zn.

11. The method of claim 7, wherein the chelated mineral compound comprises methionine or glycine and $Zn^{2+}$.

12. The method of claim 7, wherein the chelated mineral compound is selected from the group consisting of a zinc proteinate, a copper proteinate, a manganese proteinate and zinc bacitracin, or a combination thereof.

13. The method of claim 1, wherein the non-human terrestrial animal is a mammal.

14. The method of claim 1, wherein the non-human terrestrial animal is an avian animal.

15. The method of claim 14, wherein the avian animal is selected from the group consisting of a chicken, a turkey, a duck, a goose, a pheasant, a grouse and an ostrich.

16. The method of claim 14, wherein the avian animal is a duck.

17. A method of inhibiting a foot pad lesion in a non-terrestrial avian animal, comprising administering a food composition to the animal, wherein the food composition comprises:
- a.) at least one chelated mineral compound in an amount that adversely affects calcium homeostasis in the animal;
- b.) 25-hydroxycholecalciferol at a concentration of at least about 0.05% by weight; and
- c.) a source of calcium.

18. The method of claim 17, wherein the at least one chelated mineral compound comprises (2-hydroxy-4-methylthio)butanoic acid (HMTBa) and a divalent cation selected from the group consisting of $Zn^{2+}$, $Cu^{2+}$ and $Mn^{2+}$.

19. The method of claim 17, wherein the at least one chelated mineral compound is present in the composition at a concentration of at least about 5 to about 50 parts per million.

20. The method of claim 17, wherein the source of calcium is present in the composition at a concentration of about 1.40% to about 1.45% by weight.

* * * * *